(12) United States Patent
Lurie et al.

(10) Patent No.: US 11,583,645 B2
(45) Date of Patent: Feb. 21, 2023

(54) VACUUM AND POSITIVE PRESSURE VENTILATION SYSTEMS AND METHODS FOR INTRATHORACIC PRESSURE REGULATION

(71) Applicant: ZOLL Medical Corporation, Chelmsford, MA (US)

(72) Inventors: Keith G. Lurie, Minneapolis, MN (US); Anja Metzger, Stillwater, MN (US); Kurt Krueger, Stacy, MN (US); Greg Voss, Lakeville, MN (US)

(73) Assignee: ZOLL Medical Corporation, Chelmsford, MA (US)

( * ) Notice: Subject to any disclaimer, the term of this patent is extended or adjusted under 35 U.S.C. 154(b) by 483 days.

(21) Appl. No.: 16/685,226

(22) Filed: Nov. 15, 2019

(65) Prior Publication Data
US 2020/0206454 A1 Jul. 2, 2020

Related U.S. Application Data

(63) Continuation of application No. 14/602,057, filed on Jan. 21, 2015, now Pat. No. 10,512,749, which is a
(Continued)

(51) Int. Cl.
*A61M 16/00* (2006.01)
*A61M 16/06* (2006.01)
(Continued)

(52) U.S. Cl.
CPC ........... *A61M 16/024* (2017.08); *A61H 31/02* (2013.01); *A61M 16/0003* (2014.02);
(Continued)

(58) Field of Classification Search
CPC ........... A61M 16/0009; A61M 16/024; A61M 16/085; A61M 16/12; A61M 16/201;
(Continued)

(56) References Cited

U.S. PATENT DOCUMENTS

| 1,848,232 A | 3/1932 | Swope et al. |
| 2,325,049 A | 7/1943 | Frye et al. |

(Continued)

FOREIGN PATENT DOCUMENTS

| AU | 1487792 B | 10/1992 |
| AU | 60539 B | 11/1994 |

(Continued)

OTHER PUBLICATIONS

US 5,584,866 A, 12/1996, Kroll et al. (withdrawn)
(Continued)

*Primary Examiner* — Colin W Stuart
*Assistant Examiner* — Douglas Y Sul
(74) *Attorney, Agent, or Firm* — The Webb Law Firm

(57) ABSTRACT

Medical techniques include systems and methods for administering a positive pressure ventilation, a positive end expiratory pressure, and a vacuum to a person. Approaches also include treating a person with an intrathoracic pressure regulator so as to modulate or upregulate the autonomic system of the person, and treating a person with a combination of an intrathoracic pressure regulation treatment and an intra-aortic balloon pump treatment.

20 Claims, 36 Drawing Sheets

Related U.S. Application Data continuation of application No. 12/819,959, filed on Jun. 21, 2010, now Pat. No. 8,967,144.

(60) Provisional application No. 61/218,763, filed on Jun. 19, 2009.

(51) Int. Cl.

| | | |
|---|---|---|
| *A61M 16/20* | (2006.01) | |
| *A61M 16/08* | (2006.01) | |
| *A61M 16/04* | (2006.01) | |
| *A61M 16/12* | (2006.01) | |
| *A61N 1/36* | (2006.01) | |
| *A61M 16/10* | (2006.01) | |
| *A61N 1/39* | (2006.01) | |
| *A61H 31/02* | (2006.01) | |

(52) U.S. Cl.
CPC .... *A61M 16/0009* (2014.02); *A61M 16/0012* (2014.02); *A61M 16/0057* (2013.01); *A61M 16/04* (2013.01); *A61M 16/06* (2013.01); *A61M 16/085* (2014.02); *A61M 16/0825* (2014.02); *A61M 16/0858* (2014.02); *A61M 16/20* (2013.01); *A61M 16/201* (2014.02); *A61M 16/202* (2014.02); *A61M 16/208* (2013.01); *A61H 2230/06* (2013.01); *A61H 2230/30* (2013.01); *A61H 2230/40* (2013.01); *A61M 16/009* (2013.01); *A61M 16/0078* (2013.01); *A61M 16/0833* (2014.02); *A61M 16/1065* (2014.02); *A61M 16/12* (2013.01); *A61M 16/205* (2014.02); *A61M 2016/0027* (2013.01); *A61M 2016/0036* (2013.01); *A61M 2016/102* (2013.01); *A61M 2205/3331* (2013.01); *A61M 2205/3334* (2013.01); *A61M 2205/3553* (2013.01); *A61M 2205/3584* (2013.01); *A61M 2205/50* (2013.01); *A61M 2205/502* (2013.01); *A61M 2205/505* (2013.01); *A61M 2230/06* (2013.01); *A61M 2230/205* (2013.01); *A61M 2230/208* (2013.01); *A61M 2230/30* (2013.01); *A61M 2230/42* (2013.01); *A61M 2230/432* (2013.01); *A61M 2230/50* (2013.01); *A61N 1/3601* (2013.01); *A61N 1/39* (2013.01); *A61N 1/39044* (2017.08)

(58) Field of Classification Search
CPC ............... A61M 16/202; A61M 16/20; A61M 2016/102; A61M 2205/50; A61M 2205/502; A61M 2205/505; A61M 2230/30; A61M 2230/40; A61H 31/02; A61H 2201/5043; A61H 2201/5046
See application file for complete search history.

(56) References Cited

U.S. PATENT DOCUMENTS

| | | | |
|---|---|---|---|
| 2,774,346 A | 12/1956 | Halliburton | |
| 2,854,982 A | 10/1958 | Pagano | |
| 2,904,898 A | 9/1959 | Marsden | |
| 3,009,266 A | 11/1961 | Brook | |
| 3,049,811 A | 8/1962 | Ruben | |
| 3,068,590 A | 12/1962 | Padellford | |
| 3,077,884 A | 2/1963 | Batrow et al. | |
| 3,191,596 A | 6/1965 | Bird et al. | |
| 3,199,225 A | 8/1965 | Robertson et al. | |
| 3,209,469 A | 10/1965 | James | |
| 3,216,413 A | 11/1965 | Mota | |
| 3,274,705 A | 9/1966 | Breakspear | |
| 3,276,147 A | 10/1966 | Padellford | |
| 3,307,541 A | 3/1967 | Hewson | |
| 3,357,426 A | 12/1967 | Cohen | |
| 3,420,232 A | 1/1969 | Bickford | |
| 3,459,216 A | 8/1969 | Bloom et al. | |
| 3,467,092 A | 9/1969 | Bird et al. | |
| 3,509,899 A | 5/1970 | Hewson | |
| 3,515,163 A | 6/1970 | Freeman | |
| 3,523,529 A | 8/1970 | Kissen | |
| 3,552,390 A | 1/1971 | Muller | |
| 3,562,924 A | 2/1971 | Baerman et al. | |
| 3,562,925 A | 2/1971 | Baermann et al. | |
| 3,568,333 A | 3/1971 | Clark | |
| 3,662,751 A | 5/1972 | Barkalow et al. | |
| 3,669,108 A | 6/1972 | Sundblom et al. | |
| 3,734,100 A | 5/1973 | Walker et al. | |
| 3,739,776 A | 6/1973 | Bird et al. | |
| 3,794,043 A | 2/1974 | McGinnis | |
| 3,815,606 A | 6/1974 | Mazal | |
| 3,834,383 A | 9/1974 | Weigl et al. | |
| 3,872,609 A | 3/1975 | Smrcka | |
| 3,874,093 A | 4/1975 | Garbe | |
| 3,875,626 A | 4/1975 | Tysk et al. | |
| 3,933,171 A | 1/1976 | Hay | |
| 3,949,388 A | 4/1976 | Fuller | |
| 3,973,564 A | 8/1976 | Carden | |
| 3,981,398 A | 9/1976 | Boshoff | |
| 3,993,059 A | 11/1976 | Sjostrand | |
| 4,037,595 A | 7/1977 | Elam | |
| 4,041,943 A | 8/1977 | Miller | |
| 4,054,134 A | 10/1977 | Kritzer | |
| 4,077,400 A | 3/1978 | Harrigan | |
| 4,077,404 A | 3/1978 | Elam | |
| 4,095,590 A | 6/1978 | Harrigan | |
| 4,166,458 A | 9/1979 | Harrigan | |
| 4,193,406 A | 3/1980 | Jinotti | |
| 4,198,963 A | 4/1980 | Barkalow et al. | |
| 4,226,233 A | 10/1980 | Kritzer | |
| 4,237,872 A | 12/1980 | Harrigan | |
| 4,240,419 A | 12/1980 | Furlong et al. | |
| 4,259,951 A | 4/1981 | Chernack et al. | |
| 4,262,667 A | 4/1981 | Grant | |
| 4,297,999 A | 11/1981 | Kitrell | |
| 4,298,023 A | 11/1981 | McGinnis | |
| 4,316,458 A | 2/1982 | Hammerton-Fraser | |
| 4,320,754 A | 3/1982 | Watson et al. | |
| 4,326,507 A | 4/1982 | Barkalow | |
| 4,331,426 A | 5/1982 | Sweeney | |
| 4,349,015 A | 9/1982 | Alferness | |
| 4,360,345 A | 11/1982 | Hon | |
| 4,397,306 A | 8/1983 | Weisfeldt et al. | |
| 4,424,806 A | 1/1984 | Newman et al. | |
| 4,446,864 A | 5/1984 | Watson et al. | |
| 4,448,192 A | 5/1984 | Stawitcke et al. | |
| 4,449,526 A | 5/1984 | Elam | |
| 4,481,938 A | 11/1984 | Lindley | |
| 4,501,582 A | 2/1985 | Schulz | |
| 4,513,737 A | 4/1985 | Mabuchi | |
| 4,519,388 A | 5/1985 | Schwanbom et al. | |
| 4,520,811 A | 6/1985 | White et al. | |
| 4,533,137 A | 8/1985 | Sonne | |
| 4,543,951 A | 10/1985 | Phuc | |
| 4,588,383 A | 5/1986 | Parker et al. | |
| 4,598,706 A | 7/1986 | Darowski et al. | |
| 4,601,465 A | 7/1986 | Roy | |
| 4,602,653 A | 7/1986 | Ruiz-Vela et al. | |
| 4,637,386 A | 1/1987 | Baum | |
| 4,738,249 A | 4/1988 | Linman et al. | |
| 4,750,493 A | 6/1988 | Brader | |
| 4,774,941 A | 10/1988 | Cook | |
| 4,797,104 A | 1/1989 | Laerdal et al. | |
| 4,807,638 A | 2/1989 | Sramek | |
| 4,809,683 A | 3/1989 | Hanson | |
| 4,827,935 A | 5/1989 | Geddes et al. | |
| 4,828,501 A | 5/1989 | Ingenito et al. | |
| 4,838,257 A * | 6/1989 | Hatch | A61M 16/204 128/204.18 |
| 4,863,385 A * | 9/1989 | Pierce | G09B 23/288 434/265 |
| 4,881,527 A | 11/1989 | Lerman | |

(56) References Cited

U.S. PATENT DOCUMENTS

| | | |
|---|---|---|
| 4,898,166 A | 2/1990 | Rose et al. |
| 4,898,167 A | 2/1990 | Pierce et al. |
| 4,928,674 A | 5/1990 | Halperin et al. |
| 4,932,879 A | 6/1990 | Ingenito et al. |
| 4,971,042 A | 11/1990 | Lerman |
| 4,971,051 A | 11/1990 | Toffolon |
| 4,984,987 A | 1/1991 | Brault et al. |
| 5,014,698 A | 5/1991 | Cohen |
| 5,016,627 A | 5/1991 | Dahrendorf et al. |
| 5,029,580 A | 7/1991 | Radford et al. |
| 5,042,500 A | 8/1991 | Norlien et al. |
| 5,050,593 A | 9/1991 | Poon |
| 5,056,505 A | 10/1991 | Warwick et al. |
| 5,083,559 A | 1/1992 | Brault et al. |
| 5,109,840 A | 5/1992 | Daleiden |
| 5,119,825 A | 6/1992 | Huhn |
| 5,163,424 A | 11/1992 | Kohnke |
| 5,183,038 A | 2/1993 | Hoffman et al. |
| 5,184,620 A | 2/1993 | Cudahy et al. |
| 5,188,098 A | 2/1993 | Hoffman et al. |
| 5,193,529 A | 3/1993 | Labaere |
| 5,193,544 A | 3/1993 | Jaffe |
| 5,195,896 A | 3/1993 | Sweeney et al. |
| 5,217,006 A | 6/1993 | McCulloch |
| 5,231,086 A | 7/1993 | Sollevi |
| 5,235,970 A | 8/1993 | Augustine |
| 5,238,409 A | 8/1993 | Brault et al. |
| 5,239,988 A | 8/1993 | Swanson et al. |
| 5,263,476 A | 11/1993 | Henson |
| 5,265,595 A | 11/1993 | Rudolph |
| 5,282,463 A | 2/1994 | Hammersley |
| 5,295,481 A | 3/1994 | Geeham |
| 5,301,667 A | 4/1994 | McGrail et al. |
| 5,305,743 A | 4/1994 | Brain |
| 5,306,293 A | 4/1994 | Zacouto |
| 5,312,259 A | 5/1994 | Flynn |
| 5,313,938 A | 5/1994 | Garfield et al. |
| 5,316,907 A | 5/1994 | Lurie et al. |
| 5,330,514 A | 7/1994 | Egelandsdal et al. |
| 5,335,654 A | 8/1994 | Rapoport |
| 5,353,788 A | 10/1994 | Miles |
| 5,355,879 A | 10/1994 | Brain |
| 5,359,998 A | 11/1994 | Lloyd |
| 5,366,231 A | 11/1994 | Hung |
| 5,377,671 A | 1/1995 | Biondi et al. |
| 5,383,786 A | 1/1995 | Kohnke |
| 5,388,575 A | 2/1995 | Taube |
| 5,392,774 A | 2/1995 | Sato |
| 5,395,399 A | 3/1995 | Rosenwald |
| 5,397,237 A | 3/1995 | Dhont et al. |
| 5,398,714 A | 3/1995 | Price |
| 5,413,110 A | 5/1995 | Cummings et al. |
| 5,423,685 A | 6/1995 | Adamson et al. |
| 5,423,772 A | 6/1995 | Lurie et al. |
| 5,425,742 A | 6/1995 | Joy |
| 5,437,272 A | 8/1995 | Fuhrman |
| 5,452,715 A | 9/1995 | Boussignac |
| 5,454,779 A | 10/1995 | Lurie et al. |
| 5,458,562 A | 10/1995 | Cooper |
| 5,468,151 A | 11/1995 | Egelandsdal et al. |
| 5,474,533 A | 12/1995 | Ward et al. |
| 5,477,860 A | 12/1995 | Essen-Moller |
| 5,490,820 A | 2/1996 | Schock et al. |
| 5,492,115 A | 2/1996 | Abramov et al. |
| 5,492,116 A | 2/1996 | Scarberry et al. |
| 5,496,257 A | 3/1996 | Kelly |
| 5,507,282 A | 4/1996 | Younes |
| 5,517,986 A | 5/1996 | Starr et al. |
| 5,544,648 A | 8/1996 | Fischer, Jr. |
| 5,549,106 A | 8/1996 | Gruenke et al. |
| 5,549,581 A | 8/1996 | Lurie et al. |
| 5,551,420 A | 9/1996 | Lurie et al. |
| 5,557,049 A | 9/1996 | Ratner |
| 5,580,255 A | 12/1996 | Flynn |
| 5,582,182 A | 12/1996 | Hillsman |
| 5,588,422 A | 12/1996 | Lurie et al. |
| 5,593,306 A | 1/1997 | Kohnke |
| 5,606,968 A | 3/1997 | Mang |
| 5,614,490 A | 3/1997 | Przybelski |
| 5,617,844 A | 4/1997 | King |
| 5,618,665 A | 4/1997 | Lurie et al. |
| 5,619,665 A | 4/1997 | Emma |
| 5,628,305 A | 5/1997 | Melker |
| 5,632,298 A | 5/1997 | Artinian |
| 5,643,231 A | 7/1997 | Lurie et al. |
| 5,645,522 A | 7/1997 | Lurie et al. |
| 5,657,751 A | 8/1997 | Karr, Jr. |
| 5,678,535 A | 10/1997 | DiMarco |
| 5,682,878 A * | 11/1997 | Ogden ............ A61M 16/022 128/204.18 |
| 5,685,298 A | 11/1997 | Idris |
| 5,692,498 A | 12/1997 | Lurie et al. |
| 5,697,364 A | 12/1997 | Chua et al. |
| 5,701,883 A | 12/1997 | Hete et al. |
| 5,701,889 A | 12/1997 | Danon |
| 5,704,346 A | 1/1998 | Inoue |
| 5,720,282 A | 2/1998 | Wright |
| 5,722,963 A | 3/1998 | Lurie et al. |
| 5,730,122 A | 3/1998 | Lurie |
| 5,735,876 A | 4/1998 | Kroll et al. |
| 5,738,637 A | 4/1998 | Kelly et al. |
| 5,743,864 A | 4/1998 | Baldwin, II |
| 5,782,883 A | 7/1998 | Kroll et al. |
| 5,794,615 A | 8/1998 | Estes |
| 5,806,512 A | 9/1998 | Abramov et al. |
| 5,814,086 A | 9/1998 | Hirschberg et al. |
| 5,817,997 A | 10/1998 | Wernig |
| 5,823,185 A | 10/1998 | Chang |
| 5,823,787 A | 10/1998 | Gonzalez et al. |
| 5,827,893 A | 10/1998 | Lurie et al. |
| 5,832,920 A | 11/1998 | Field |
| 5,853,292 A | 12/1998 | Eggert et al. |
| 5,881,725 A | 3/1999 | Hoffman et al. |
| 5,885,084 A | 3/1999 | Pastrick et al. |
| 5,891,062 A | 4/1999 | Schock et al. |
| 5,896,857 A | 4/1999 | Hely et al. |
| 5,916,165 A | 6/1999 | Duchon et al. |
| 5,919,210 A | 7/1999 | Lurie et al. |
| 5,927,273 A | 7/1999 | Federowicz et al. |
| 5,937,853 A | 8/1999 | Strom |
| 5,941,710 A | 8/1999 | Lampotang et al. |
| 5,975,081 A | 11/1999 | Hood et al. |
| 5,977,091 A | 11/1999 | Nieman et al. |
| 5,984,909 A | 11/1999 | Lurie et al. |
| 5,988,166 A | 11/1999 | Hayek |
| 6,001,085 A | 12/1999 | Lurie et al. |
| 6,010,470 A | 1/2000 | Albery et al. |
| 6,029,667 A | 2/2000 | Lurie |
| 6,042,532 A | 3/2000 | Freed et al. |
| 6,062,219 A | 5/2000 | Lurie et al. |
| 6,078,834 A | 6/2000 | Lurie et al. |
| 6,086,582 A | 7/2000 | Altman et al. |
| 6,123,074 A | 9/2000 | Hete |
| 6,131,571 A | 10/2000 | Lampotang et al. |
| 6,155,257 A | 12/2000 | Lurie et al. |
| 6,155,647 A | 12/2000 | Albecker, III |
| 6,165,105 A | 12/2000 | Boutellier et al. |
| 6,167,879 B1 | 1/2001 | Sievers et al. |
| 6,174,295 B1 | 1/2001 | Cantrell et al. |
| 6,176,237 B1 | 1/2001 | Wunderlich et al. |
| 6,193,519 B1 | 2/2001 | Eggert et al. |
| 6,209,540 B1 | 4/2001 | Sugiura et al. |
| 6,224,562 B1 | 5/2001 | Lurie et al. |
| 6,234,916 B1 | 5/2001 | Carusillo et al. |
| 6,234,985 B1 | 5/2001 | Lurie et al. |
| 6,277,107 B1 | 8/2001 | Lurie et al. |
| 6,296,490 B1 | 10/2001 | Bowden |
| 6,312,399 B1 | 11/2001 | Lurie et al. |
| 6,334,441 B1 | 1/2002 | Zowtiak et al. |
| 6,356,785 B1 | 3/2002 | Snyder et al. |
| 6,369,114 B1 | 4/2002 | Weil et al. |
| 6,374,827 B1 | 4/2002 | Bowden et al. |
| 6,390,996 B1 | 5/2002 | Halperin et al. |
| 6,425,393 B1 | 7/2002 | Lurie et al. |

(56) References Cited

U.S. PATENT DOCUMENTS

| | | |
|---|---|---|
| 6,439,228 B1 | 8/2002 | Hete et al. |
| 6,459,933 B1 | 10/2002 | Lurie et al. |
| 6,463,327 B1 | 10/2002 | Lurie et al. |
| 6,486,206 B1 | 11/2002 | Lurie |
| 6,526,970 B2 | 3/2003 | DeVries et al. |
| 6,526,973 B1 | 3/2003 | Lurie et al. |
| 6,536,432 B2 | 3/2003 | Truschel |
| 6,544,172 B2 | 4/2003 | Toeppen-Sprigg |
| 6,555,057 B1 | 4/2003 | Barbut et al. |
| 6,578,574 B1 | 6/2003 | Kohnke |
| 6,584,973 B1 | 7/2003 | Biondi et al. |
| 6,587,726 B2 | 7/2003 | Lurie et al. |
| 6,595,213 B2 | 7/2003 | Bennarsten |
| 6,604,523 B2 | 8/2003 | Lurie et al. |
| 6,622,274 B1 | 9/2003 | Lee et al. |
| 6,622,724 B1 | 9/2003 | Truitt et al. |
| 6,631,716 B1 | 10/2003 | Robinson et al. |
| 6,656,166 B2 | 12/2003 | Lurie et al. |
| 6,662,032 B1 | 12/2003 | Gavish et al. |
| 6,662,724 B2 | 12/2003 | Reinhard et al. |
| 6,676,613 B2 | 1/2004 | Cantrell et al. |
| 6,726,634 B2 | 4/2004 | Freeman |
| 6,729,334 B1 | 5/2004 | Baran |
| 6,758,217 B1 | 7/2004 | Younes |
| 6,776,156 B2 | 8/2004 | Lurie et al. |
| 6,780,017 B2 | 8/2004 | Pastrick et al. |
| 6,792,947 B1 | 9/2004 | Bowden |
| 6,863,656 B2 | 3/2005 | Lurie |
| 6,877,511 B2 | 4/2005 | DeVries et al. |
| 6,935,336 B2 | 8/2005 | Lurie et al. |
| 6,938,618 B2 | 9/2005 | Lurie et al. |
| 6,986,349 B2 | 1/2006 | Lurie |
| 6,988,499 B2 | 1/2006 | Holt et al. |
| 7,011,622 B2 | 3/2006 | Kuyava et al. |
| 7,032,596 B2 | 4/2006 | Thompson et al. |
| 7,044,128 B2 | 5/2006 | Lurie et al. |
| 7,066,173 B2 | 6/2006 | Banner et al. |
| 7,082,945 B2 | 8/2006 | Lurie |
| 7,096,866 B2 | 8/2006 | Be'eri et al. |
| 7,117,438 B2 | 10/2006 | Wallace et al. |
| 7,174,891 B2 | 2/2007 | Lurie et al. |
| 7,185,649 B2 | 3/2007 | Lurie |
| 7,188,622 B2 | 3/2007 | Martin et al. |
| 7,195,012 B2 | 3/2007 | Lurie |
| 7,195,013 B2 | 3/2007 | Lurie |
| 7,204,251 B2 | 4/2007 | Lurie |
| 7,210,480 B2 | 5/2007 | Lurie et al. |
| 7,220,235 B2 | 5/2007 | Geheb et al. |
| 7,226,427 B2 | 6/2007 | Steen |
| 7,275,542 B2 | 10/2007 | Lurie et al. |
| 7,311,668 B2 | 12/2007 | Lurie |
| 7,448,381 B2 | 11/2008 | Sasaki et al. |
| 7,469,700 B2 | 12/2008 | Baran |
| 7,487,773 B2 | 2/2009 | Li |
| 7,500,481 B2 | 3/2009 | Delache et al. |
| 7,594,508 B2 | 9/2009 | Doyle |
| 7,650,181 B2 | 1/2010 | Freeman et al. |
| 7,682,312 B2 | 3/2010 | Lurie |
| 7,766,011 B2 | 8/2010 | Lurie |
| 7,793,659 B2 | 9/2010 | Breen |
| 7,824,436 B2 | 11/2010 | Barbut et al. |
| 7,836,881 B2 | 11/2010 | Lurie et al. |
| 7,899,526 B2 | 3/2011 | Benditt et al. |
| 8,011,367 B2 | 9/2011 | Lurie et al. |
| 8,072,415 B2 | 12/2011 | Fukuhara |
| 8,108,204 B2 | 1/2012 | Gabrilovich et al. |
| 8,151,790 B2 | 4/2012 | Lurie et al. |
| 8,210,176 B2 | 7/2012 | Metzger et al. |
| 8,287,474 B1 | 10/2012 | Koenig et al. |
| 8,388,682 B2 | 3/2013 | Hendricksen et al. |
| 8,408,204 B2 | 4/2013 | Lurie |
| 8,702,633 B2 | 4/2014 | Voss et al. |
| 8,755,902 B2 | 6/2014 | Lurie et al. |
| 8,939,922 B2 | 1/2015 | Strand et al. |
| 9,180,266 B1* | 11/2015 | Sherman ............ A61M 16/0003 |
| 9,238,115 B2 | 1/2016 | Marshall et al. |
| 2001/0003984 A1 | 6/2001 | Bennarsten et al. |
| 2001/0029339 A1 | 10/2001 | Orr et al. |
| 2001/0047140 A1 | 11/2001 | Freeman |
| 2002/0007832 A1 | 1/2002 | Doherty |
| 2002/0069878 A1 | 6/2002 | Lurie et al. |
| 2002/0104544 A1 | 8/2002 | Ogushi et al. |
| 2002/0170562 A1 | 11/2002 | Lurie et al. |
| 2002/0179090 A1 | 12/2002 | Boussignac |
| 2003/0000526 A1 | 1/2003 | Gobel |
| 2003/0037782 A1 | 2/2003 | Yeung |
| 2003/0037784 A1 | 2/2003 | Lurie |
| 2003/0062040 A1 | 4/2003 | Lurie et al. |
| 2003/0062041 A1 | 4/2003 | Keith et al. |
| 2003/0144699 A1 | 7/2003 | Freeman |
| 2003/0192547 A1 | 10/2003 | Lurie et al. |
| 2004/0016428 A9 | 1/2004 | Lurie |
| 2004/0058305 A1 | 3/2004 | Lurie et al. |
| 2004/0097821 A1 | 5/2004 | Blomberg et al. |
| 2004/0200473 A1 | 10/2004 | Lurie et al. |
| 2004/0200474 A1 | 10/2004 | Lurie |
| 2004/0210281 A1 | 10/2004 | Dzeng et al. |
| 2004/0211415 A1 | 10/2004 | Lurie |
| 2004/0211416 A1 | 10/2004 | Lurie |
| 2004/0211417 A1 | 10/2004 | Lurie |
| 2004/0231664 A1 | 11/2004 | Lurie et al. |
| 2004/0267325 A1 | 12/2004 | Geheb et al. |
| 2005/0016534 A1 | 1/2005 | Ost |
| 2005/0075531 A1 | 4/2005 | Loeb et al. |
| 2005/0126567 A1 | 6/2005 | Lurie |
| 2005/0165334 A1 | 7/2005 | Lurie |
| 2005/0199237 A1 | 9/2005 | Lurie |
| 2005/0217677 A1 | 10/2005 | Lurie et al. |
| 2005/0267381 A1 | 12/2005 | Benditt et al. |
| 2006/0089574 A1 | 4/2006 | Paradis |
| 2006/0129191 A1 | 6/2006 | Sullivan et al. |
| 2006/0270952 A1 | 11/2006 | Freeman et al. |
| 2007/0000494 A1 | 1/2007 | Banner et al. |
| 2007/0017523 A1 | 1/2007 | Be-Eri et al. |
| 2007/0021683 A1 | 1/2007 | Benditt et al. |
| 2007/0023045 A1* | 2/2007 | Kwok ............... A61M 16/0057 128/204.23 |
| 2007/0060785 A1 | 3/2007 | Freeman et al. |
| 2007/0083677 A1 | 4/2007 | Cecka et al. |
| 2007/0221222 A1 | 9/2007 | Lurie |
| 2007/0277826 A1 | 12/2007 | Lurie |
| 2008/0039748 A1 | 2/2008 | Palmer et al. |
| 2008/0047555 A1 | 2/2008 | Lurie et al. |
| 2008/0053445 A1 | 3/2008 | Kroupa et al. |
| 2008/0072896 A1 | 3/2008 | Setzer et al. |
| 2008/0072902 A1* | 3/2008 | Setzer ................. A61M 16/024 128/204.21 |
| 2008/0078390 A1 | 4/2008 | Milne et al. |
| 2008/0092891 A1 | 4/2008 | Cewers |
| 2008/0097258 A1 | 4/2008 | Walker |
| 2008/0097385 A1 | 4/2008 | Vinten-Johansen et al. |
| 2008/0108905 A1 | 5/2008 | Lurie |
| 2008/0255482 A1 | 10/2008 | Lurie |
| 2008/0257344 A1 | 10/2008 | Lurie et al. |
| 2008/0302363 A1 | 12/2008 | Kroupa |
| 2009/0020128 A1 | 1/2009 | Metzger et al. |
| 2009/0062701 A1 | 3/2009 | Yannopoulos et al. |
| 2009/0076573 A1 | 3/2009 | Burnett et al. |
| 2009/0080153 A1* | 3/2009 | Richardson .......... A45C 13/002 361/679.56 |
| 2009/0126731 A1 | 5/2009 | Dunsmore et al. |
| 2009/0164000 A1 | 6/2009 | Shirley |
| 2009/0197739 A1 | 8/2009 | Hashimoto |
| 2009/0277447 A1 | 11/2009 | Voss et al. |
| 2009/0299156 A1 | 12/2009 | Simpson et al. |
| 2010/0000535 A1 | 1/2010 | Wickham et al. |
| 2010/0147302 A1 | 6/2010 | Selvarajan et al. |
| 2010/0174278 A1 | 7/2010 | Barbut et al. |
| 2010/0179442 A1 | 7/2010 | Lurie |
| 2010/0186745 A1 | 7/2010 | Mashak |
| 2010/0229867 A1* | 9/2010 | Bertinetti .............. A61M 16/16 128/205.25 |
| 2010/0247682 A1 | 9/2010 | Gladwin et al. |
| 2010/0319691 A1 | 12/2010 | Lurie et al. |

(56) References Cited

U.S. PATENT DOCUMENTS

| | | |
|---|---|---|
| 2011/0056491 A1 | 3/2011 | Rumph et al. |
| 2011/0098612 A1 | 4/2011 | Lurie |
| 2011/0160782 A1 | 6/2011 | Lurie et al. |
| 2011/0201979 A1 | 8/2011 | Voss et al. |
| 2011/0297147 A1 | 12/2011 | Lick et al. |
| 2012/0016279 A1 | 1/2012 | Banville et al. |
| 2012/0203147 A1 | 8/2012 | Lurie et al. |
| 2012/0302908 A1 | 11/2012 | Hemnes et al. |
| 2012/0330199 A1 | 12/2012 | Lurie et al. |
| 2012/0330200 A1 | 12/2012 | Voss et al. |
| 2013/0118498 A1 | 5/2013 | Robitaille et al. |
| 2013/0172768 A1 | 7/2013 | Lehman |
| 2013/0231593 A1 | 9/2013 | Yannopoulos et al. |
| 2013/0269701 A1 | 10/2013 | Lurie |
| 2014/0005566 A1 | 1/2014 | Homuth et al. |
| 2014/0048061 A1 | 2/2014 | Yannopoulos et al. |
| 2016/0287834 A1 | 10/2016 | Bennett |

FOREIGN PATENT DOCUMENTS

| | | |
|---|---|---|
| AU | 687942 B | 5/1995 |
| CA | 668771 A | 8/1963 |
| CA | 2077608 A1 | 3/1993 |
| CA | 2214887 A1 | 9/1996 |
| CN | 1183731 A | 6/1998 |
| CN | 2724738 Y | 9/2005 |
| DE | 2453490 A1 | 5/1975 |
| DE | 4308493 A1 | 9/1994 |
| EP | 0029352 A1 | 5/1981 |
| EP | 0139363 A1 | 5/1985 |
| EP | 0245142 A1 | 11/1987 |
| EP | 0367285 A2 | 5/1990 |
| EP | 0411714 A1 | 2/1991 |
| EP | 0509773 A1 | 10/1992 |
| EP | 0560440 A1 | 9/1993 |
| EP | 0623033 A1 | 11/1994 |
| GB | 1344862 A | 1/1974 |
| GB | 1465127 A | 2/1977 |
| GB | 2117250 A | 10/1983 |
| GB | 2139099 A | 11/1984 |
| JP | 2005000675 A | 1/2005 |
| JP | 2006524543 A | 11/2006 |
| JP | 2007504859 A | 3/2007 |
| WO | 9005518 A1 | 5/1990 |
| WO | 9302439 A1 | 2/1993 |
| WO | 9321982 A1 | 11/1993 |
| WO | 9426229 A1 | 11/1994 |
| WO | 9513108 A1 | 5/1995 |
| WO | 9528193 A1 | 10/1995 |
| WO | 9628215 A1 | 9/1996 |
| WO | 9706843 A1 | 2/1997 |
| WO | 9820938 A1 | 5/1998 |
| WO | 9947197 A1 | 9/1999 |
| WO | 9963926 A2 | 12/1999 |
| WO | 0020061 A1 | 4/2000 |
| WO | 0102049 A2 | 1/2001 |
| WO | 0170092 A2 | 9/2001 |
| WO | 0170332 A2 | 9/2001 |
| WO | 02092169 A1 | 11/2002 |
| WO | 2004096109 A2 | 11/2004 |
| WO | 2006088373 A1 | 8/2006 |
| WO | 2008147229 A1 | 12/2008 |
| WO | 2009059359 A1 | 5/2009 |
| WO | 2010044034 A1 | 4/2010 |
| WO | 2013064888 A1 | 5/2013 |
| WO | 2013096495 A1 | 6/2013 |
| WO | 2014026193 A1 | 2/2014 |

OTHER PUBLICATIONS

Search Report of AU 2008243018; dated Sep. 18, 2012; 3 pgs.

Segal et al., "Ischemic postconditioning at the initiation of cardiopulmonary resuscitation facilitates cardiac and cerebral recovery after prolonged untreated ventricular fibrillation," Resuscitation, 2012, pp. 1-7.

Shapiro et al., "Neurosurgical Anesthesia and Intracranial Hypertension," Anesthesia, 3rd Edition, 1990, Church Livingston, New York, Chapter 54.

Steen et al., "The critical importance of minimal delay between chest compressions and subsequent defibrillation: a haemodynamic explanation", Resuscitation, 2003, pp. 249-258, vol. 58.

Supplementary Partial European Search Report for European Patent Application 04760311 dated Mar. 21, 2011, 1 pg.

Yannopoulos et al., "Intrathoracic Pressure Regulator During Continuous-Chest-Compression Advanced Cardiac Resuscitation Improves Vital Organ Perfusion Pressures in a Porcine Model of Cardiac Arrest", Circulation, 2005, pp. 803-811.

Yannopoulos et al., "Intrathoracic pressure regulation improves vital organ perfusion pressures in normovolemic and hypovolemic pigs," Resuscitation, 2006, pp. 445-453, vol. 70.

Yannopoulos et al., "Intrathoracic Pressure Regulation Improves 24-Hour Survival in a Porcine Model of Hypovolemic Shock," Anesthesia & Analgesia, ITPR and Survival in Hypovolemic Shock, 2007, pp. 157-162, vol. 104:1.

Yannopoulos et al., "Sodium nitroprusside enhanced cardiopulmonary resuscitation improves survival with good neurological function in a porcine model of prolonged cardiac arrest," Critical Care Medicine, 2011, pp. 1-6, vol. 39:6.

Yannopoulos et al., "Controlled pauses at the initiation of sodium nitroprussdi e-enhanced cardiopulmonary resuscitation facilitate neurological and cardiac recovery after 15 minutes of untreated ventricular fibrillation," Critical Care Medicine, 2012, pp. 1-8, vol. 40:5.

Yu et al., "Adverse outcomes of interrupted precordial compression during automated defibrillation", Circulation, 2002, pp. 368-372, vol. 106.

Zhao et al., "Inhibition of myocardial injury by ischemic postconditioning during reperfusion: comparison with ischemic preconditioning," AJP Heart Circ Physiol, 2003, pp. H579-H588, vol. 285.

Zoll Autopulse Non-Invasive Cardiac Support Pump, obtained online on 715106 at http://www.zoll.com/product.aspx?id=84, 1 page.

Advanced Circulatory Systems,Inc. (2005). Introducing ResQPOD® (#49-0324-000, 01) [Brochure). Roseville, MN: Advanced Circulatory Systems,Inc., 2 pages.

Advanced Circulatory Systems, Inc. (2006). ResQPOD® Circulatory Enhancer: Strengthening the Chain of Survival (#49-0336-000, 01) [Brochure). Roseville, MN: Advanced Circulatory Systems, Inc. 2 pages.

Advanced Circulatory Systems, Inc. (2006). ResQPOD® Circulatory Enhancer: Strengthening the Chain of Survival (#49-0336-000, 02). [Brochure). Roseville, MN: Advanced Circulatory Systems, Inc., 2 pages.

Advanced Circulatory Systems,Inc. (2009). ResQPOD® Perfusion on Demand: ResQPOD Impedance Threshold Device (#49-0324-001, 02) [Brochure). Roseville, MN: Advanced Circulatory Systems, Inc., 2 pages.

Advanced Circulatory Systems, Inc. (2010), ResQPOD Impedance Threshold Device 10.0: Strengthening the Chain of Survival (#49-0336000, 03) [Brochure], Roseville, MN: Advanced Circulatory Systems, Inc. 2 pages.

Advanced Circulatory Systems, Inc. (2010), ResQPOD Impedance Threshold Device: Strengthening the Chain of Survival (#49-0336000, 04) [Brochure], Roseville, MN: Advanced Circulatory Systems, Inc. 2 pages.

Advanced Circulatory Systems, Inc. (2010), ResQPOD Impedance Threshold Device: Strengthening the Chain of Survival (#49-0336000, 05) [Brochure], Roseville, MN: Advanced Circulatory Systems, Inc. 2 pages.

Advanced Circulatory Systems, Inc. (2010). ResQPOD® Perfusion on Demand: ResQPOD Impedance Threshold Device (#49-0324-001, 03) [Brochure). Roseville, MN: Advanced Circulatory Systems,Inc., 2 pages.

(56) References Cited

OTHER PUBLICATIONS

Advanced Circulatory Systems, Inc. (2011). ResQPOD® Perfusion on Demand: ResQPOD Impedance Threshold Device (#49-0324-001, 04) [Brochure]. Roseville, MN: Advanced Circulatory Systems, Inc. 2 pages.
Advanced Circulatory Systems. Inc. (2011). ResQPOD® Perfusion on Demand: ResQPOD Impedance Threshold Device (#49-0324-001, 05) [Brochure]. Roseville, MN: Advanced Circulatory Systems, Inc., 2 pages.
Advanced Circulatory Systems, Inc. (2011), ResQPOD ITD: Strengthening the Chain of Survival (#49-0336000, 06) [Brochure], Roseville, MN: Advanced Circulatory Systems, Inc. 2 pages.
Advanced Circulatory Systems, Inc. (Aug. 2011), Early Intervention is Life-Saving in Cardiac Arrest (#49-0864-000, 01) [Brochure], Roseville, MN: Advanced Circulatory Systems, Inc. 2 pages.
Advanced Circulatory Systems, Inc. (Aug. 2011), Early Intervention is Life-Saving in Cardiac Arrest (#49-0864-000, 02) [Brochure], Roseville, MN: Advanced Circulatory Systems, Inc. 2 pages.
Advanced Circulatory Systems, Inc. (Jan. 2012), Benefits of the ResQPOD Based Upon the ROC PRIMED Study (#49 0864 000, 03) [Brochure], Roseville, MN: Advanced Circulatory Systems, Inc. 2 pages.
Advanced Circulatory Systems, Inc. (Mar. 2012), Benefits of the ResQPOD Based Upon the ROC PRIMED Study (#49 0864 000, 04) [Brochure], Roseville, MN: Advanced Circulatory Systems, Inc. 2 pages.
Advanced Circulatory Systems, Inc. (2013), ResQPOD More than a Heartbeat (#49-0336-000, 08) [Brochure], Roseville, MN: Advanced Circulatory Systems, Inc. 2 pages.
Advanced Circulatory Systems, Inc. (Jan. 2013), Emerging Data: The Resuscitation Outcomes Consortium (ROC) PRIMED Study on the Efficacy of the ITD (#49-0864-000, 05) [Brochure], Roseville, MN: Advanced Circulatory Systems, Inc. 2 pages.
Advanced Circulatory Systems, Inc. (Jan. 2014), Emerging Data: The Resuscitation Outcomes Consortium (ROC) PRIMED Study on the Efficacy of the ITD (#49-0864-000, 06) [Brochure], Roseville, MN: Advanced Circulatory Systems, Inc. 2 pages.
Ambu InternationalNS "Directions for use of Ambu® CardioPump™",- Sep. 1992, 8 pages.
Aufderheide et al., "Hyperventilation-Induced Hypotension During Cardiopulmonary Resuscitation," Circulation; 2004, pp. 1960-1965, vol. 109:16.
Aufderheide et al., "Standard cardiopulmonary resuscitation versus active compression-decompression cardiopulmonary resuscitation with augmentation of negative intrathoracic pressure for out-of-hospital cardiac arrest: A randomized trial," 2011, Lancet, pp. 301-311, vol. 377.
Azim et al., "Case Report The use of bispectral index during a cardiopulmonary arrest: a potential predictor of cerebral perfusion", Anesthesia, 2009, pp. 610-612, vol. 59.
Babbs, "CPR Techniques that Combine Chest and Abdominal Compression and Decompression: Hemodynamic Insights from a Spreadsheet Model," Circulation, 1999, pp. 2146-2152.
Christenson et al., "Abdominal Compressions During CPR: Hemodynamic Effects of Altering Timing and Force", The Journal of Emergency Medicine, 1992, pp. 257-266, vol. 10.
Cohen et al., "Active compression-decompression resuscitation: A novel method of cardiopulmonary resuscitation," American Heart Journal, pp. 1145-1150, vol. 124:5.
Cohen et al., "Active Compression-Decompression: A New Method of Cardiopulmonary Resuscitation," 1992, JAMA, pp. 2916-2923, vol. 267:29.
Dupuis, "Ventilators—Theory and Clinical Application," Jan. 1986, The C.V. Mosby Company, pp. 447-448, 481, 496.

Edelson et al., "Effects of compression depth and pre-shock pauses predict defibrillation failure during cardiac arrest," Resuscitation, 2006, pp. 137-145, vol. 71.
Geddes et al., "Electrically Produced Artificial Ventilation," Medical Instrumentation, 1988, pp. 263-271, vol. 22:5.
Geddes et al., "Optimum Stimulus Frequency for Contracting the Inspiratory Muscles with Chest-Surface Electrodes to Produce Artificial respiration," Annals of Biomedical Engineering, 1990, pp. 103-108, vol. 18.
Geddes et al., "Inspiration Produced by Bilateral Electromagnetic, Cervical Phrenic Nerve Stimulation in Man," IEEE Transactions on Biomedical Engineering, 1991, pp. 1047-1048, vol. 38:9.
Geddes, "Electroventilation—A Missed Opportunity?" Biomedical Instrumentation & Technology, 1998, pp. 401-414.
Glenn et al., "Diaphragm Pacing by Electrical Stimulation of the Phrenic Nerve," Neurosurgery, 1985, pp. 974-984, vol. 17:6.
Glenn et al., "Twenty Years of Experience in Phrenic Nerve Stimulation to Pace the Diaphragm," Nov./Dec. 1986, Part I, Pace 9, pp. 780-784.
Guidelines for Cardiopulmonary Resuscitation and Emergency Cardiac Care, JAMA, 1992, pp. 2172-2177, vol. 268.
International Search Report and Written Opinion of PCT/US2004/027772 dated Mar. 11, 2005, 5 pages.
International Search Report and Written Opinion of PCT/US08/60367 dated Sep. 23, 2006.
International Search Report and Written Opinion of PCT/US2012/070700 dated May 20, 2013, 15 pages.
International Search Report and Written Opinion dated Jul. 9, 2014 for International Patent Application No. PCT/US2014/22725 filed Mar. 10, 2014, 24 pages.
Johnson et al., "Time to Throw Away Your Stethoscope? Capnography: Evidence-Based Patient Monitoring Technology", Journal of Radiology Nursing, 2011, pp. 25-34, vol. 30:1.
Jung et al., "Usefulness of the bispectral index during cardiopulmonary resuscitation—A case report-", Korean J Anesthesiol, 2013, pp. 69-72, vol. 64:1.
Kotze et al., "Diaphragm pacing in the treatment of ventilatory failure," SAMT, 1995, pp. 223-224, vol. 68.
Laghi et al., "Comparison of Magnetic and Electrical Phrenic Nerve Stimulation in assessment of Diaphragmantic Contractility," American Physiological Society, 1996, pp. 1731-1742.
Lindner et al., "Effects of Active Compression-Decompression Resuscitation on Myocardialand Cerebral Blood Flow in Pigs," Circulation, 1993, pp. 1254-1263, vol. 88:3.
Lurie et al., "Regulated to Death: The Matter of Informed Consent for Human Experimentation in Emergency Resuscitation Research," PACE, 1995, pp. 1443-1447, vol. 8.
Lurie et al., "Comparison of a 10-Breaths-Per-Minute Versus a 2-Breaths-Per-Minute Strategy During Cardiopulmonary Resuscitation in a Porcine Model of Cardiac Arrest," Respiratory Care, 2008, pp. 862-870, vol. 53:7.
Michigan Instruments, Inc. Thumper 1007CC Continuous Compression Cardiopulmonary Resuscitation System, obtained online 715/2006 at http://www.michiganinstruments.com/resus-thumper.htm, 1 page.
Mushin et al., "Automatic Ventilation of the Lungs—The Lewis-Leigh Inflating Valve," 1969, Blackwell Scientific, Oxford, GB, p. 838.
Sato et al., "Adverse effects of interrupting precordial compression during cardiopulmonary resuscitation," Crit. Care Med, 1997, pp. 733-736, vol. 25:5.
Schultz et al., "Sodium nitroprusside enhanced cardiopulmonary resuscitation (SNPeCPR) improves vital organ perfusion pressures and carotid blood flow in a porcine model of cardiac arrest," Resuscitation, 2012, pp. 374-377, vol. 83.

* cited by examiner

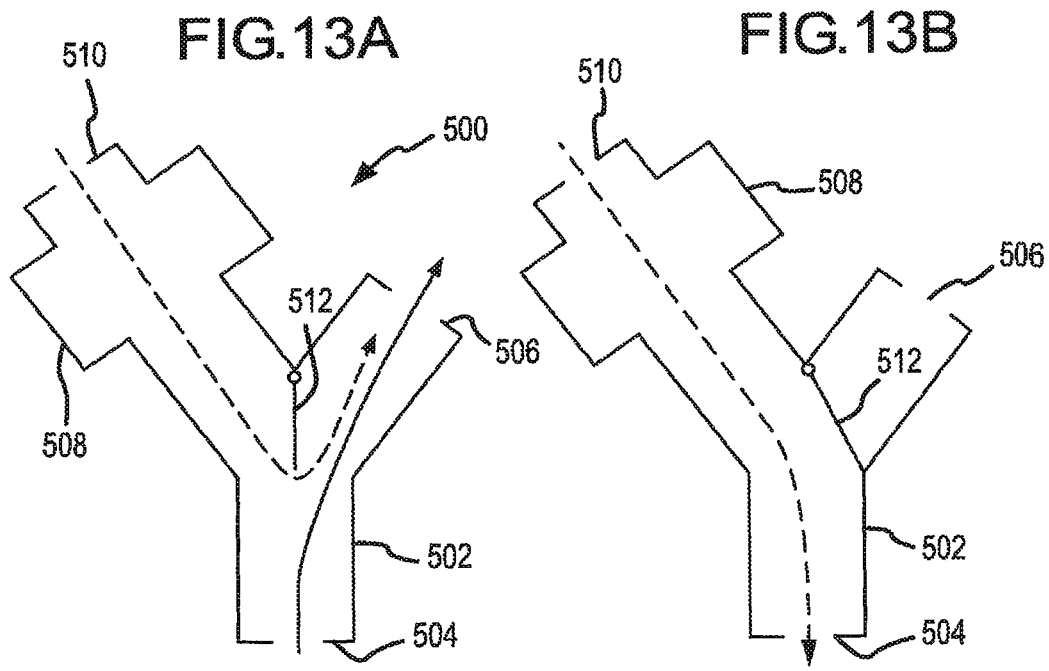
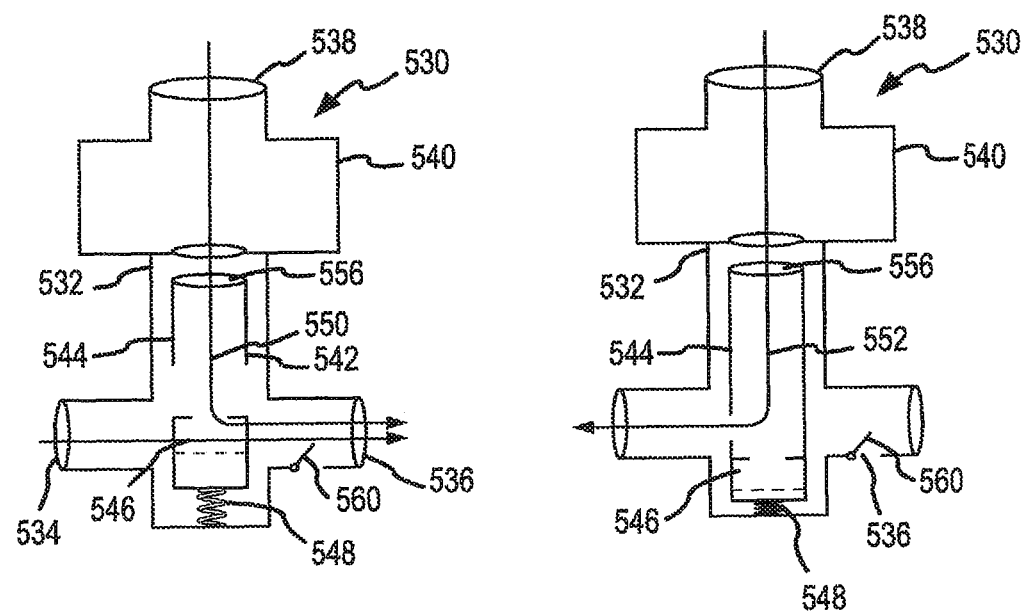

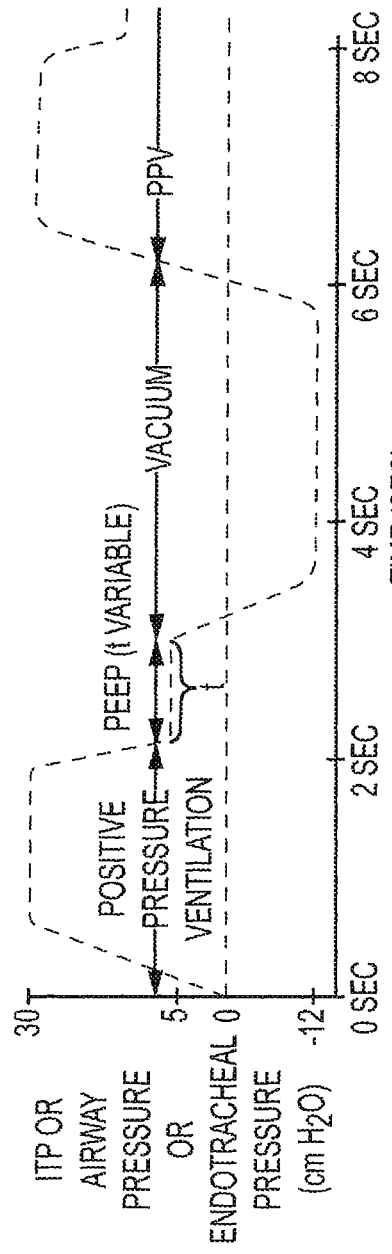
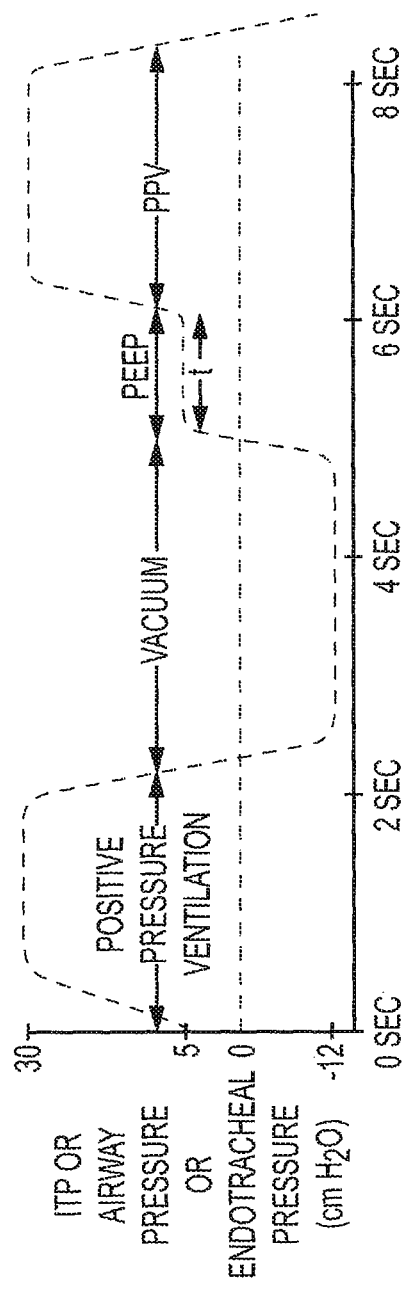
FIG. 16A
FIG. 16B

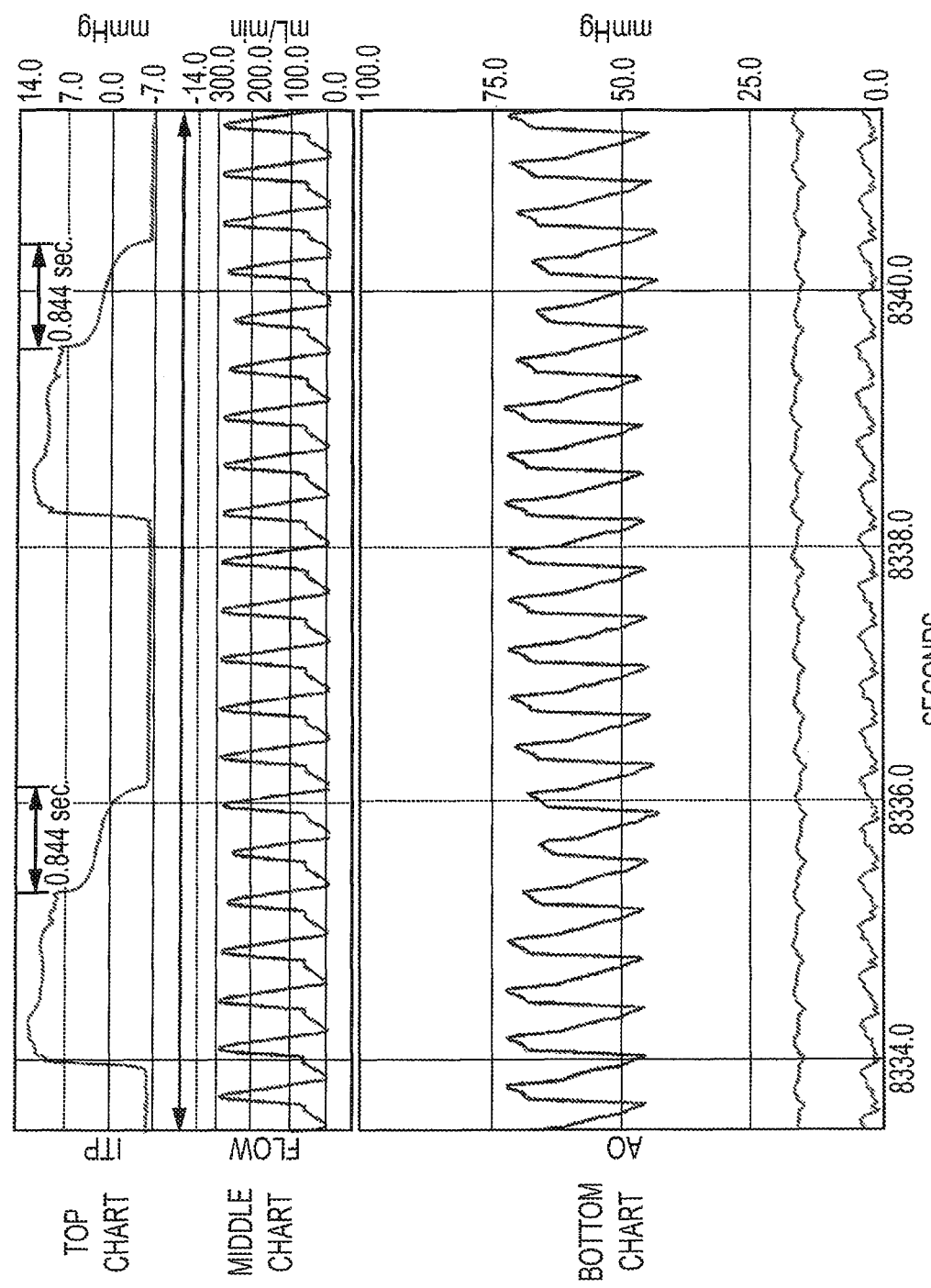

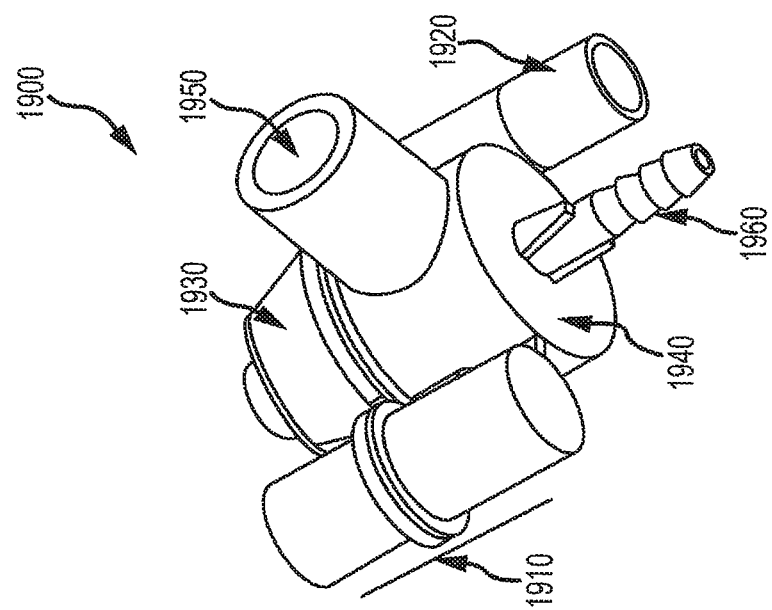
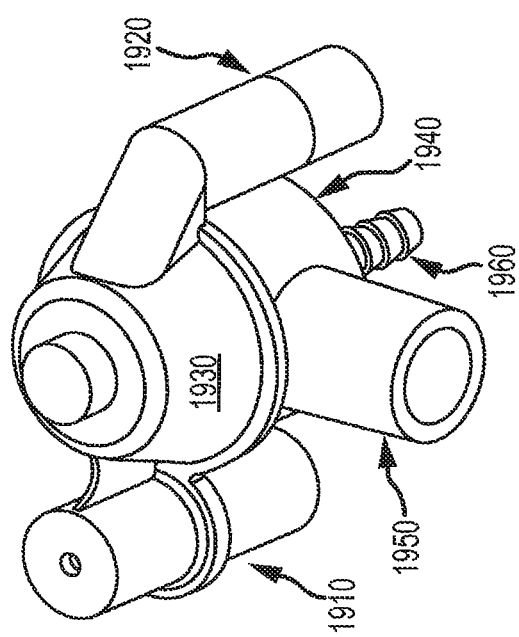
FIG.19A-2
FIG.19A-1

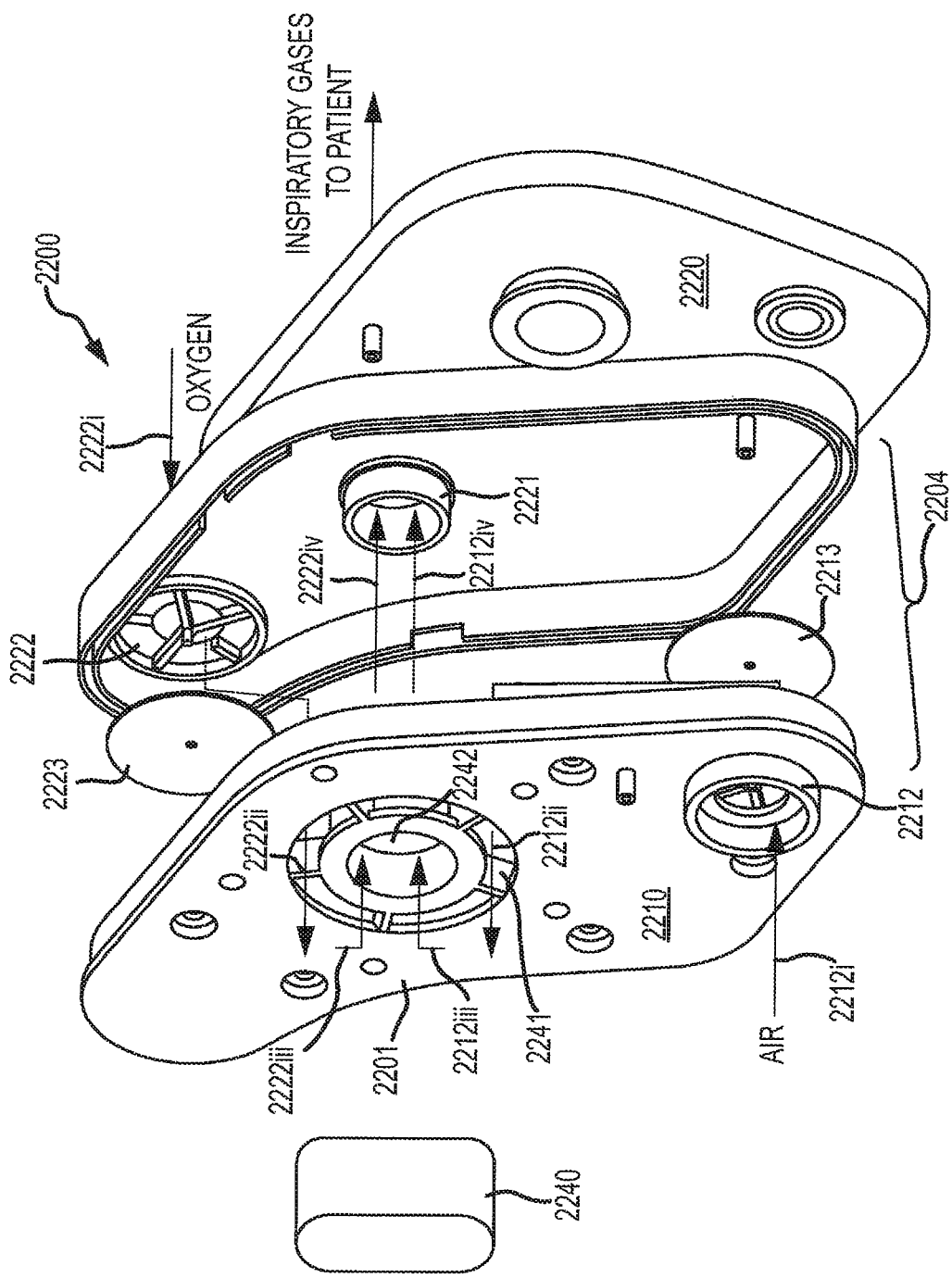

VACUUM AND POSITIVE PRESSURE VENTILATION SYSTEMS AND METHODS FOR INTRATHORACIC PRESSURE REGULATION

CROSS-REFERENCES TO RELATED APPLICATIONS

This application is a continuation of U.S. patent application Ser. No. 14/602,057, filed Jan. 21, 2015, which is a continuation of U.S. patent application Ser. No. 12/819,959 filed Jun. 21, 2010 (U.S. Pat. No. 8,967,144), which is a nonprovisional of, and claims the benefit of the filing date of U.S. Provisional Patent Application No. 61/218,763 filed Jun. 19, 2009. This application is also related to U.S. patent application Ser. No. 11/034,996 filed Jan. 12, 2005, which is a continuation in part of U.S. patent application Ser. No. 10/796,875 filed Mar. 8, 2004 and a continuation in part of U.S. patent application Ser. No. 10/660,462 filed Sep. 1, 2003 (U.S. Pat. No. 7,082,945), which is a continuation in part of U.S. patent application Ser. No. 10/460,558 filed Jun. 11, 2003 (U.S. Pat. No. 7,185,649), which is a continuation in part of U.S. patent application Ser. No. 10/426,161 filed Apr. 28, 2003 (U.S. Pat. No. 7,195,012). This application is also related to U.S. Pat. Nos. 5,730,122, 6,029,667, and 7,195,013). The entire content of each of the above listed filings is incorporated herein by reference for all purposes.

BACKGROUND OF THE INVENTION

Embodiments of the present invention relate generally to the field of systemic, and intracranial pressures. More specifically, embodiments relate to devices and methods for decreasing intracranial pressures and increasing systemic arterial pressures and systemic vital organ perfusion, such as those resulting from a traumatic head injury, blood loss, and other injuries and illnesses or interventions (e.g. surgery and anesthesia) that cause low blood pressure and poor circulation. Embodiments provides a means to maintain adequate blood pressure and ventilation in a patient who has low blood pressure and is unable to breathe independently in order to maintain vital organ perfusion and oxygenation.

Decreased organ perfusion results in cell death. Both low systemic pressures, or in the case of the brain, high intracranial pressures reduce vital organ perfusion. Hence, head trauma and shock are generally regarded as the leading cause of morbidity and mortality in the United States for children and young adults. Head trauma often results in swelling of the brain. Because the skull cannot expand, the increased pressures within the brain can lead to death or serious brain injury. While a number of therapies have been evaluated in order to reduce brain swelling, including use of hyperventilation and steroids, an effective way to treat intracranial pressures or improve cerebral perfusion pressures remains an important medical challenge. Similarly, low blood pressure and multi-organ injury and disease decrease vital organ perfusion and when associated with head trauma there is an increase in pressure within the brain and a subsequent decrease in cerebral blood flow. These patients have an extremely high mortality rate and similarly remain a major medical challenge.

BRIEF SUMMARY OF THE INVENTION

Embodiments of the present invention encompass techniques for regulating intrathoracic pressure, airway pressure, endotracheal pressure, and the volume of respiratory gases within the lungs. Advantageously, certain approaches involve decreasing intracranial or intraocular and increasing systemic pressures when the thorax is intact. Similar embodiments of the present invention can also be used in a patient with the open chest. Lung volume and pressure may change, however the intrathoracic pressure may remain unchanged as the circuit is open. In some cases, a positive end expiratory pressure (PEEP) can be provided prior to application of a vacuum. In some cases, a PEEP can be provided subsequent to application of a vacuum. The addition of PEEP may provide additional oxygenation and protection for a diseased or compromised lung, more than just the positive pressure breath would. In some cases, the use of intrathoracic pressure regulation (IPR) can modulate the autonomic nervous system as well as alter cerebral and systemic circulation. And in some cases, the combination of IPR and an intra-aortic balloon pump (IABP) can provide an even bigger effect on enhancing circulation than either provides alone. In some cases, when IPR therapy is applied when the thorax has been opened, for example during open heart surgery, the lungs are filled with respiratory gases during the positive pressure phase (inspiration) and during the expiratory phase respiratory gases are actively extracted from the lungs. This results in the rapid displacement of blood within the lungs into the left atrium, thereby priming the left heart with blood. By alternately filling the lungs with respiratory gases and providing space concurrently for blood from the right heart, and then extracting respiratory gases and propelling the blood within the lung reservoir forward, the lung serves as a peristaltic sponge to both suck up blood from the right heart and venous circulation and deliver it to the left heart. By 'wringing out the sponge' the expansion and contraction of the lung parenchyma provides a novel means to propel blood forward in the setting of low or reduced blood circulation. The addition of PEEP either before or after this 'wringing out' process provides a means to help maintain oxygenation and preserve and protect lung function. During this process the delivered tidal volume during the inspiratory phase may vary and the rate of respiratory gases removal by the method or device may vary, either directly or indirectly with the tidal volume delivered, thereby providing a means to achieve the desired target airway pressures and/or intrathoracic pressures. This method and devices that provide IPR therapy can therefore be used to enhance circulation and increase blood pressure, even when the thorax is open to atmospheric pressure such as during or after open heart surgery. It can be applied to both lungs or just one lung, as long as the method and device is allowed to move respiratory gases in and out of the lung(s).

The changes in pressures in the lung achieved with IPR therapy are a direct result of changes in lung respiratory gas volume. With each positive pressure ventilation the gas volume is increased and when it is actively extracted it is reduced. In the process blood is squeezed out of the lungs and blood can only move forward due to the intact one-way valves within the heart (pulmonic and mitral in this case). Thus blood is pumped out of the lungs, which served as a giant reservoir, during the gas extraction phase and when the lungs are inflated respiratory gases fill the alveoli of the lungs and indirectly restore the arterial and venous bed architecture so that blood from the right heart rushes into the lung blood reservoir as soon as the lungs are inflated. The active infusion and removal of respiratory gases by the IPR therapy provides a novel means to pump blood into the left heart. It is important to note that when the chest is open to atmospheric pressure, then changes in lung volumes typically do not alter intracranial pressures as the pressures within the non-lung structures in the thorax no longer vary with changes in airway or lung pressures.

In one embodiment, the invention provides a device for decreasing intracranial or intraocular pressures and increasing systemic blood pressures and organ perfusion when the thorax is intact. The device comprises a housing having an inlet opening and an outlet opening that is adapted to be interfaced with a person's airway. The device further includes a valve system that is operable to regulate respiratory gas flows through the housing and into the person's lungs during spontaneous or artificial inspiration. For a person who requires artificial inspiration, the valve system can be attached to a vacuum source. The valve system assists in lowering airway pressures during spontaneous inspiration and in non-breathing patients when not actively delivering a breath to in turn lower intracranial pressures or intraocular pressures and increase systemic perfusion pressures. The valve system may also be used to continuously or intermittently lower pressures in the head by lowering the pressures within the thorax. In addition, the invention lowers the pressures within the left and right heart, when positive pressure ventilations are not being provided. The reduced pressures in the thorax, including the heart, draws more blood back to the heart thereby helping to increase the efficiency of heart function and cardiac output. The invention can therefore be used to treat patients suffering from a number of disease states including but not limited to those suffering from elevated intracranial pressures, intra-ocular pressures, shock, hypotension, circulatory collapse, cardiac arrest, heart failure, intra-operative hypotension, and those in dialysis. It can also lower venous pressures within the abdomen during surgical procedures such as operations on the liver or intestines, and simultaneously provide greater blood flow to these and other vital organs such as the kidneys, brain, and heart. By lowering venous pressures it can help to reduce blood loss during surgical procedures. By the aforementioned described mechanisms the novel methods and devices can also treat hypotension and poor circulation associated with sepsis, poly-traumatic organ damage, and acute respiratory disease syndrome (ARDS). The intention may also be used to reduce venous pressure in 'compartment syndrome' and therefore help to circulate more blood and preserve tissue viability and function. The invention is based upon the discovery that reductions in intrathoracic pressure result in a decrease in intracranial pressures and enhancement of blood flow to the heart. In patients with an open thorax, the device lowers pressure in the airway and in the lungs, thereby removing respiratory gases from the lungs. This results in a 'wringing out' of the lungs much like a wet sponge with each application of the vacuum and this forces the blood in the lungs into the left heart as the pulmonic valve prevent reverse transpulmonary flow. With the next inspiration, respiratory gases fill the lungs and blood rushes into the lungs. It is squeezed out with the next application of the low level vacuum. As such, the changes in airway pressure provide a pulmonary pump to alternatively squeeze blood out of the lungs and with each positive pressure breath provide an empty vascular reservoir within the lungs that is rapidly refilled from blood within the right heart.

Such a device may also be used to facilitate movement of cerebral spinal fluid when the thorax is intact. In so doing, intracranial pressures may be further reduced. Such a device may therefore be used to treat those suffering from head trauma associated with elevated intracranial pressures as well as those suffering from conditions that cause low systemic blood pressure.

In one aspect, the valve system is configured to open to permit respiratory gasses to freely flow to the person's lungs during spontaneous respirations when the negative intrathoracic pressure reaches a pressure in the range from about $-2$ cm $H_2O$ to about $-20$ cm $H_2O$ in order to reduce intrathoracic pressure and thus reduce intracranial or intraocular pressures. In this way, the negative intrathoracic pressure is lowered until a threshold pressure is reached, at which time the valve opens. The cycle may be repeated continuously or periodically to repetitively lower intrathoracic pressures. In another aspect, the valve system is configured to generate an intrathoracic vacuum in the range from about $-2$ cm $H_2O$ to about $-20$ cm $H_2O$ in order to both reduce intrathoracic pressure and thus reduce intracranial or intraocular pressures and to enhance blood flow to the heart. The device may include or be used with a means for repetitively compressing the chest to improve blood circulation in patents in or with low blood circulation or cardiac arrest. The compression could be accomplished with an automated chest compression, a circumferential vest, manual chest compression, and the like. This would improve blood flow to the heart and brain in patients with low blood circulation. When the device compresses the chest blood is forced out of the heart to increase perfusion of the vital organs. When the compression means is released, blood flows back into the heart. In some cases, a decompression device could also be used to actively lift or decompress the chest to enhance the blood flow back to the heart.

The device may also include means for causing the person to artificially inspire through the valve system. For example, the device may utilize an electrode, an iron lung cuirass device, a chest lifting device, a ventilator or the like. By reducing the pressure within the chest, respiratory gases flow into the lungs and provide oxygen. By sequentially compressing the chest and then decompressing the chest, the chest is turned into a bellows and blood is circulated and respiratory gases are exchanged. This action can be timed with the natural contractions of the heart, such as by using an ECG. In one embodiment, the chest is compressed and then the chest is allowed to recoil to its resting position to circulate blood and respiratory gases. After each chest wall recoil, a device is used to lower intrathoracic pressures to create an intrathoracic vacuum to enhance blood flow back to the heart. In another embodiment, the chest is compressed and then actively decompressed to circulate blood and respiratory gases, and after each chest decompression a device is used to lower intrathoracic pressures to create an intrathoracic vacuum to enhance blood flow back to the heart and also lower intracranial pressures. Devices that may be used to lower intrathoracic pressures include any type of vacuum or vacuum source, including those incorporated into a ventilator. During at least some of the decompressions, respiratory gases may be permitted to freely flow to the lungs to provide proper ventilation.

In another embodiment, the device may comprise a means to reduce intrathoracic pressure by applying a vacuum within the airway. The vacuum may be adjusted in terms of frequency, amplitude, and duration. When the thorax is intact this results in a decrease in intracranial pressure in proportion to the degree of vacuum applied. Hence, intracranial pressures may be reduced simply by manipulating airway pressures to reduce intrathoracic pressures. In addition, the vacuum created within the thorax enhances blood flow back to the heart, thereby simultaneously increasing cardiac output and systemic vital organ perfusion. Such a vacuum may be generated from an external vacuum source, through the airway or a chest tube between the ribs, or it may be generated using a ventilator capable of applying a negative pressure.

The device may further include a mechanism for varying the level of impedance or resistance of the valve system. It may include adding positive expiratory pressure when the chest is being compressed. This device may be used in combination with at least one physiological sensor that is configured to monitor at least one physiological parameter of the person. In this way, the mechanism for varying the level of intrathoracic pressure may be configured to receive signals from the sensor and to vary the level of impedance of the valve system based on the signals. Examples of sensors that may be used include those that measure respiratory rate, intrathoracic pressure, intratracheal pressure, blood pressure, right heart pressure, heart rate, end tidal $CO_2$, oxygen level, intracranial perfusion, and intracranial pressure. When the thorax is not intact the device may also include a mechanism for varying the level of resistance of the valve system. It may include adding positive expiratory pressure. This device may be used in combination with at least one physiological sensor that is configured to monitor at least one physiological parameter of the person. In this way, the mechanism for varying the pressures and/or volume of respiratory gases within the lungs may be configured to receive signals from the sensor and to vary the level of impedance of the valve system based on the signals. This in turn regulates the amount of respiratory gas volume and/or pressure and the speed at which the gases are actively infused into and extracted from the lungs. Examples of sensors that may be used include those that measure, airway pressure, intratracheal pressure, blood pressure, right heart pressure, heart rate, end tidal $CO_2$, oxygen level, and left heart pressures.

In one aspect, a coupling mechanism may be used to couple the valve system to the person's airway. Examples of coupling mechanisms include a mouthpiece, an endotracheal tube, a supraglottic airway, and a face mask.

A wide variety of valve systems may be used to repetitively decrease the person's intrathoracic pressure or volume of respiratory gases infused into and then extracted from the lungs. For example, valve systems that may be used include those having spring-biased devices, those having automated, electronic or mechanical systems to occlude and open a valve lumen, duck bill valves, ball valves, other pressure sensitive valve systems capable of opening a closing when subjected to low pressure differentials triggered either by spontaneous breathing and/or external systems to manipulate intrathoracic pressures (such as ventilators, phrenic nerve stimulators, iron lungs, and the like).

In another embodiment, the invention provides a method for decreasing intracranial or intraocular pressures when the thorax is intact. Systems and methods are well suited for use in patients having an open chest. Lung volume and pressure may change, however the intrathoracic pressure may remain unchanged as the circuit is open. When the chest is open this approach in general does not lower intracranial pressure. According to the method, a valve system is coupled to a person's airway and is configured to at least periodically reduce or prevent respiratory gases from flowing to the person's lungs. With the valve system coupled to the airway, the person's negative intrathoracic pressure is repetitively decreased to in turn repetitively lower pressures in the venous blood vessels that transport blood out of the head. In so doing, intracranial and intraocular pressures are reduced. Such method also facilitates movement of cerebral spinal fluid. In so doing, intracranial pressures are further reduced.

As such, this method may also be used to treat a person suffering from head trauma that is associated with elevated intracranial pressures, those suffering from heart conditions that increase intracranial pressures, such as atrial fibrillation and heart failure, and those suffering from low blood pressure that is caused in part or whole by a decrease in cardiac output or function.

The person's negative intrathoracic pressure may be repetitively decreased as the person repeatedly inspires through the valve system. This may be done by the person's own efforts (referred to as spontaneous breathing), or by artificially causing the person to repeatedly inspire through the valve system. For example, the person's intrathoracic pressure can be lowered when the thorax is intact by repeatedly stimulating the phrenic nerve, by manipulating the chest with an iron lung cuirass device, by generating negative pressures within the thorax using a ventilator, by applying a vacuum within the thorax that can be regulated by the valve system, by applying a high frequency ventilator that supplies oscillations at a rate of about 200 to about 2000 per minute, or the like. Lowering the intrathoracic pressure can be used to draw respiratory gases into the lungs, draw more blood back to the heart, or both. Lowering the intrathoracic pressure can also be used to lower intracranial and intraocular pressures.

In another aspect, the level of impedance of the valve system may be fixed or variable. If variable, at least one physiological parameters of the person may be measured, and the impedance level may be varied based on the measured parameters.

To couple the valve system to the airway, a variety of techniques may be used, such as by using a mouthpiece, an endotracheal tube, a face mask or the like. Further, the respiratory gases may be prevented from entering the lungs through the valve system until a negative intrathoracic pressure in the range from about 0 cm $H_2O$ to about −25 cm $H_2O$ is achieved, at which time the valve system permits respiratory gases to flow to the lungs.

In another embodiment, the invention provides a method for treating a person suffering from head trauma associated with elevated intracranial pressures. According to the method, a positive pressure breath is delivered to the person with an intact thorax. Respiratory gases are extracted from the person's airway by a vacuum source attached to a device situated between the ventilator and the person's airway to create an intrathoracic vacuum. In turn, this reduces intracranial pressures and may also lower pressures in the venous blood vessels that transport blood out of the head. In some options positive pressure breaths are delivered to the lungs to provide respiratory gases. The steps of delivering positive pressure breaths and extracting respiratory gases are repeated to continue the treatment. Further, a positive pressure breath need not be provided every time before extracting gases, but only when needed to provide proper ventilation. In some cases PEEP can be applied either before or after the extraction of the gases. With this approach, the method and device provide a 3-phase means to modulate airway pressures and when the thorax is intact intrathoracic pressure: the lungs are inflated, the gases are removed from the lungs, and the lungs are partially inflated by PEEP to reduce atelectasis and help preserve lung integrity. In some cases, blood volume may be reduced by the use of diuretics or other means including but not limited to intentional blood loss or volume depletion to enhance the effects of lowering intracranial pressures by lowering intrathoracic pressures.

In some options, the patient may also have his or her intrathoracic pressures externally manipulated with an external thoracic positive pressure source while being provided with the positive pressure breaths and the extraction of gases from the airway. Examples of external thoracic positive pressure sources include a mechanical extrathoracic vest, a body cuirass, a compression piston, a compression cup and the like. These devices may be supplied with energy from a variety of sources, such as pneumatic, electric, combustion and the like. Further, the external compressions may be timed with cardiac activity, e.g., with ECG activity. Further, the external compressions and/or application of the positive pressure breath and the vacuum may be used in combination with invasive means to maintain blood pressure, such as by removing blood from the patient. Also, in some cases, the patient's chest may also need to at least periodically be decompressed. In such cases, a valve may be placed in the patient's airway to prevent air from rushing into the patient's lungs for at least some time in order to increase the magnitude of the negative intrathoracic pressure that is created.

In one aspect, the delivery of the positive pressure breaths and the extraction of gases are performed using a mechanical ventilator. The respiratory gases may be extracted with a constant extraction or a pulsed extraction.

In a further aspect, the breath may be delivered for a time in the range for about 250 milliseconds to about 2 seconds. Also, the breath may be delivered at a rate in the range from about 0.1 liters per second to about 5 liters per second. In another aspect, the vacuum may be maintained at a pressure in the level from about 0 mmHg to about −50 mmHg. The vacuum may be maintained with a negative flow or without any flow. The time that the positive pressure breath is supplied relative to the time in which respiratory gases are extracted may be in the range from about 0.5 to about 0.1. Respiratory gases can be extracted from the lungs over a duration of time ranging from 250 milliseconds to about 10 seconds. The time to achieve the target negative airway pressure may vary depending upon the amount of tidal volume delivered or the desired clinical effect. This can be adjusted manually by an operator or in an automated manner by the IPR device or method. This process may include a feedback loop such that when, for example, the tidal volume is increased, the active gas extraction process is accelerated so that the target negative airway pressure is achieved at the same rate as with the lower tidal volume.

A variety of equipment may be used to extract the respiratory gases including mechanical ventilators, phrenic nerve stimulators, ventilator bags, a vacuum attached to the airway device, iron lung cuirass devices, a chest tube, and the like. In some cases, a threshold valve may also be coupled to the person's airway. The threshold valve may be configured to open when an adult's negative intrathoracic pressure exceeds about −3 cm $H_2O$. For pediatric cases, the valve may open when the pressure exceeds about −2 cm $H_2O$ to about −5 cm $H_2O$. In this way, when the person inhales, the negative intrathoracic pressure may be lowered. When a patient is being ventilated with a mechanical ventilator, the IPR method can be practiced to periodically lower airway pressures to enhance circulation and when the thorax is intact lower intracranial pressure. In some cases the IPR method and device will be incorporated into the means to provide positive pressure ventilation (e.g. a resuscitator bag, a mechanical ventilator, or an anesthesia machine). In some embodiments, IPR therapy can be applied when the patient is being treated with different inspiratory:expiratory (I:E) ratios with the mechanical ventilator. For example, a patient may be treated with a higher I:E ratio (2:1-5:1) and after each inspiration the IPR will reduced airway pressures and/or intrathoracic pressures to between −1 to −20 mmHg for a duration of time varying between 100 milliseconds and 2 seconds prior to the resumption of the positive pressure. By this means respiratory gases can be rapidly extracted from the patients lungs and circulation can be increased.

A variety of schemes may be used to deliver and extract respiratory gases. For example, respiratory gases may be extracted to achieve a pressure of about −5 mmHg to about −10 mmHg and then kept generally constant until the next positive pressure breath. As another example, the positive breath may be slowly delivered and the intrathoracic pressure may be rapidly lowered to a pressure of about −10 mmHg to about −20 mmHg and then gradually increased towards about 0 mmHg. As a further example, the intrathoracic pressure may be slowly lowered to a pressure of about −20 mm Hg.

In a further embodiment, the invention provides a device for lowering intrathoracic pressures. The device comprises a housing having an interface that is adapted to couple the housing to the person's airway. A vacuum source is in fluid communication with the housing for repeatedly extracting respiratory gases from the person's lungs and airway to create and periodically maintain a negative intrathoracic pressure. A vacuum regulator is used to regulate the extraction of respiratory gases from the patient's lungs and airway. Also, a positive pressure source is in fluid communication with the housing for intermittently supplying positive pressure breaths to the person if needed. Such a device may be used to treat a variety of ailments, such as head trauma associated with elevated intracranial pressures, low blood pressure, low blood circulation, low blood volume, cardiac arrest and heart failure.

In some cases, a switching mechanism may be used to stop the extraction of respiratory gases or to deliver of a positive pressure breath. A variety of switching mechanisms may be used, such as mechanical devices, magnetic devices, and electronic devices. Also, a variety of vacuum sources may be used to extract the respiratory gases, including a mechanical ventilator, a vacuum with vacuum regulator, a phrenic nerve stimulator, an extrathoracic vest, a ventilator bag, and an iron lung cuirass device, a suction line, a venturi device attached to an oxygen tank and the like.

To regulate the vacuum, a threshold valve may be placed in fluid communication with the person's airway. The threshold valve may be configured to open when the person's negative intrathoracic pressure reaches about −3 cm $H_2O$ to about −20 cm $H_2O$ to permit respiratory gases to flow into the person's airway. Also, a variety of pressure sources may be used to deliver a positive pressure breath, such as a mechanical ventilator, a hand held bag valve resuscitator, mouth-to-mouth, or a means to provide intermittent positive pressure ventilation. A variety of gauges may be incorporated into the device that are coupled to sensors to measure, for example, the vacuum pressure applied to the patient and other physiological measures such as the intratracheal pressure or intracranial pressure.

In one specific aspect, the invention provides methods and devices that allow the chest to be compressed and decompressed, akin to transforming the chest into a bellows. A wide variety of devices or systems may be used to compress and decompress the chest as described herein. Further, an impedance valve and/or intrathoracic vacuum regulator may be used to lower intrathoracic pressures within the chest when not actively compressing or decompressing the chest to enhance blood flow black to the heart and lower intracranial pressures. Optionally, the device may have the capability to provide periodic positive pressure ventilations. In one particular option, the compressions may be timed with the heartbeat, such as by using an ECG. Also, the decompressions could happened less often than after every compression. For example, the chest may be decompressed about 6 to about 30 times a minute to provide proper negative pressure ventilations, i.e., the creation of a vacuum within the thoracic to naturally inspire air through an unimpeded airway, such as by the use of an iron lung, phrenic nerve stimulation, a suction cup adhered to the chest, and the like. Such a device thus provides a way to artificially maintain blood pressure and ventilation, by negative pressure ventilation and/or by positive pressure ventilations. The device also enhances vital organ circulation and lowers intracranial pressures in patients with low blood pressure who may or may not be able to breathe as well.

In one aspect, embodiments of the present invention encompass medical methods for treating a patient. Exemplary methods may include administering a positive pressure ventilation to the person's airway, administering a positive end expiratory pressure to the person's airway subsequent to the administration of the positive pressure ventilation, and administering a vacuum to the person's airway subsequent to the administration of the positive end expiratory pressure. Related exemplary methods may include administering a positive pressure ventilation to the person's airway, administering a vacuum to the person's airway subsequent to the administration of the positive pressure ventilation, and administering a positive end expiratory pressure to the person's airway subsequent to the administration of the vacuum.

In another aspect, embodiments of the present invention encompass methods of operating an intrathoracic pressure regulation system. Methods may include releasing a ventilation control valve to deliver positive pressure ventilation, activating a ventilation control valve and vacuum delivery valve, releasing a PEEP delivery valve and delivering positive end expiratory pressure to a patient from an internal gas blender at a regulated pressure, energizing the PEEP valve and deenergizing the vacuum delivery valve to generate a regulated vacuum to an airway of the patient, and optionally, repeating any of the preceding method steps.

Embodiments further encompass systems for providing an intrathoracic pressure regulation treatment to an individual. In some cases, a system may include a blended gas pressure source, a PEEP delivery mechanism, a vacuum source, a vacuum regulation mechanism, a vacuum delivery mechanism, a ventilation control valve, a process controller, a ventilator mechanism, and a patient connection.

In some aspects, embodiments of the present invention involve methods for treating a patient that include treating the patient with an intrathoracic pressure regulator so as to regulate the autonomic system of the person.

In still another aspect, embodiments encompass intrathoracic pressure regulator systems, that may include, for example, a manometer, a ventilator port, an inlet cap, a body, a patient port, a vacuum stem, a valve having a piston and a valve face. and a diaphragm.

In one aspect, embodiments of the present invention include methods of removing a respiratory gas from a patient. Exemplary methods may involve applying a vacuum to an airway of the patient, and removing the respiratory gas from the patient at a rate that is based on an amount of tidal volume delivered.

In still a further aspect, embodiments of the present invention may include medical methods for treating a person that involve treating the person with a combination of an intrathoracic pressure regulation treatment and an intra-aortic balloon pump treatment.

In another aspect, embodiments encompass systems for recycling anesthesia gases during a patient treatment. Such systems may include, for example, an endotracheal (ET) tube or mask, an intrathoracic pressure regulator apparatus (ITPR), a patient wye, an ITPR vacuum line, a negative pressure generator, a circuit apparatus, a negative pressure generator apparatus, a vacuum return apparatus, and an anesthesia machine.

According to some aspects, embodiments encompass systems and methods for recycling an anesthesia gas during a medical procedure. Such techniques can involve recycling within an anesthesia machine a gas secondary to increased flow, or capturing an expiratory gas in a separate chamber or scrubber system.

Embodiments of the present invention also include systems for providing an intrathoracic pressure regulation treatment to an individual. Such systems can include a first control valve, a second control valve, a positive inspiratory blower mechanism, an N-exp blower mechanism, a ventilator mechanism, and an anesthesia mechanism.

In yet a further aspect, embodiments of the present invention involve methods for treating a patient with an automated ventilator system or anesthesia machine. Methods may include, for example, administering an intrathoracic pressure regulation treatment to the patient so as to increase circulation in the patient. Methods may also include lowering the intracranial pressure of the patient, when the patient's thorax is intact. Methods may optionally include administering a PEEP treatment to the patient's airway, subsequent to an intrathoracic pressure regulation treatment.

In another aspect, exemplary embodiments include methods of treating a patient that is suffering from or at risk of developing sepsis, shock, heart failure, cardiac arrest, acute respiratory distress syndrome, polytrauma, head disease, elevated hepatic or portal vein pressures, bleeding during abdominal, head and neck surgery, or insufficient circulation during open heart surgery. Embodiments may also include methods for reducing a fluid requirement in a patient during a treatment for low blood circulation or low blood pressure, or methods to increase microcirculation in a patient, or methods to enhance drug circulation in a patient. Any of such methods may optionally include administering an intrathoracic pressure regulation treatment to the patient.

In one aspect, embodiments of the present invention encompass methods for providing a treatment to a patient in need thereof that include administering an intrathoracic pressure regulation protocol to the patient, and administering a CPR protocol to the patient. Embodiments of the present invention may also include methods determining whether to administer an intravenous volume replacement therapy to a patient. Such methods may include administering an IPR protocol to the patient, evaluating a blood pressure in the patient, and administering the intravenous volume replacement therapy to the patient if the evaluated blood pressure in the patient increases rapidly. In some instances, the intravenous volume replacement therapy may include delivery of a crystalloid preparation to the patient. In some instances, the intravenous volume replacement therapy may include delivery of a colloid preparation to the patient.

In another aspect, medical treatments according to embodiments of the present invention can include a sigh breath intermittently to the patient. Sigh breaths can be administered to a patient during the course of a mechanical ventilation procedure, for example where a technician or operator is squeezing a bag on a ventilator or machine, so as to deliver an amount of inflation to the patient's alveoli, thus providing a protective effect for the patient's pulmonary system.

Embodiments of the present invention encompass systems and methods for providing an intrathoracic pressure regulation treatment to an individual. Exemplary systems include an adjustable negative pressure mechanism that delivers an adjustable negative pressure treatment to the patient when the system is in a circulatory assist mode, a positive pressure ventilation mechanism that delivers a positive pressure ventilation treatment to the patient when the system is in a ventilation mode, and an adjustable continuous positive airway pressure mechanism that delivers an adjustable continuous positive airway pressure treatment to the patient when the system is in a CPAP mode. Optionally, a ventilation mechanism may include an anesthesia machine. In some cases, systems include a subatmospheric pressure mechanism that delivers a subatmospheric pressure treatment to the patient after the positive pressure ventilation mechanism delivers the positive pressure ventilation treatment to the patient. Relatedly, systems may include a control mechanism or processor for receiving a operator selection input that designates a member selected from the group consisting of the circulatory assist mode, the ventilation mode, and the CPAP mode, and an operator confirmation input that activates the designated member associated with the operator selection input. In some cases, treatment systems include a supplemental oxygen mechanism that delivers a supplemental oxygen treatment to the patient. Systems may further include a power input configured for association with a battery. In some cases, treatment systems include a battery in operative association with a power input. Optionally, a treatment system can include a positive end expiratory pressure mechanism that delivers a positive end expiratory pressure treatment to the patient before the positive pressure ventilation mechanism delivers the positive pressure ventilation treatment to the patient. In some instances, treatment systems include a sensor mechanism, such as a physiological sensor or a mechanical sensor. Operation of a treatment system may be controlled at least in part based on information received from the sensor mechanism.

In some exemplary systems, a positive pressure ventilation mechanism synchronizes delivery of the positive pressure ventilation treatment to the patient with compression and decompression of the patient's chest during a cardiopulmonary resuscitation (CPR) procedure. Systems may further include a subatmospheric pressure mechanism that delivers a subatmospheric pressure treatment to the patient after the positive pressure ventilation mechanism delivers the positive pressure ventilation treatment to the patient, a control mechanism or processor for receiving a operator selection input that designates a circulatory assist mode, a ventilation mode, and a CPAP mode, and an operator confirmation input that activates the designated member associated with the operator selection input. Relatedly, systems may include a supplemental oxygen mechanism that delivers a supplemental oxygen treatment to the patient. In some cases treatment systems include a power input configured for association with a battery, and a battery in operative association with the power input. Further, treatment systems can include a positive end expiratory pressure mechanism that delivers a positive end expiratory pressure treatment to the patient before the positive pressure ventilation mechanism delivers the positive pressure ventilation treatment to the patient. The positive pressure ventilation mechanism can synchronize delivery of the positive pressure ventilation treatment to the patient with compression and decompression of the patient's chest during a cardiopulmonary resuscitation (CPR) procedure.

In some aspects, treatment systems include a sensor assembly having a pressure gauge, and a feedback assembly. The sensor assembly can sense the number and quality of chest compressions and decompressions during a CPR treatment, and the feedback assembly can provide real-time feedback to a person performing manual compression on the patient. The real-time feedback can include information related to the quality of the CPR treatment, and the information can include data regarding depth data (e.g. depth of chest compression), full chest wall recoil data, and pause duration data. In some cases, sensors can detect pressure within a patient airway, or the depth or force of a chest compression, and such information can be routed through a feedback assembly that provides feedback to a person providing CPR or therapy to the patient. Optionally, a treatment system may include an integrated defibrillator mechanism having a sensor electrode, a capacitor, and a high energy defibrillation mechanism that delivers a defibrillation treatment to the patient. A defibrillator mechanism can provide a treatment that includes a monophasic shock, a biphasic shock, a polyphasic shock, or any combination thereof. In some cases, a treatment system can include an adjustment mechanism that adjusts the adjustable negative pressure mechanism, the positive pressure ventilation mechanism, continuous positive airway pressure mechanism, or any combination thereof, based on a measured physiological signal from the patient. A measured physiological signal of the patient can include, for example, a blood pressure signal, an end tidal $CO_2$ signal, or a brain $O_2$ signal. In some cases, a treatment device can include a communication module that communicates with an external medical device. A communication module can include a blue tooth assembly or a radiofrequency assembly, for example. In some instances, the communication module communicates with an external medical device such as a defibrillator or an automated chest compressor.

Treatment systems according to embodiments of the present invention may also include a timing mechanism that coordinates a change in intrathoracic pressure provided by a an adjustable negative pressure mechanism, a positive pressure ventilation mechanism, or a continuous positive airway pressure mechanism, with a medical device treatment such as a defibrillation shock procedure or a chest compression and release procedure. Exemplary treatment systems may also include a user interface. In some cases, a user interface includes a circular control panel. In some cases, a user interface includes a symmetrical control panel. Optionally, a user interface may include a circular control panel having three circumferentially arranged rim segments. Treatment systems may also include a bilevel positive airway pressure mechanism that delivers a bilevel positive airway pressure treatment to the patient.

In a further aspect, embodiments of the present invention include a system for increasing cardiac output, stroke volume, and pulse pressure in an individual during an intrathoracic pressure regulation treatment. Treatment systems may include a positive pressure ventilation mechanism that delivers a positive pressure ventilation treatment to the patient, and the positive pressure ventilation treatment can include a series of repeated positive pressure ventilations. Treatment systems can further include a respiratory extraction mechanism that actively extracts respiratory gases from the patient between consecutive positive pressure ventilations. Optionally, the systems can have a weight that is less than twelve pounds. In some system embodiments, a positive pressure ventilation mechanism or a respiratory extraction mechanism can operate to regulate a level of negative airway pressure automatically with a feedback loop based on a measured patient parameter. In some cases, a measured patient parameter provides an indicator of increased circulation. In some cases, a measured patient parameter can include an end tidal carbon dioxide, a cardiac output, a transthoracic impedance, a muscle oxygenation, or a muscle pH.

Exemplary systems may include a processor, and a memory coupled with the processor. The memory may include a positive pressure ventilation code module comprising instructions for operating the positive pressure ventilation mechanism, and a respiratory extraction code module comprising instructions for operating the respiratory extraction mechanism. In some cases, a treatment system includes a circuit having two limbs, a manifold that maintains separation between inspiratory gases and expiratory gases, and a removable protective case that is resistant to impact and moisture. Treatment systems may also include a sensor assembly that facilitates breath control. What is more, treatment systems may include a blower mechanism that facilitates control of expiratory resistance. Optionally, systems can be configured so that a blower mechanism operates based on a feedback control loop.

In another aspect, embodiments of the present invention encompass a user interface of an intrathoracic pressure regulation system. An exemplary user interface may include a basic mode display with a circulatory assist mode sub-interface having a set of patient size selection inputs, a ventilation mode sub-interface having a set of patient size selection inputs, and a continuous positive airway pressure (CPAP) mode sub-interface having a set of pressure selection inputs. The interface may also have an airway pressure display with a positive airway pressure section and a negative airway pressure section. An interface can further include a mode confirmation sub-interface, and an advanced mode display with a manual control interface having a respiratory rate selection input, a tidal volume selection input, a positive end expiratory pressure selection input, and a circulatory assist selection input. In some cases, a user interface may include a lock-out mechanism that can lock-out use of the advanced mode display. Optionally, a circulatory assist mode sub-interface, a ventilation mode sub-interface, and a continuous positive airway pressure (CPAP) mode sub-interface can be arranged as three circumferentially arranged rim segments of a circle.

In still further aspects, embodiments of the present invention encompass an intrathoracic pressure regulator system for use in treating a patient. Exemplary systems include a patient port that fluidly communicates with the patient, a ventilator port that fluidly communicates with a ventilator mechanism for facilitating a positive pressure ventilation procedure administered to the patient via the patient port, a vacuum port that fluidly communicates with a vacuum mechanism for facilitating a vacuum procedure administered to the patient via the patient port, and a valve for controlling fluid flow. During administration of a positive pressure ventilation procedure the valve can operate to allow fluid flow between the ventilator port and the patient port and inhibits fluid flow between the vacuum port and the patient port. During administration of the vacuum procedure the valve can operate to inhibit fluid flow between the ventilator port and the patient port and allows fluid flow between the vacuum port and the patient port. Optionally, a ventilator mechanism may include an anesthesia machine. In some cases, systems include a positive end expiratory pressure mechanism in operative association with the valve. Optionally, the valve can operate to allow fluid flow between the positive end expiratory pressure mechanism and the patient port during administration of a positive end expiratory pressure treatment that occurs either before or after administration of the vacuum procedure. In related embodiments, systems include a pressure sensor in fluid communication with the patient port. The pressure sensor can indicate a positive pressure application during administration of the positive pressure ventilation procedure and a negative pressure application during administration of the vacuum procedure. In some instances, upon initiation of the positive pressure ventilation procedure the valve operates to inhibit fluid flow between the ventilator port and the patient port and to inhibit fluid flow between the vacuum port and the patient port.

In related aspects, embodiments of the present invention provide an intrathoracic pressure regulator system for use in treating a patient. The system can include a processor that accepts an operator selection input designating a circulatory assist mode, a ventilation mode, or a continuous positive airway pressure mode. The system can also include a manifold assembly in operative association with the processor. The manifold assembly can have an oxygen inlet port in fluid communication with an inspiratory plane. The oxygen inlet port can receive oxygen from an oxygen source. The manifold assembly can also include an air inlet port in fluid communication with the inspiratory plane. The air inlet port can receive air from an air source. The manifold assembly can also include an expiratory gas outlet port in fluid communication with an expiratory plane. The expiratory gas outlet port can allow expired gas to pass therethrough toward a negative pressure mechanism. The manifold assembly can further include a patient circuit interface having an inspiratory lumen that transmits air and oxygen toward the patient and an expiratory lumen that transmits expired gas away from the patient. Treatment systems can also include an inspiratory control valve assembly that controls fluid flow between the inspiratory plane and the inspiratory lumen, an expiratory control valve assembly that controls fluid flow between the expiratory plane and the expiratory gas outlet port, and a fixed or adjustable negative pressure mechanism that delivers a negative pressure treatment to the patient via the expiratory lumen when the system is in a circulatory assist mode. In some cases, the system includes a positive pressure ventilation mechanism that delivers a positive pressure ventilation treatment to the patient via the inspiratory lumen when the system is in a ventilation mode, or an adjustable continuous positive airway pressure mechanism that delivers an adjustable continuous positive airway pressure treatment to the patient via the expiratory lumen when the system is in a continuous positive airway pressure mode, or both. Optionally, a ventilator mechanism can include an anesthesia machine. Optionally, the system can include a positive end expiratory pressure mechanism that delivers a positive end expiratory pressure treatment to the patient. Some treatment systems include a user display, and a sensor mechanism such as a physiological sensor or a mechanical sensor. The processor can operate to transmit display instructions to a user display based on patient information received from the sensor mechanism for displaying information related to CPR quality or circulation. In some cases, the processor can operate to transmit display instructions to the user display based on patient feedback information received from the sensor mechanism. The display instructions can relate to CPR quality during administration of a CPR treatment. In some cases, the processor can transmit display instructions to the user display based on patient feedback information received from the sensor mechanism. The display instructions can relate to circulation during administration of a non-CPR treatment.

In another aspect, embodiments of the present invention encompass methods of providing an intrathoracic pressure regulation treatment to a patient that is suffering from or at risk of developing sepsis, shock, heart failure, cardiac arrest, acute respiratory distress syndrome, polytrauma, head disease, elevated hepatic or portal vein pressures, bleeding during abdominal, head and neck surgery, or insufficient circulation during open heart surgery. Methods may include administering a positive pressure ventilation generated by a ventilator mechanism to the person's airway via a patient port of an intrathoracic pressure regulator system, and administering a vacuum generated by a vacuum mechanism to the person's airway via the patient port of the intrathoracic pressure regulator system. During administration of the positive pressure ventilation a fluid control valve of the intrathoracic pressure regulator system can allow fluid flow between the ventilator mechanism and the patient port and inhibits fluid flow between the vacuum mechanism and the patient port, and during administration of the vacuum the fluid control valve of the intrathoracic pressure regulator system can inhibit fluid flow between the ventilator mechanism and the patient port and allows fluid flow between the vacuum mechanism and the patient port. Treatment methods may also include administering a positive end expiratory pressure to the person's airway subsequent to the administration of the positive pressure ventilation. The vacuum can be administered to the patient's airway subsequent to the administration of the positive end expiratory pressure. Some methods include administering a positive end expiratory pressure to the person's airway subsequent to the administration of the vacuum. The vacuum can be administered to the patient's airway subsequent to the administration of the positive pressure ventilation. Optionally, methods may include displaying an indication of a positive pressure application during administration of the positive pressure ventilation procedure and an indication of a negative pressure application during administration of the vacuum procedure.

In a still further aspect, embodiments of the present invention encompass methods of providing an intrathoracic pressure regulation treatment to a patient that is suffering from or at risk of developing sepsis, shock, heart failure, cardiac arrest, acute respiratory distress syndrome, polytrauma, head disease, elevated hepatic or portal vein pressures, bleeding during abdominal, head and neck surgery, or insufficient circulation during open heart surgery. Exemplary methods include administering a fixed or adjustable negative pressure treatment to the patient via an expiratory lumen of an intrathoracic pressure regulator system when the system is in a circulatory assist mode, and either administering a positive pressure ventilation treatment to the patient via an inspiratory lumen of the intrathoracic pressure regulator system when the system is in a ventilation mode, or administering an adjustable continuous positive airway pressure treatment to the patient via the expiratory lumen of the intrathoracic pressure regulator system when the system is in a continuous positive airway pressure mode. In some cases, methods include administering a positive end expiratory pressure treatment to the patient with a positive end expiratory pressure mechanism of the intrathoracic pressure regulator system. In some cases, methods include both administering the positive pressure ventilation treatment to the patient via the inspiratory lumen of the intrathoracic pressure regulator system when the system is in the ventilation mode, and administering a positive end expiratory pressure to the person's airway subsequent to the administration of the positive pressure ventilation. The negative pressure treatment can be administered to the patient's airway subsequent to the administration of the positive end expiratory pressure.

In some cases, methods include administering a positive pressure ventilation treatment to the patient via the inspiratory lumen of the intrathoracic pressure regulator system when the system is in the ventilation mode, and administering a positive end expiratory pressure to the person's airway subsequent to the administration of the negative pressure treatment. The negative pressure treatment can be administered to the patient's airway subsequent to the administration of the positive pressure ventilation. In some cases, methods include displaying information related to CPR quality on a user display of the intrathoracic pressure regulator system during administration of a CPR treatment. In some cases, methods include displaying information related to circulation on a user display of the intrathoracic pressure regulator system during administration of a non CPR treatment.

For a fuller understanding of the nature and advantages of the present invention, reference should be had to the ensuing detailed description taken in conjunction with the accompanying drawings.

BRIEF DESCRIPTION OF THE DRAWINGS

FIGS. 13A and 13B schematically illustrate one device that may be used to lower intrathoracic pressures with a non-breathing patient according to the invention.

FIGS. 14A and 14B illustrate another device that may be used to lower intrathoracic pressures with a non-breathing patient according to the invention.

FIGS. 16A and 16B show aspects of intrathoracic pressure regulation techniques according to embodiments of the present invention.

FIGS. 18A, 18B, and 18C show aspects of intrathoracic pressure regulation techniques according to embodiments of the present invention.

FIGS. 19A-1, 19A-2, 19B, 19C, 19D, 19E, 19F, and 19G show aspects of an intrathoracic pressure regulation device according to embodiments of the present invention.

FIGS. 22A, 22B, 22C, 22D, 22E, 22F, and 22G show aspects of intrathoracic pressure regulation systems according to embodiments of the present invention.

DETAILED DESCRIPTION OF THE INVENTION

Figure 1:
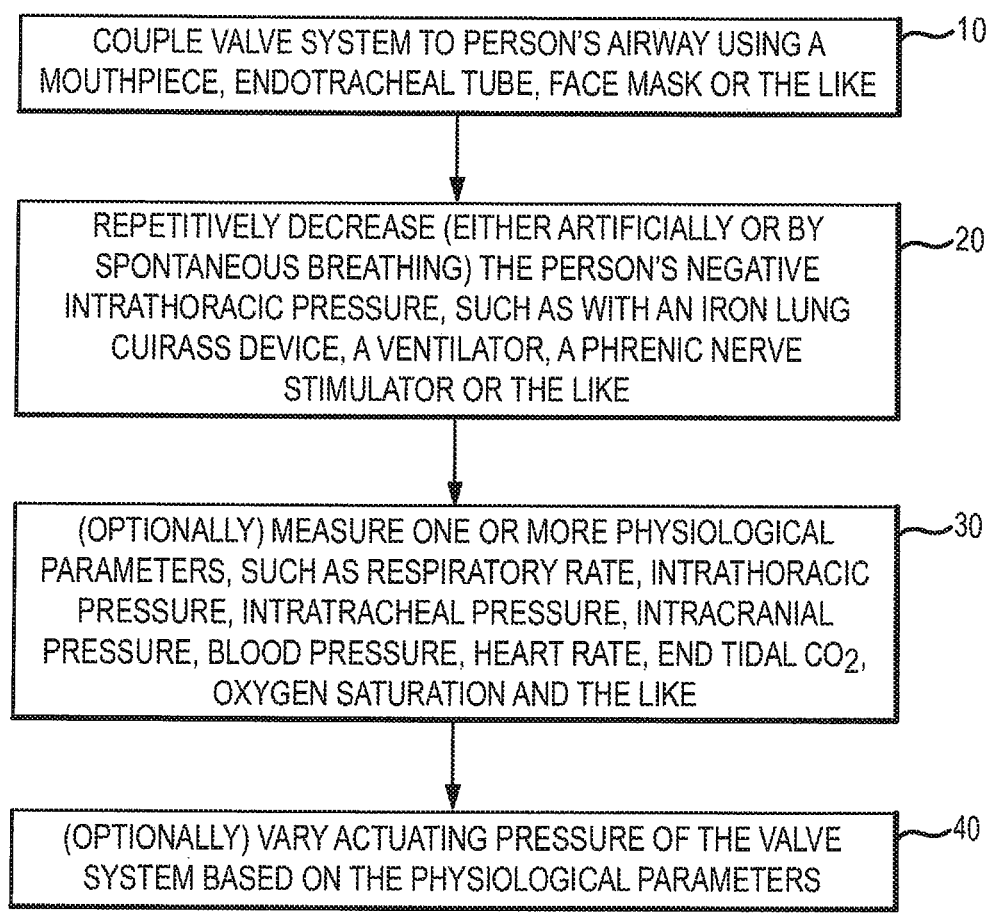
FIG. 1 is a flow chart illustrating one method for reducing intracranial and intraocular pressures according to the invention.

Embodiments of the present invention encompass techniques for regulating intrathoracic pressure, airway pressure, or endotracheal pressure. In some cases, a positive end expiratory pressure (PEEP) can be provided prior to application of a vacuum. In some cases, a PEEP can be provided subsequent to application of a vacuum. The addition of PEEP may provide additional oxygenation for a diseased or compromised lung, more than just the positive pressure breath would. In some cases, PEEP is provided via mechanical ventilation, and can refer to pressure greater than atmospheric pressure that is present in the airway at the end of the expiratory cycle. PEEP can improve gas exchange by preventing alveolar collapse, recruiting more lung units, increasing functional residual capacity, and redistributing fluid in the alveoli. In some cases, the use of ITPR can upregulate the autonomic nervous system. And in some cases, the combination of IPR and an intra-aortic balloon pump (IABP) can provide an even bigger effect on enhancing circulation than either provides alone.

In a broad sense, the invention provides devices and techniques for lowering intracranial and intraocular pressures and increasing cerebral perfusion pressures. Such devices and techniques may be particularly helpful with patients who have suffered a traumatic brain injury and those with low blood flow states and low blood pressure. Examples of conditions that may be treated include hypotension, shock secondary to hypovolemia, sepsis, heart failure, and the like. One way to lower the pressure within the head but maintain or increase systemic pressures is by using a valve system that is coupled to a person's airway and that is used to lower intrathoracic pressures. In so doing, the valve systems may be used to accelerate the removal of venous blood from the brain, thereby decreasing intracranial and intraocular pressures. At the same time, the systemic pressures increase due to enhancement of venous return to the heart. Other techniques may be used as well, such as by creating a vacuum intermittently within the thorax and/or by repeatedly compressing and/or decompressing the patient's chest using an external thoracic positive pressure source. By reducing intracranial pressures, movement of cerebral spinal fluid is also enhanced. In so doing, intracranial pressures are further reduced thereby providing further treatment for those suffering from head trauma. In some cases, the valve systems may also be used to treat the brain function in a person suffering from a heart condition (atrial fibrillation, heart failure, cardiac tamponade, and the like) that results in elevated intracranial pressures. Such heart conditions may include, for example, atrial fibrillation or heart failure. By reducing intracranial pressures, cerebral spinal fluid movement and translocation is increased to help improve brain function.

Intracranial pressures are regulated by the amount the cerebral perfusion pressure, which is determined by the arterial blood pressure to the head, the pressures within the skull, and the pressures within the venous system that drains blood flow from the brain. The devices and methods of the invention may be used to enhance the egress of venous blood out of the brain, thereby lowering intracranial pressures. The devices and methods can be used in patients that are breathing spontaneously and those that require assisted ventilation. To do so, the devices and methods may be used to augment the intrathoracic vacuum effect each time a patient inhales (or in the case of a non-breathing patient, each time the pressure within the chest is manipulated to fall below atmospheric pressure), thereby lowering the pressures in the thorax and in the venous blood vessels that transport blood out of the brain. The vacuum effect is transduced back into the brain, and as a result, intracranial pressures are lowered with each inspiratory effort. This in turn causes more venous blood to flow out of the head than would otherwise be possible, resulting in lower intracranial pressures and lower intraocular pressures. In addition, circulation to the vital organs is increased as the increase in venous return to the heart each time a negative intrathoracic pressure is generated results in an increase in cardiac output and improved vital organ perfusion. As such, this invention may be used to help patients suffering from low cardiac output states and low blood pressure.

To prevent or impede respiratory gases from flowing to the lungs, a variety of impeding or preventing mechanisms may be used, including those described in U.S. Pat. Nos. 5,551,420; 5,692,498; 6,062,219; 5,730,122; 6,155,257; 6,234,916 and 6,224,562, and in U.S. patent application Ser. No. 10/224,263, filed on Aug. 19, 2002 ("Systems and Methods for Enhancing Blood Circulation", Ser. No. 10/401,493, filed Mar. 28, 2003 ("Diabetes Treatment Systems and Methods", Ser. No. 09/966,945, filed Sep. 28, 2001 and Ser. No. 09/967,029, filed Sep. 28, 2001, the complete disclosures of which are herein incorporated by reference. The valve systems may be configured to completely prevent or provide resistance to the inflow of respiratory gases into the patient while the patient inspires. For valve systems that completely prevent the flow of respiratory gases, such valves may be configured as pressure responsive valves that open after a threshold negative intrathoracic pressure has been reached.

For example, the resistance to the inflow of respiratory gases may be set between about 0 cm $H_2O$ and about −25 cm $H_2O$ and may be variable or fixed. More preferably, the valve system may be configured to open when the negative intrathoracic pressure is in the range from about −2 cm $H_2O$ to about −20 cm $H_2O$. In addition, the valve system may used continuously or on a variable basis. For example, the valve system may be used for every other spontaneous breath.

Although not intended to be limiting, specific kinds of impedance valves that may be used to reduce intracranial and intraocular pressures include those having spring-biased devices, automated/electronic and mechanical means to occlude and open a valve lumen, duck bill valves, ball valves, and other pressure sensitive valve systems capable of opening and closing when subjected to low pressure differentials triggered either by spontaneous breathing and/or external means to manipulate intrathoracic pressure (such as ventilators, phrenic nerve stimulators, an iron lung, and the like).

In the past, such threshold valve systems have been used to increase the venous preload on the heart and to increase cardiac output, stroke volume and blood pressure because of the augmented effects of the intrathoracic vacuum on the subsequent cardiac contraction. In contrast, the techniques of the invention function by facilitating the removal of blood from the venous side of the brain. Although there may be an increase in blood flow out of the heart to the vital organs (including to the brain) when using such valve systems, the effect of the valve systems on lowering of intracranial pressures was quite unexpected because of the known increase in blood flow to the brain. Remarkably, however, the reduction of venous blood pressures from the brain remains substantial when using the valve systems. Thus, despite the increase in blood flow to the brain, the net effect of the valve system is a decrease in intracranial pressures.

With the valve system coupled to the person's airway, the negative intrathoracic pressure may be enhanced by inspiring through the valve system. If the person is spontaneously breathing, the person may simply breath through the valve system. If the person is not breathing, artificial inspiration may be induced using a variety of techniques, including electrical stimulation of the diaphragm, a negative pressure ventilator such as a body cuirass or iron lung, or a positive pressure ventilator capable of also generating a vacuum between positive pressure ventilations.

The valve systems may have a fixed actuating pressure or may be variable so that once a desired negative intrathoracic pressure is reached, the resistance to flow may be lessened. Further, the valves of the invention may be configured to be variable, either manually or automatically. The extent to which the resistance to flow is varied may be based on physiological parameters measured by one or more sensors that are associated with the person being treated. As such, the resistance to flow may be varied so that the person's physiological parameters are brought within an acceptable range. If an automated system is used, such sensors may be coupled to a controller which is employed to control one or more mechanisms that vary the resistance or actuating pressure of the inflow valve as generally described in the references that have been incorporated by reference.

Hence, the valve systems of the invention may also incorporate or be associated with sensors that are used to detect changes in intrathoracic pressures or other physiological parameters. In one aspect, the sensors may be configured to wirelessly transmit their measured signals to a remote receiver that is in communication with a controller. In turn the controller may use the measured signals to vary operation of the valve systems described or incorporated by reference herein. For example, sensors may be used to sense blood pressure, pressures within the heart, intrathoracic pressures, positive end expiratory pressure, respiratory rate, intracranial pressures, intraocular pressures, respiratory flow, oxygen delivery, temperature, blood pH, end tidal $CO_2$, tissue $CO_2$, blood oxygen, cardiac output or the like. Signals from these sensors may be wirelessly transmitted to a receiver. This information may then be used by a controller to control the actuating pressure or the resistance of an inflow valve as described in the references incorporated herein by reference.

The techniques for reducing intracranial pressures may be used in a variety of settings. For example, the techniques may be used in person's who are spontaneously breathing, those who are not breathing but whose hearts are beating, and those in cardiac arrest. In the latter case, the techniques may use some means to create a vacuum intermittently within the thorax during the performance of CPR. This could be by using a valve system or some other type of pressure manipulation system. Further, such systems may be used in other settings as well, including when the person is breathing.

FIG. 1 is flow diagram illustrating one method for reducing intracranial or intraocular pressures. As shown in step 10, the process proceeds by coupling a valve system to the person's airway. Any kind of coupling mechanism may be used, such as by a mouthpiece, an endotracheal tube, a face mask, or the like. Further, any of the valve systems described or incorporated herein by reference may be used. In step 20, the person's negative intrathoracic pressure is repetitively decreased (either artificially or by spontaneous breathing). Examples of techniques to artificially reduce the negative intrathoracic pressure include use of an iron lung cuirass device, a ventilator that is capable of generating negative pressures, a ventilator that is capable of providing high frequency oscillations at a rate of about 200 to about 2000 per minute, a phrenic nerve stimulator, or the like. As the person's negative intrathoracic pressure is repeatedly decreased while the valve system is coupled to the airway, the pressures in the venous vessels that transport blood out of the head are also lowered. In so doing, intracranial and intraocular pressures are reduced.

As shown in step 30, various physiological parameters of the person may optionally be measured. Examples of such parameters include respiratory rate, intrathoracic pressure, intertracheal pressure, intracranial pressure, intracranial blood flow, intraocular pressure, blood pressure, heart rate, end tidal $CO_2$, oxygen saturation, and the like. Further, as shown in step 40, the valve system's actuating threshold level may optionally be varied based on the measured physiological parameters. This may be done to maximize the amount of blood drawn out of the brain or simply to monitor the patient's condition to insure that the patient remains stable.

Figure 2:
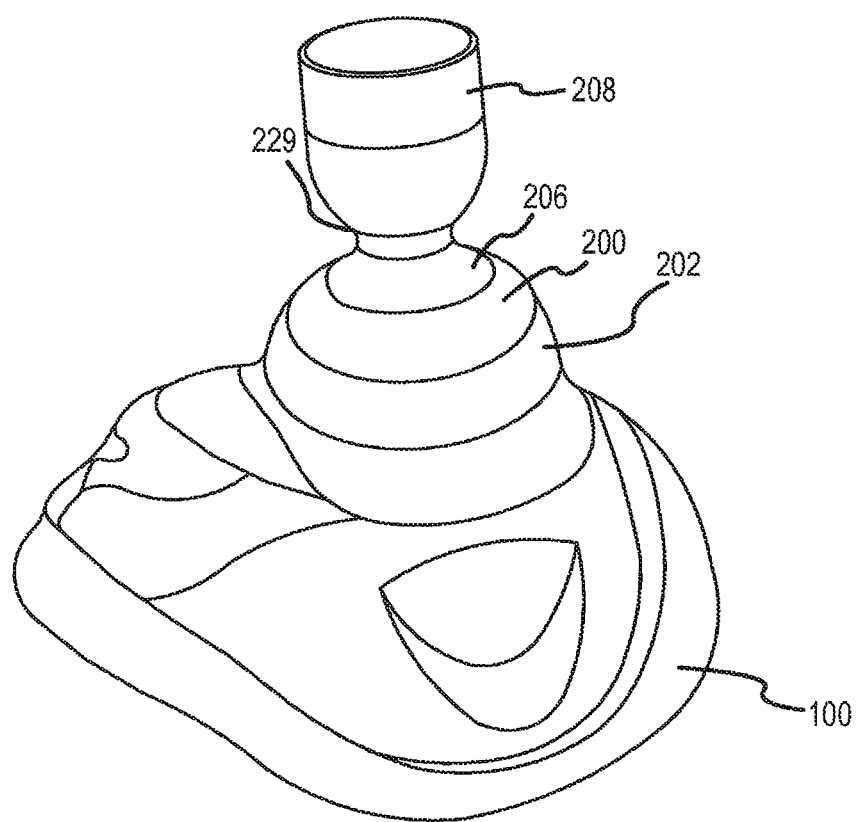
FIG. 2 is a perspective view of one embodiment of a facial mask and a valve system that may be used to reduce intracranial and intraocular pressures according to the invention.

FIG. 2 illustrates one embodiment of a facial mask 100 to which is coupled a valve system 200. Mask 100 is configured to be secured to a patient's face so as to cover the mouth and nose. Mask 100 and valve system 200 are examples of one type of equipment that may be used to lower intrathoracic pressures and thereby lower intracranial and intraocular pressures. However, it will be appreciated that other valve systems and other coupling arrangements may be used including, for example, those previously referenced. As such the invention is not intended to be limited to the specific valve system and mask described below.

Figure 3:
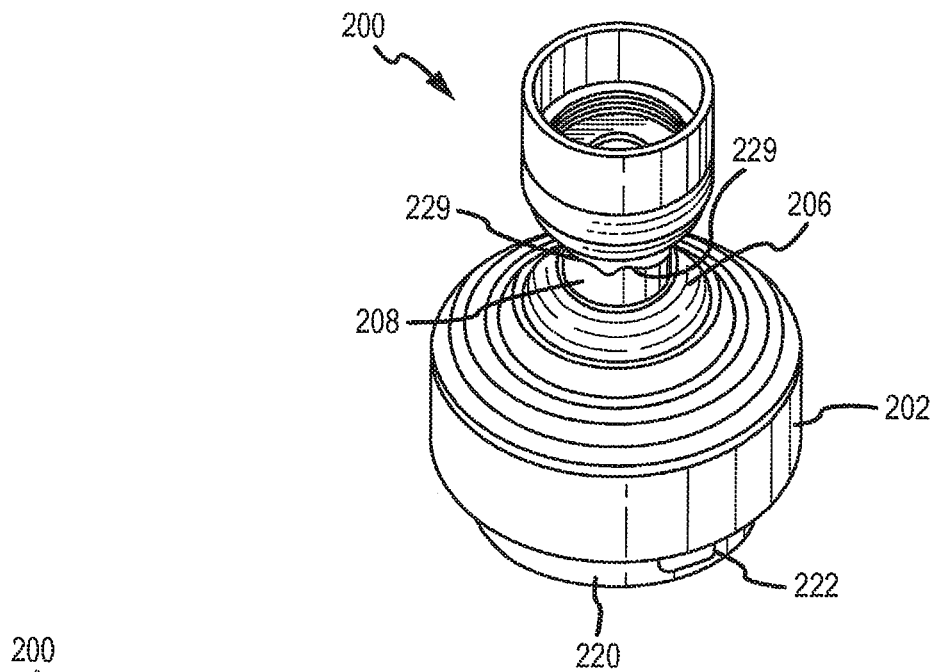
FIG. 3 is a perspective view of the valve system of FIG. 2.
Figure 4:
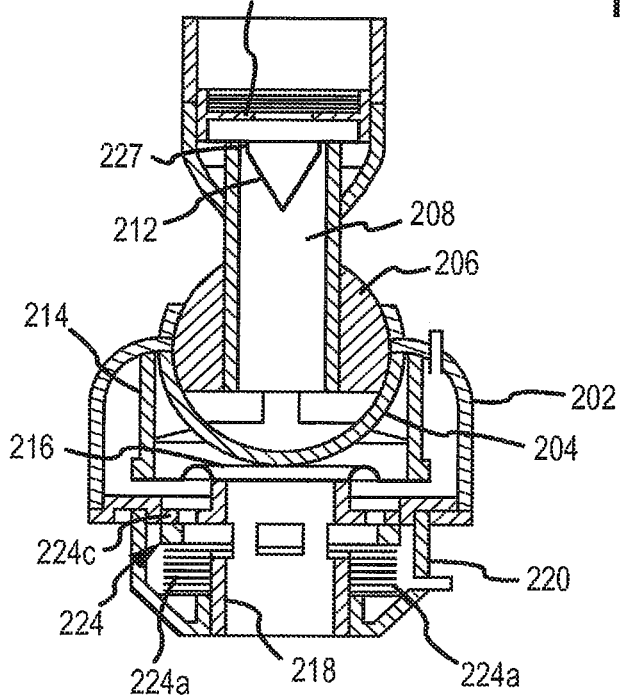
FIG. 4 is a cross sectional side view of the valve system of FIG. 3.
Figure 5:
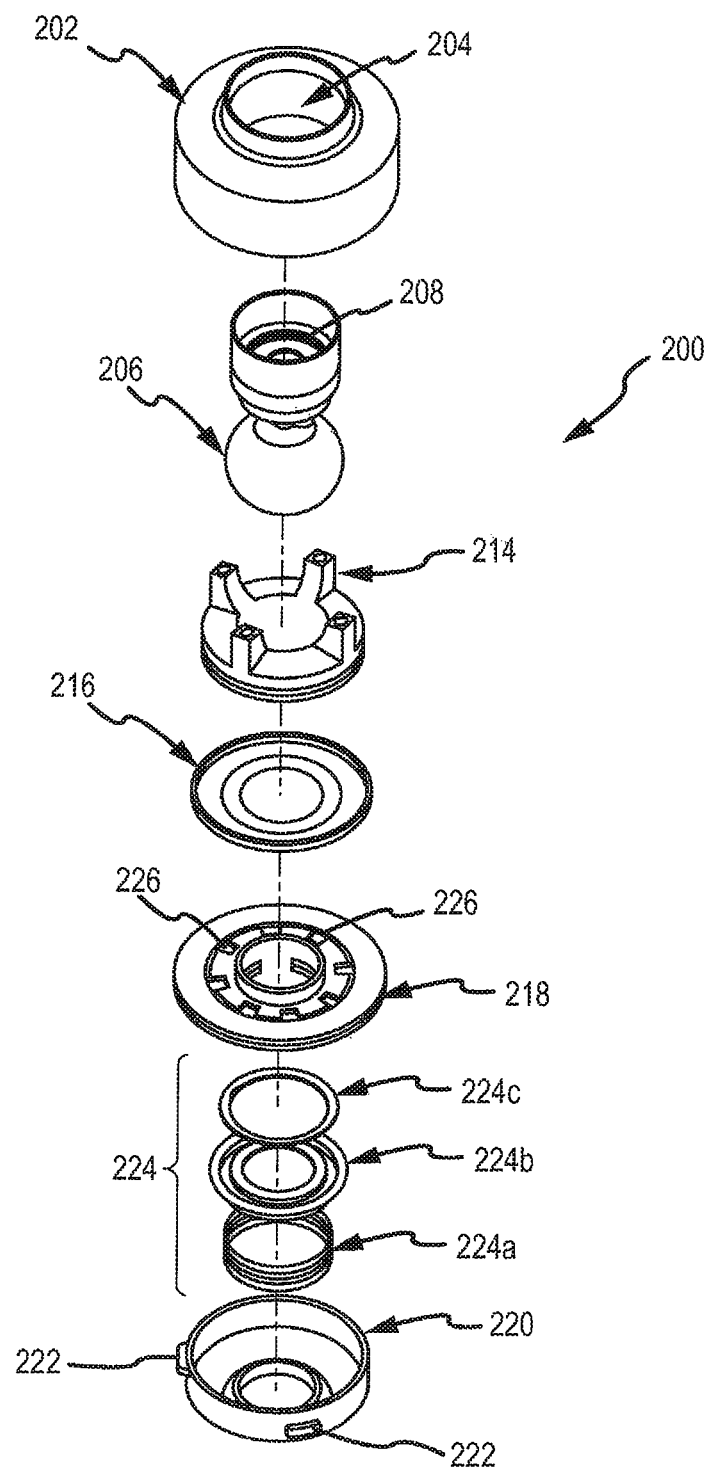
FIG. 5 is an exploded view of the valve system of FIG. 3.

Referring also to FIGS. 3-5, valve system 200 will be described in greater detail. Valve system 200 includes a valve housing 202 with a socket 204 into which a ball 206 of a ventilation tube 208 is received. In this way, ventilation tube 208 may rotate about a horizontal axis and pivot relative to a vertical axis. A respiratory source, such as a ventilation bag, may be coupled to tube 208 to assist in ventilation. Disposed in ventilation tube 208 is a filter 210 that is spaced above a duck bill valve 212. A diaphragm holder 214 that holds a diaphragm 216 is held within housing 202. Valve system 200 further includes a patient port 218 that is held in place by a second housing 220. Housing 220 conveniently includes tabs 222 to facilitate coupling of valve system 200 with facial mask 100. Also held within housing 220 is a check valve 224 that comprises a spring 224 $a$, a ring member 224 $b$, and an o-ring 224 $c$. Spring 224 $a$ biases ring member 224 $b$ against patient port 218. Patient port 218 includes bypass openings 226 that are covered by o-ring 224 $c$ of check valve 224 until the pressure in patient port 218 reaches a threshold negative pressure to cause spring 224 $a$ to compress.

When the patient is actively ventilated, respiratory gases are forced through ventilation tube 208. The gases flow through filter 210, through duck bill valve 212, and forces up diaphragm 214 to permit the gases to exit through port 218. Hence, at any time the patient may be ventilated simply by forcing the respiratory gases through tube 208.

During the exhalation phase of a breathing cycle, expired gases flow through port 218 and lift up diaphragm 214. The gases then flow through a passage 227 in ventilation tube 208 where they exit the system through openings 229 (see FIG. 3).

During the inhalation phase of a breathing cycle, valve system 200 prevents respiratory gases from flowing into the lungs until a threshold negative intrathoracic pressure level is exceeded. When this pressure level is exceeded, check valve 224 is pulled downward as springs 224 $a$ are compressed to permit respiratory gases to flow through openings 226 and to the patient's lungs by initially passing through tube 208 and duck bill valve 212. Valve 224 may be set to open when the negative intrathoracic pressure is in the range from about 0 cm $H_2O$ to about −25 cm $H_2O$, and more preferably from about −2 cm $H_2O$ to about −20 cm $H_2O$. Hence, the magnitude and duration of negative intrathoracic pressure may be enhanced during patient inhalation by use of valve system 200. Once the intrathoracic pressure falls below the threshold, recoil spring 224 $a$ again close check valve 224. In this way, pressure within the venous blood vessels that transport blood out of the brain are also lowered. In so doing, more blood is drawn out of the brain to reduce intracranial and intraocular pressures.

Figure 6:
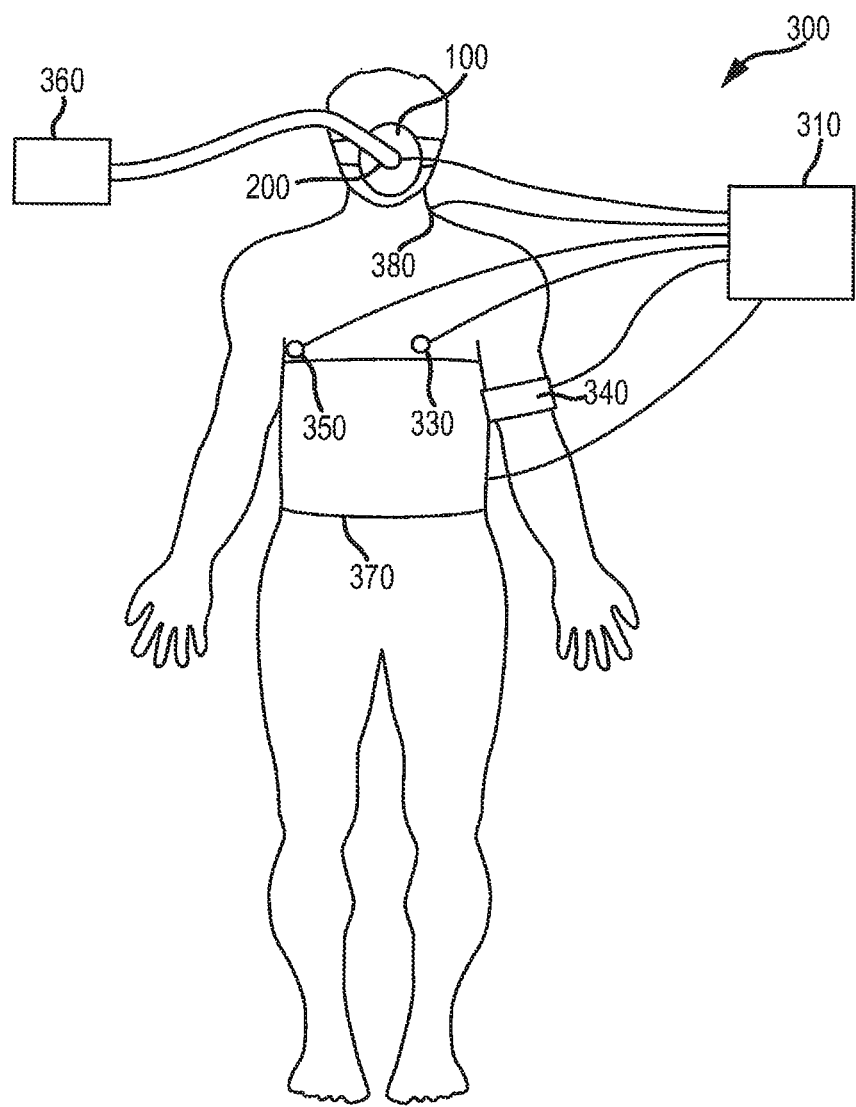
FIG. 6 is a schematic diagram of a system for reducing intracranial and intraocular pressures according to the invention.

Any of the valve systems described herein may be incorporated into a treatment system 300 as illustrated in FIG. 6. System 300 may conveniently include facial mask 100 and valve system 200, although any of the valve systems or interfacing mechanisms described herein or the like may be used, including but not limited to the valve system of FIG. 14. Valve system 200 may conveniently be coupled to a controller 310. In turn, controller 310 may be used to control the impedance level of valve system 200 in a manner similar to any of the embodiments described or incorporated herein. The level of impedance may be varied based on measurements of physiological parameters, or using a programmed schedule of changes. System 300 may include a wide variety of sensors and/or measuring devices to measure any of the physiological parameters described herein. These sensors or measuring devices may be integrated within or coupled to valve system 200 or facial mask, or may be separate.

For example, valve system 200 may include a pressure transducer for taking pressure measurements (such as intrathoracic pressures, intracranial pressures, intraocular pressures), a flow rate measuring device for measuring the flow rate of air into or out of the lungs, or a $CO_2$ sensor for measuring expired $CO_2$.

Examples of other sensors or measuring devices include a heart rate sensor 330, a blood pressure sensor 340, and a temperature sensor 350. These sensors may also be coupled to controller 310 so that measurements may be recorded. Further, it will be appreciated that other types of measuring devices may be used to measure various physiological parameters, such as oxygen saturation and/or blood levels of $O_2$, blood lactate, blood pH, tissue lactate, tissue pH, blood pressure, pressures within the heart, intrathoracic pressures, positive end expiratory pressure, respiratory rate, intracranial pressures, intraocular pressures, respiratory flow, oxygen delivery, temperature, end tidal $CO_2$, tissue $CO_2$, cardiac output or the like.

In some cases, controller 310 may be used to control valve system 200, to control any sensors or measuring devices, to record measurements, and to perform any comparisons. Alternatively, a set of computers and/or controllers may be used in combination to perform such tasks. This equipment may have appropriate processors, display screens, input and output devices, entry devices, memory or databases, software, and the like needed to operate system 300.

A variety of devices may also be coupled to controller 310 to cause the person to artificially inspire. For example, such devices may comprise a ventilator 360, an iron lung cuirass device 370 or a phrenic nerve stimulator 380. Ventilator 360 may be configured to create a negative intrathoracic pressure within the person, or may be a high frequency ventilator capable of generating oscillations at about 200 to about 2000 per minute.

Example 1

The following is a non-limiting example illustrating how intracranial pressures may be lowered according to the invention. In this example, 30 kg pigs were anesthetized with propofol. Using a micromanometer-tipped electronic Millar catheter inserted below the dura, intracranial pressures were measured continuously in the spontaneously breathing pigs. Intrathoracic pressures (ITP) were recorded using a Millar catheter placed in the trachea at the level of the carina. After stabilizing the pigs blood pressure, heart rate, and ventilation rate, intracranial pressures (ICP) and intrathoracic pressures were recorded, with 0 cmH2O inspiratory impedance and then with inspiratory impedances of 5, 10, 15, and 20 cm $H_2O$. Inspiratory impedance was achieved using an impedance threshold valve (ITV) as described in FIGS. 2-5.

Figure 7:
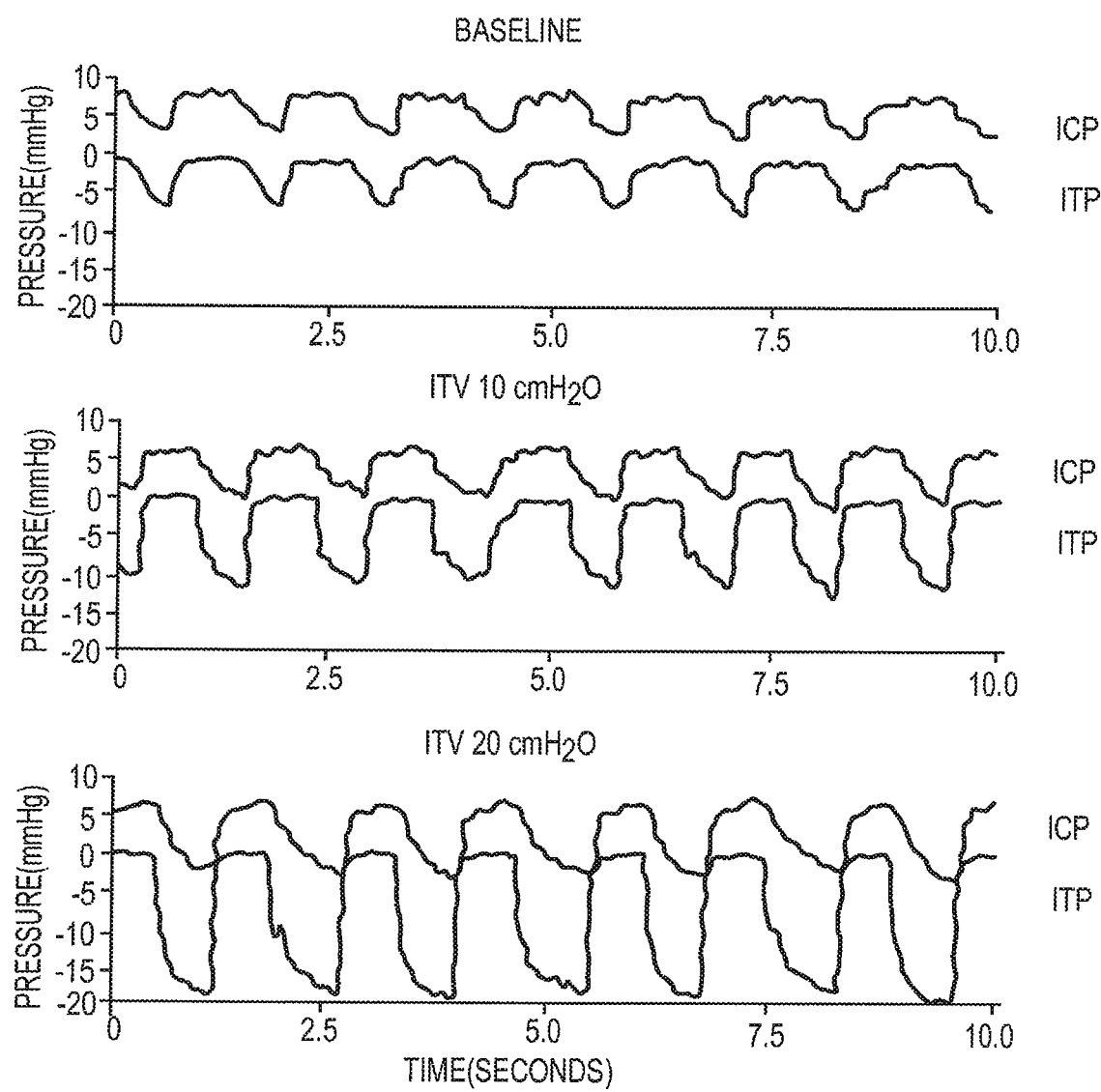
FIG. 7 is a series of graphs illustrating the lowering of intracranial pressures in an animal study.
Figure 8:
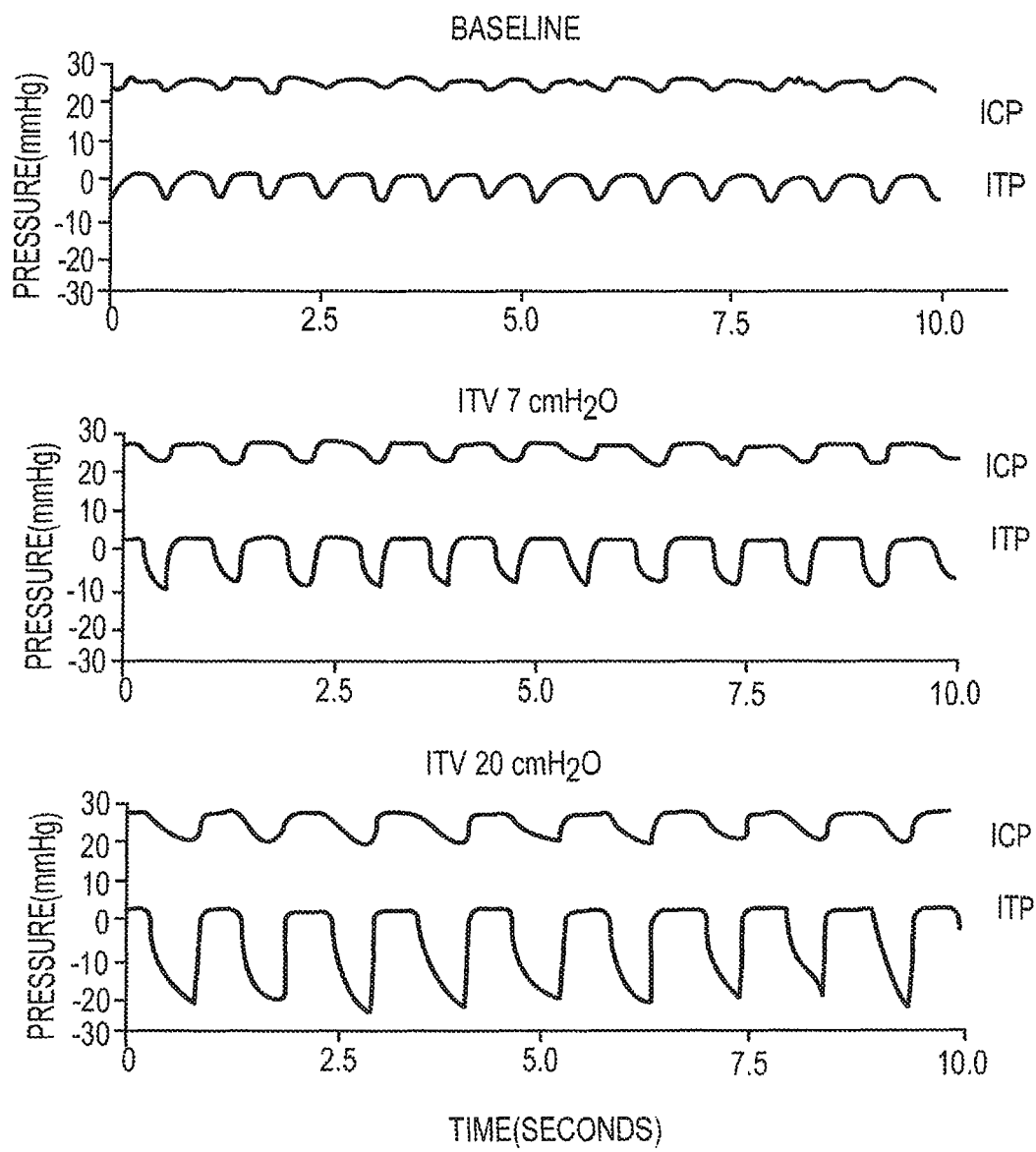
FIG. 8 is a series of graphs illustrating the lowering of intracranial pressures in another animal study.

At base, the intracranial pressure was approximately 8/4 mmHg. With increasing amounts of inspiratory impedance, the intracranial pressure was lowered proportionally as shown in FIG. 7. The intracranial pressure was 6/−2 mmHg when the pig breathed through an impedance of 20 cm $H_2O$. These findings were observed in multiple pig studies and were reproducible. Next, the Millar catheter was inserted 3 cm into the pig's brain. The intracranial pressure increased secondary to the trauma associated with the insertion of the probe. The intracranial pressure increased to 25/22 mmHg at the new baseline. Next, the impedance threshold valve was evaluated at different levels of resistance (FIG. 8). Again, there was a decrease in intracranial pressure proportional to the degree of inspiratory impedance.

Example 2

In this example, intracranial pressures were increased in the setting of recovery from cardiac arrest. The example used a pig model with ventricular fibrillation for 6 minutes followed by cardiopulmonary resuscitation for 6 minutes, followed by defibrillation. Spontaneous breathing resulted in an up to 50% decrease in intracranial pressures when the animals breathed through an inspiratory impedance of 10 cm $H_2O$ using a valve system similar to Example 1.

In all examples above, the intrathoracic pressure decreased relative to the rest of the body, creating a suction effect that reduced the pressure in the venous blood vessels draining the brain, thereby reducing intracranial pressures.

The invention further provides techniques and devices for reducing intracranial pressure (ICP) by facilitating movement of cerebral spinal fluid (CFS). There are a number of causes of increased ICP including: head injury, ischemia, osmolar imbalance, cerebral edema, tumors, complications of dialysis, infections, stroke, hypertensive crises. Each can result in a slow, and in some cases, an acute rise in the ICP. The solid matter of the brain contents makes up about 80-85% of the material enclosed by the skull. Cerebral blood volume accounts for 3-6% and CSF for 5-15%. See, Anesthesia, Third Edition Editor, Ron Miller. Chapter authors: Shapiro and Drummond. Chapter 54 (1990), the complete disclosure of which is herein incorporated by reference. CSF moves within the brain from its site of production to its site of reabsorption in the brain in an unimpeded manner under normal physiological states. Since the contents in the brain are practically incompressible, a change in volume of any one of the three major components (brain matter, blood volume, CSF volume) results in a reciprocal change in one or both of the other brain components. When the volume of the brain expands, secondary to an increase in the non-CSF component(s), some of the CSF is forced to other locations, including through the foramen magnum (hole in skull connecting skull to space where the spinal cord is located) and into the CSF fluid space surrounding the spinal cord. When the non-CSF components expand in volume or size, the intracranial pressure rises. Normal ICP levels are 10-15 mmHg when supine. At levels greater than 15-20 mmHg, damage to the brain can occur secondary to compression and resultant tissue ischemia (lack of adequate blood flow). A reduction in ICP levels can be achieved by a number of clinical interventions including water restriction, diuretics, steroids, hyperventilation, a reduction of cerebral venous pressure, hypothermia, CSF drainage, and surgical decompression.

Increased ICP results in reduced CSF fluid movement and translocation. CSF fluid production generally remains constant (about 150 ml/day) despite elevated ICP. CSF fluid reabsorption is can be slowed by elevated ICP. By using the valve systems described herein, central venous pressures may be reduced. In turn, this results in a decrease in ICP and results in an increase in CSF fluid movement or translocation and reabsorption. This results in a further reduction in ICP.

The valve systems of the invention may be used in spontaneously breathing individuals, in patients ventilated with negative pressure ventilation or in patients ventilated with a ventilator that causes a decrease in central venous pressures for at least a portion of the respiratory cycle. Each time the intrathoracic pressure is reduced with the valve systems of the invention, there is a concomitant reduction in ICP and an increase in the movement of CSF. In other words, there is an increase in the difference between the peak and trough of the ICP wave form when using the valve systems. The sinusoidal movement occurs in spontaneously breathing people because of the change in pressure in the thorax that is transmitted to the brain via the venous blood vessels. The normally fluctuating CSF pressures (the pressure increases and decreases with each inspiration) are altered by the valve systems. More specifically, the valve systems create a lower trough value thereby creating an overall created change in the ICP with each inspiration. In the non-breathing patient, a similar effect can be produced with the valve systems when used with a variety of ventilator devices, including an iron lung, a phrenic nerve stimulator (such as those described in U.S. Pat. Nos. 6,234,985; 6,224,562; and 6,312,399, incorporated herein by reference), a suction cup on the chest that is used to periodically expand the chest and the like.

Figure 9A:
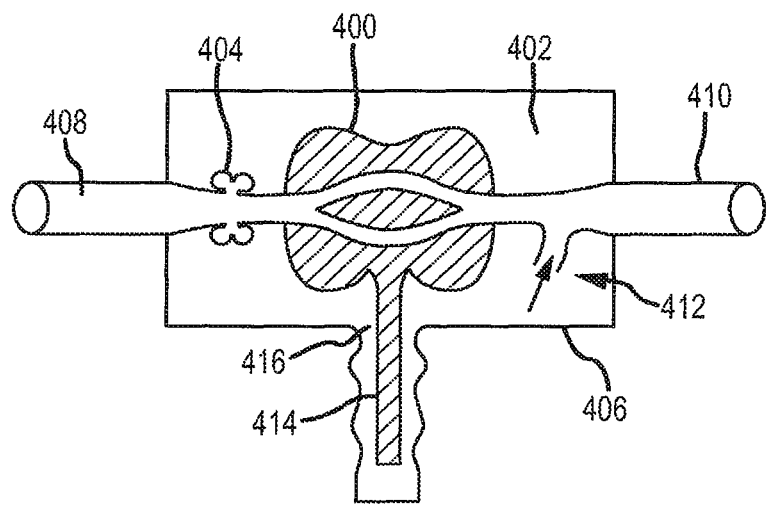
FIG. 9A is a schematic diagram of a person's brain under normal conditions.

Increased CSF fluid movement results in an overall improved metabolic state for the brain. This is shown schematically in FIGS. 9A and 9B. In FIG. 9A, the brain 400 is shown under normal conditions. The brain 400 is surrounded by CSF 402 which is produced at a site 404. The CFS in turn is surrounded by the skull 406. Blood enters brain 400 through an artery 408 and exits through a vein 410. Vein 410 also includes a site 412 of CFS drainage. Shown in FIG. 9A is an arrow showing the direction of CFS flow when draining Extending from brain 400 is the spinal cord 414 that is surrounded by the foramen magnum 416.

Figure 9B:
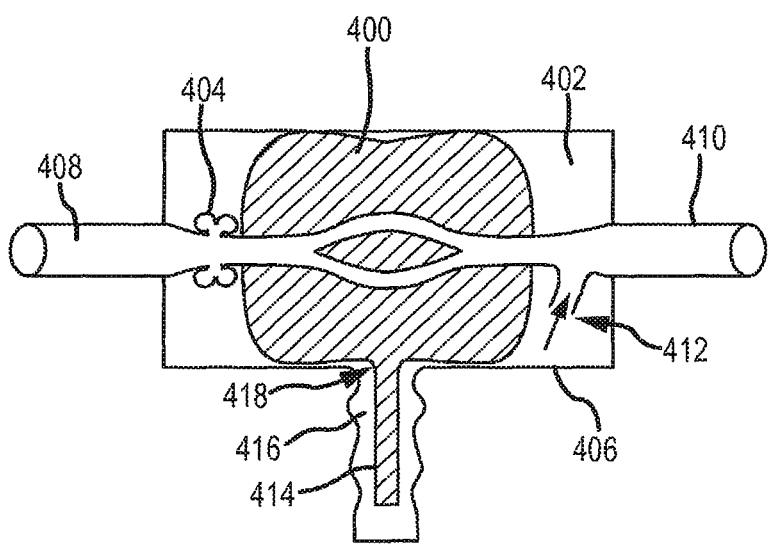
FIG. 9B illustrates the brain of FIG. 9A after increased swelling.

In FIG. 9B, the brain 400 is significantly swollen which reduces the space 402 where the CFS is located. The swelling of the brain 400 can cause blockage of CSF to the spinal cord 414 as shown by arrow 418. Also, movement of CSF to site 412 is reduced to hinder movement of CSF out of the skull 406.

By treating the elevated ICP associated with all of the conditions noted above using the valve systems described herein, brain swelling can be reduced. In so doing, CFS movement and fluid translocation is increased under those same conditions. This results in a further decrease in intracranial pressure as the CSF is able to relocate.

Figure 10:
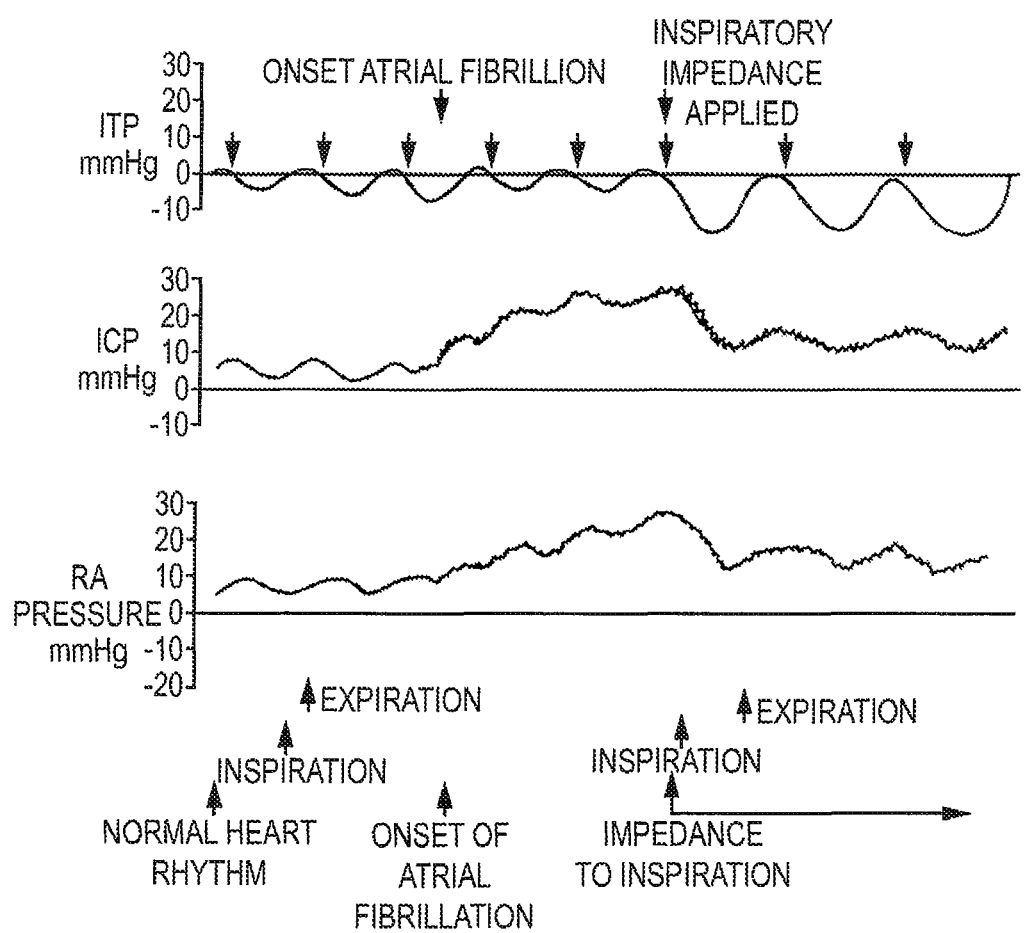
FIG. 10 shows three graphs illustrating the effect of lowering intrathoracic pressure on intracranial pressure and right atrial pressure.

Referring now to FIG. 10, the effects of contracting the atria of the heart on ICP will be described. As shown, contraction of the atria results in a phasic movement in ICP. This can be most clearly demonstrated during cardiac ventricular fibrillation. In that setting, the atria often beat spontaneously and the pressure of each contraction and relaxation waveform is transmitted immediately to the brain and is reflected in nearly identical fluctuations in ICP. The inventor has discovered that the fluid systems (venous blood vessels and CSF) are so closely linked, that subtle changes in the heart rhythm result in immediate changes in CSF pressure. Thus, in some patients with significant heart rhythms, or significant heart failure, the rise in right heart pressures as a result of these conditions results in an increase in ICP. Such rises in ICP can lead to a decrease in cerebral perfusion, since cerebral perfusion is determined by the pressure of the blood entering the brain (mean arterial pressure) minus the pressure of the blood leaving the brain (ICP and central venous pressure). Use of the valve and intrathoracic vacuum systems described herein will result in a decrease in intrathoracic pressure. As shown in FIG. 10, the downwardly pointing arrows represent the timing of each inhalation through the valve system. In the baseline state, before the onset of atrial fibrillation, each inspiration (small arrows) results in a reduction in ITP, a reduction of right atria pressure, a reduction in central venous pressures, and then an immediate reduction in ICP. With the onset of atrial fibrillation, the intracranial pressure rises and the sinusoidal pattern of ICP amplitude changes becomes dampened. As soon as the animal begins to inspire through an inspiration impedance of −10 cm $H_2O$ there is an immediate decrease in intrathoracic pressure (ITP), an immediate decrease in right atrial (RA) pressures, and an immediate decrease in intracranial pressure (ICP) along with the restoration of a sinusoidal fluctuation in ICP with each inspiration. With elevated ICP, inspiration through the impeding means results in a decrease in ICP, increased cerebral spinal fluid flow, and a decrease in cerebral ischemia secondary to increased cerebral perfusion. As such, the valve systems can used in patients with heart rhythms, such as atrial fibrillation, or patients with heart failure who have increased ICP in order to reduce their ICP, increase CSF fluid movement and translocation, and ultimately help them to improve their brain function.

Hence, the amount of inspiratory resistance, or the amount of negative intrathoracic pressure generation (which may be generated using a variety of techniques) can be controlled or regulated by feedback from measurement of ICP, blood pressure, respiratory rate, cardiac output, or other physiological parameters. Such a system could include a closed loop feedback system.

Figure 11:
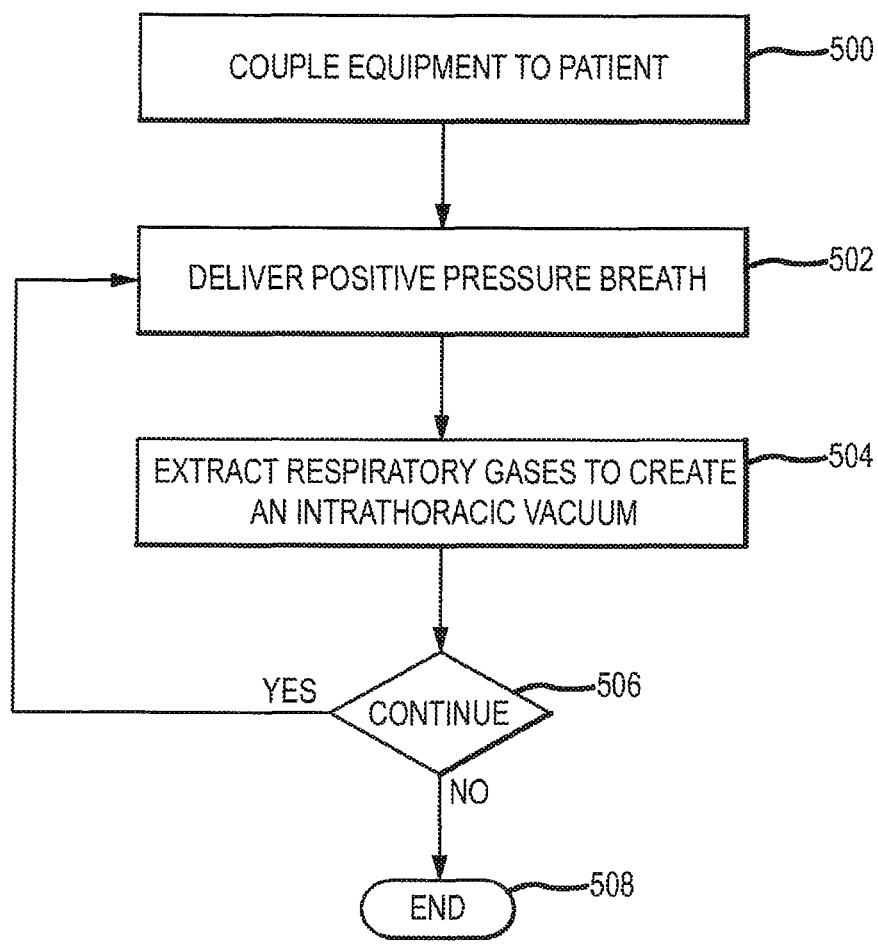
FIG. 11 is a flow chart illustrating another method for reducing intracranial and intraocular pressures according to the invention.

FIG. 11 is a flow chart illustrating another method for treating a person suffering from head trauma associated with elevated intracranial pressures. In so doing, it will be appreciated that such techniques may also be used to treat those suffering from low blood pressure or those in cardiac arrest, among others. The techniques are particularly useful in cases where the person is not breathing, although in some cases they could be used for breathing patients as well.

In a broad sense, when treating a person suffering from head trauma, a person's intrathoracic pressure is lowered to decrease intracranial pressures. In turn, this assists in reducing secondary brain injury. As shown in step 500, equipment may be coupled to the person to assist in lowering the person's intrathoracic pressure. A wide variety of equipment and techniques may be used to decrease the intrathoracic pressure, including using a mechanical ventilator capable of extracting respiratory gases, such as the one described in U.S. Pat. No. 6,584,973, a phrenic nerve or other muscle stimulator (with or without the use of an impedance mechanism, such as those described in U.S. Pat. Nos. 5,551,420; 5,692,498; 6,062,219; 5,730,122; 6,155,257; 6,234,916 and 6,224,562) such as those described in U.S. Pat. Nos. 6,234, 985; 6,224,562; 6,312,399; and 6,463,327, an iron lung device, a thoracic vest capable of pulling outward on the chest wall to create an intrathoracic vacuum similar to the effect of an iron lung, a ventilatory bag, such as the one described in copending U.S. application Ser. No. 10/660, 366, filed Sep. 11, 2003 and the like. The complete disclosures of all these references are herein incorporated by reference. For breathing patients, a threshold valve as described above and that is set to open when about 5 cm $H_2O$ is generated during an inhalation may be used to enhance the person's negative intrathoracic pressure.

When the person is not breathing, a positive pressure breath is delivered to the person as illustrated in step 502. This may be done with a mechanical ventilator, a ventilatory bag, mouth to mouth, and the like. This is followed by an immediate decrease in intrathoracic pressure. This may be done by extracting or expelling respiratory gases from the patient's lungs as shown in step 504. Any of the techniques described above may be used to lower the intrathoracic pressure. Such a reduction in intrathoracic pressure also lowers central venous pressure and intracranial pressure.

The vacuum effect during the expiratory phase may be constant, varied over time or pulsed. Examples of different ways to apply the vacuum are described later with respect to FIGS. 12A-12C. The initial positive pressure breath may be supplied for a time of about 250 milliseconds to about 2 seconds, and more preferably from about 0.75 seconds to about 1.5 seconds. The respiratory gases may be extracted for a time that is about 0.5 to about 0.1 to that of the positive pressure breath. The positive pressure breath may be delivered at a flow rate in the range from about 0.1 liters per second to about 5 liters per second, and more preferably from about 0.2 liters per second to about 2 liters per second. The expiratory flow (such as when using a mechanical ventilator) may be in the range from about 0.1 liters per second to about 5 liters per second, and more preferably from about 0.2 liters per second to about 2 liters per second. The vacuum may be maintained with a negative flow or without any flow. The vacuum may be in the range from about 0 mmHg to about −50 mmHg, and more preferably from about 0 mmHg to about −20 mmHg.

As shown in step 506, the process of delivering a positive pressure breath and then immediately lowering intrathoracic pressures may be repeated as long as necessary to control intracranial pressures. Once finished, the process ends at step 508.

Figure 12A:
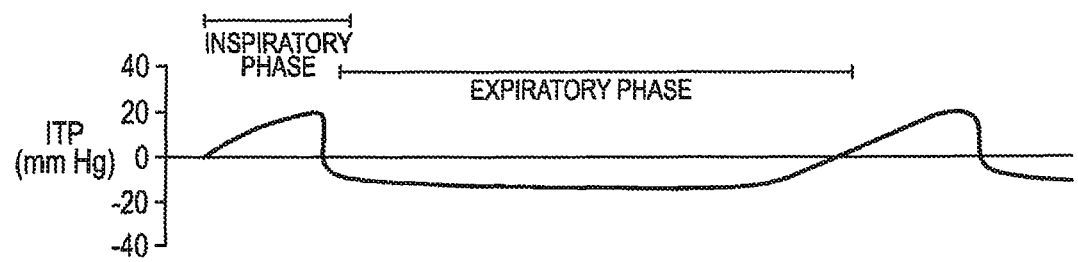
FIGS. 12A-12C show three graphs illustrating patterns for delivering a positive pressure breath and extracting respiratory gases according to the invention.
Figure 12B:
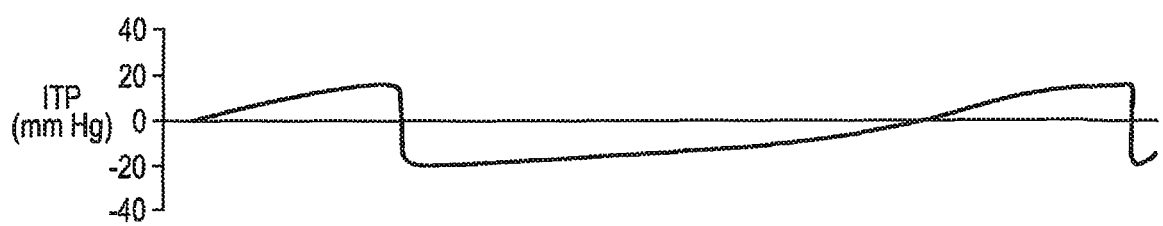
Figure 12C:
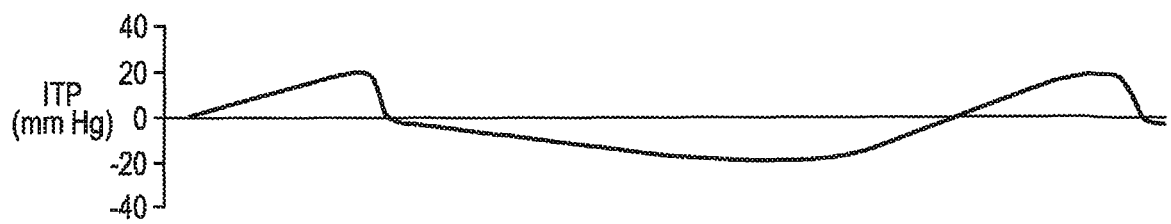

The manner in which positive pressure breaths and the vacuum are created may vary depending upon a particular application. These may be applied in a variety of waveforms having different durations and slopes. Examples include using a square wave, biphasic (where a vacuum is created followed by positive pressure, decay (where a vacuum is created and then permitted to decay), and the like. Three specific examples of how this may occur are illustrated in FIGS. 12A-12C, although others are possible. For convenience of discussion, the time during which the positive pressure breath occurs may be defined in terms of the inspiratory phase, and the time during which the intrathoracic pressure is lowered may be defined in terms of the expiratory phase. The positive pressure breaths may occur at about 10 to about 16 breaths per minute, with the inspiratory phase lasing about 1.0 to about 1.5 seconds, and the expiration phase lasing about 3 to about 5 seconds. As shown in FIG. 12A, respiratory gases are quickly supplied up to a pressure of about 22 mmHg. This is immediately reversed to a negative pressure of about −10 mmHg. This pressure is kept relatively constant until the end of the expiratory phase where the cycle is repeated.

In FIG. 12B, the positive pressure is more slowly applied. When reaching a pressure of about 10 to about 15 mmHg, the pressure is rapidly reversed to a negative pressure of about −20 mmHg. The negative pressure gradually declines to about 0 mmHg at the end of the expiratory phase. The cycle is then repeated. Hence, in the cycle of FIG. 12B, the positive pressure is reduced compared to the cycle in FIG. 12A, and the negative pressure is initially lower, but allowed to gradually increase. The technique is designed to help reduce a possible airway collapse.

In FIG. 12C, the positive pressure is brought up to about 20 mmHg and then immediately brought down to about 0 mmHg. The negative pressure is then gradually increased to about −20 mmHg toward the end of the expiratory phase. This cycle is designed to help reduce a possible airway collapse.

FIGS. 13A and 13B schematically illustrate one embodiment of a device 500 that may be used to lower intrathoracic pressures in a non-breathing patient. Device 500 comprises a housing 502 having an interface opening 504 that may be directly or indirectly coupled to the patient's airway using any type of patient interface. Housing 502 also includes a vacuum source interface 506 that may be in fluid communication with any type of device or system capable of producing a vacuum. Also coupled to housing 502 is a means to regulate the vacuum, such as a pressure responsive valve system 508. Device 500 further includes a ventilation interface 510 that may be used to provide a breath to the patient, if needed, when the vacuum is not applied.

In this embodiment, the vacuum may be provided by essentially any type of a vacuum source, and the regulator may comprise an impedance valve, such as those described in U.S. Pat. Nos. 5,551,420; 5,692,498; 6,062,219; 5,730,122; 6,155,257; 6,234,916; 6,224,562; 6,234,985; 6,224,562; 6,312,399; and 6,463,327 as well as others described herein. To supply a breath, a variety of ventilation sources may be used, such as, for example, a bag valve resuscitator, that is coupled to interface 510. Device 500 may further include a mechanism 512 to inhibit the vacuum when delivering a breath to the patient from the bag valve resuscitator. Once the breath is delivered, mechanism 512 operates to permit the vacuum within the thorax to be reapplied. The mechanism 512 used to turn off and on the vacuum source can include a slider switch that moves to close off the branch in housing 500 having the vacuum source as illustrated in FIG. 13B. However, other types of switches or mechanisms may be used. In some cases, the vacuum source may have a controller that is configured to shut off the vacuum when the breath is administered so that mechanism 512 is not needed. Also, a controller and appropriate sensors could be used to sense when the breath is delivered and stopped so that mechanism 512 may be appropriately operated by the controller. After the breath is delivered, mechanism 512 moves back to the position illustrated in FIG. 13A so that the vacuum may be supplied to the patient. When the vacuum reaches a threshold amount, regulator 508 operates to maintain the level of vacuum at about the threshold amount.

FIGS. 14A and 14B illustrate another embodiment of a device 530 that may be used to treat a patient. Device 530 operates using similar principles as device 500 illustrated in FIGS. 13A and 13B. Device 530 comprises a housing 532 having a patient interface 534 that may be coupled to the patient's airway and a vacuum interface 536 that may be coupled to a vacuum source. Housing 532 also includes a ventilation interface 538 through which a positive pressure breath may be supplied. Also coupled to housing 532 is a vacuum regulator 540 that regulates the amount of vacuum supplied to the patient. One example of a flow regulator that may be used is described below with references to FIGS. 15A and 15B. However, it will be appreciated that any of the flow regulators described herein may be used. Disposed within housing 532 is a flow control device 542 that is used orchestrate gas flows through housing 532. Flow control device 542 comprises a cylindrical member 544 that may slide within housing 532 and includes a flow path 546 that permits gas flow between interfaces 534 and 536 when flow control device 542 is in the position illustrated in FIG. 14A. Conveniently, a spring 548 or other biasing mechanism is used to hold flow control device 542 in the home position illustrated in FIG. 14A. Flow control device 542 also includes a flow path 550 illustrated by the arrow in FIG. 14A to permit gas flows between regulator 540 and interface 536.

Hence, when in the home position, a vacuum may be supplied through interface 536 which lowers the person's intrathoracic pressure. If the vacuum becomes too great, gas flows are permitted through regulator 540 to lower the amount of vacuum.

As illustrated in FIG. 14B, flow control device 542 also includes a flow path 552 that passes from interface 538 to interface 534. This permits a positive pressure breath to be supplied to the patient through interface 538. More specifically, as gasses are injected through interface 538, they flow into flow control device 542 causing it to move within housing 532 and compress spring 548. In so doing, flow path 546 closes as it becomes blocked by housing 532. Flow path 550 also closes, leaving only flow path 552 opened to permit the respiratory gases to flow to the patient. When the positive pressure breath stops, spring 548 forces flow control device back to the home position where the vacuum is once again supplied to the patient.

Hence, when a vacuum is applied from interface 536, air is pulled out of the patient through interface 534 until the cracking pressure of the impedance valve 540 is reached. At that point air passes through impedance valve 540 from the ventilation source at interface 538, thereby setting the limit of the vacuum achieved in the patient. When positive pressure ventilation is delivered from the ventilation source at interface 538, the internal slider switch cylinder 542 moves downward to close off the vacuum source, allowing for delivery of a positive pressure volume to provide a breath to the patient. Flow control device 542 may include a cup-shaped opening 556 which helps to move the device 542 along with minimal force applied. Once the breath has been delivered, and there is no positive force delivered from the ventilation source to the device 542, spring 548 pushes upwards, re-exposing the patient to the vacuum source.

Device 530 may also include an optional pressure pop-off regulator 560. In the event that the vacuum source is too great, the pop-off regulator 560 opens allowing for pressure relief above the desired vacuum pressure. The pop-off regulator 560 may be configured to open for pressures greater than about 20 to about 100 mmHg.

Although the devices illustrated in FIGS. 13 and 14 are shown with mechanical switching mechanisms (to turn the vacuum off and on), others may also be used, such as magnetic, electronic, or electrical. Other kinds of possible switches include a ball valve, flapper valve, fish mouth valve, or other mechanical means as well as electric or electronic valving systems, including a solenoid, to allow for temporary inhibition of the vacuum once the positive pressure breath is delivered from the ventilation source. Additional regulators can also be used on the vacuum source to limit the flow or force of the vacuum. For example, the vacuum source could be configured to provide a constant vacuum once a threshold level has been achieved. In addition, the vacuum regulator and impedance valves 508 and 530 may be variable or set at a fixed level of impedance. The vacuum source may also be a suction line or come from a venture device attached to an oxygen tank that could both provide oxygen to the patient and a vacuum source. Further, the invention is not limited to using an impedance valve, as shown, to regulate the vacuum. Multiple switching and regulating means may be used instead. The ventilation source is similarly not limiting and may include sources such as mouth-to-mouth, a bag-valve resuscitator, an automatic ventilator, and the like.

Figure 15A:
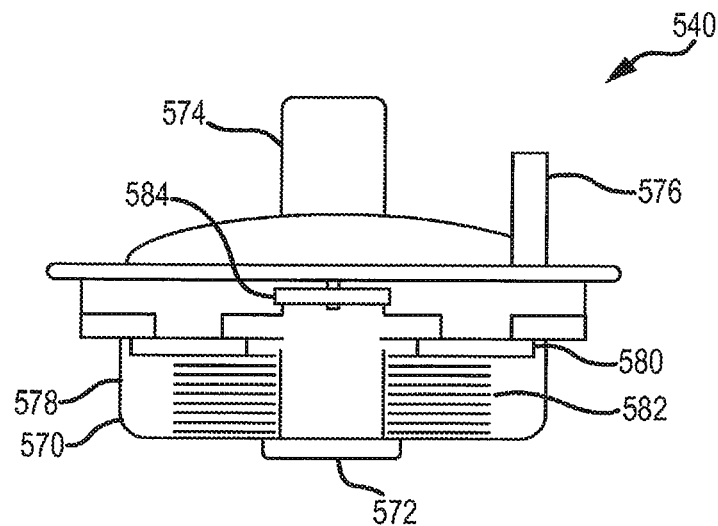
FIGS. 15A and 15B illustrate one embodiment of a threshold valve system that may be used with the device of FIGS. 14A and 14B.
Figure 15B:
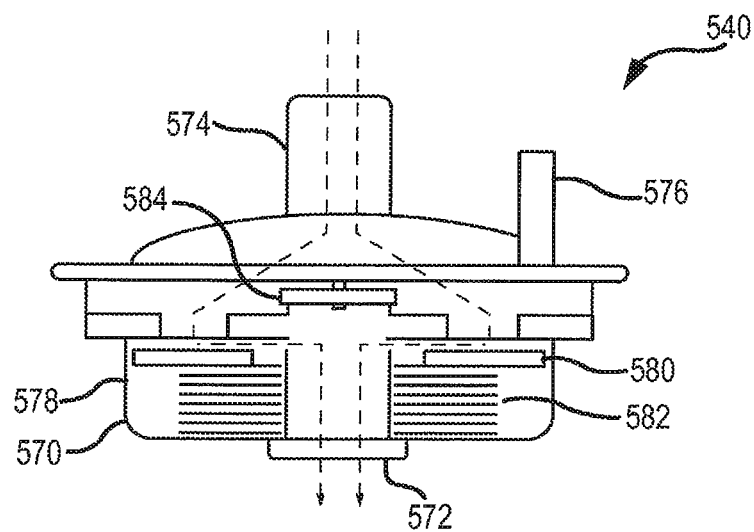

FIGS. 15A and 15B illustrate flow regulator 540 in greater detail. Regulator 540 comprises a housing 570 having a patient port 572 and a ventilation port 574. Optionally, a supplemental oxygen port 576 may also be provided. Gas may flow through housing 570 (between ports 572 and 574) through one of two flow paths. The first flow path is blocked by a one way check valve 578 that comprises a check valve gasket 580 and a spring 582. The second flow path is blocked by a diaphragm 584.

In operation, a vacuum is experienced at patient port 572 as the vacuum source draws a vacuum at port 536 (See FIG. 14A). When the vacuum reaches a threshold level, spring 582 compresses to move gasket 580 downward, thereby creating a flow path as illustrated in FIG. 15B. As the vacuum is pulled, diaphragm 584 closes to prevent air from flowing through the other flow path. Gasket 580 remains spaced apart from the opening as long as the vacuum is at the threshold level. In this way, regulator 540 is able to maintain the vacuum at a constant level.

When ready to ventilate the patient, the vacuum is stopped and respiratory gases are injected into port 574 and/or port 576. These gasses lift diaphragm 584 to permit the gases to flow to the patient.

Example 3

Example 3 is another non-limiting example illustrating how intracranial pressures and intrathoracic pressures may be lowered and systolic arterial pressure may be increased according to one aspect of the invention. In this example, 30 kg pigs were anesthetized with propofol. Using a micromanometer-tipped electronic Millar catheter inserted 2 cm below the dura, intracranial pressures were measured in non-breathing pigs. Intrathoracic pressures (ITP) were recorded using a Millar catheter placed in the trachea at the level of the carina. Systolic aortic blood pressures (SBP) were measured in the aorta with a Millar catheter. To regulate intrathoracic pressures, a system similar to that illustrated in FIGS. 14A, 14B, 15A and 15B was used, with inspiratory impedance (−8 cm $H_2O$ with a flow rate of 30 L/min). Positive pressure ventilation was provided at a rate of 10 breaths/min with a tidal volume of approximately 400 ml delivered over 1.0 seconds with an automatic transport ventilator. The objectives, methods, results, and conclusions describing these novel cardiopulmonary-cranial interactions are summarized below.

An objective of this example was to evaluate the acute use of a novel inspiratory impedance threshold device (ITD) attached to a controlled but continuous vacuum (CV) source to decrease intrathoracic pressure (ITP) and intracranial pressure (ICP) but simultaneously increase mean arterial pressure (MAP), coronary perfusion pressure (CPP) and cerebral perfusion pressure (CerPP) in an apneic pig model of sequential insults of cardiac arrest and fixed-bleed hemorrhage hypotensive shock. This animal model is associated with both elevated ICP after cardiac arrest and significant hypotension after hemorrhage.

This example used 6 female farm pigs (28-32 kg) that were anesthetized with propofol, intubated and ventilated to maintain normocarbia and O2 saturation >90%. Ventricular fibrillation was induced and followed by 6 min of no treatment, 6 min of standard CPR, and then defibrillation. After return of spontaneous circulation and while ventilated mechanically at 10 breaths/min, 35% of blood volume was removed with a rate of 60 cc/min. Five min later ITD-CV was applied for 5 min along with positive pressure ventilation with 100% oxygen at a rate of 10 bpm. The ITD-CV was then removed and positive pressure ventilation at a rate of 10 breaths/min was reapplied. Hemodynamic parameters and arterial blood gases were assessed before, during, and after ITD-CV application. Statistical analysis was performed with a paired t-test and ANOVA to compare +/−ITD-CV use.

The results are summarized in the Table below. As shown, by regulating thoracic pressures, use of the ITD-CV causes an instantaneous decrease in ITP and ICP as well as a rapid rise in MAP and a marked increase in CerPP. Hence, the ITD-CV may be used to treat hypotension, shock, and cerebral hypertension.

TABLE

| | Before ITD-CV | During ITD-CV | After ITD-CV | p-value |
|---|---|---|---|---|
| ITP | 0.5 ± 0.1 | −12.0 ± 1.1 | 0.1 ± 0.2 | 0.001 |
| MAP | 46.7 ± 5.2 | 54.7 ± 7.7 | 38.3 ± 4.1 | 0.03 |
| ICP | 14.1 ± 3.9 | 6.1 ± 4.5 | 15.4 ± 3.9 | 0.001 |
| CerPP | 32.7 ± 4.2 | 48.6 ± 5.9 | 23.0 ± 4.5 | 0.01 |
| CPP | 40.1 ± 4.5 | 58.4 ± 7.7 | 31.1 ± 3.4 | 0.008 |

In one particular embodiment, a person may have his or her intrathoracic pressure manipulated using multiple techniques, alone or in combination. For example, some type of external thoracic positive pressure source may be used to increase and then decrease the person's intrathoracic pressure to move blood out of and then into the heart and lungs in a repetitive fashion. Examples of such an external thoracic positive pressure source include a mechanical extrathoracic vest, a body cuirass, a compression piston, a compression cup, or the like. Such devices may function as non-invasive hemodynamic support devices for maintenance of increase blood pressure and circulation in hypotensive patients.

While the person's intrathoracic pressures are being externally manipulated (e.g., being increased and decreased), the person may also have his or her intrathoracic pressures manipulated by applying positive pressure breaths and a vacuum using any of the techniques described herein. Further, any of the valve systems described herein may be used in combination as well. Hence, while the person's chest is being compressed and relaxed, positive pressure breaths followed by a vacuum may be applied at the same time. In this way, non-invasive techniques are provided for improving blood flow to the vital organs for an indefinite period of time, and may be used in cases where the patient is in shock, has very low blood pressure, those in cardiac arrest, and the like. Also, such techniques may be used to circulate a preservative solution, equivalent to cardioplegic agents, until more definitive care is available.

The timing of each of these steps may be controlled to correlate in any manner, such as, for example, applying the vacuum while the force on the patient's chest is relaxed. Also, the timing of chest compressions could be tied to other variables, such as timing the compressions and/or decompressions with intrinsic cardiac rhythm (i.e., ECG activity). Further, the positive pressure breaths may be performed only as needed and not in association with every chest compression. Further, the chest may be decompressed only after a certain number of chest compressions.

As with other embodiments, the patient may also be supplied with periodic positive pressure ventilation or an extracorporeal oxygenator to provide adequate respiration. Negative pressure ventilation may also be used to provide proper ventilation. For example, the chest may be decompressed with an unimpeded airway to provide the negative pressure ventilation. Also, the techniques just described could also be used alone or in combination with invasive ways to also maintain blood pressure. For instance, a greater effect on intracranial pressure may be produced if some of the patient's blood is removed from the body.

One particular arrangement of a system that may be used with such techniques is set forth in FIG. 6 (previously described) where element 370 (an iron lung cuirass device) may also schematically represent any of the external thoracic positive pressure sources described herein. Further, controller 310 may also include some type of energy source for operating the positive pressure source, such as pneumatic, electronic, combustion or the like. In this way, a variety of energy sources may be used to compress the chest and then release the compression in an alternating manner. Ventilator 360 may be used to apply the positive pressure breath followed by a vacuum using any of the techniques described herein, as well as to provide proper ventilation. Further, although shown with valve system 200, it will be appreciated that any of the other valve systems described herein may be used as well. Also, it will be appreciated that temperature sensor 350 may be substituted with other types of sensors and/or monitors, such as an ECG monitor, so that chest compressions and/or decompressions may be timed with ECG activity.

Intrathoracic Pressure Regulation and Positive End Expiratory Pressure

In an intrathoracic pressure regulation (IPR) technique that involves PEEP, during ventilation, in an inhale/exhale cycle in an apneic person or person needing assisted ventilation, it is possible to provide a positive pressure breath or ventilation (PPV), then provide positive end expiratory pressure (PEEP), and then pull a vacuum. Aspects of such a technique are illustrated in FIG. 16A. Alternatively, it is possible to first provide a positive pressure breath or ventilation, then pull a vacuum, and then supply PEEP. Aspects of such a technique are illustrated in FIG. 16B. According to some embodiments, these treatments may be effected, at least in part, by use of a push/pull ventilator. In some cases, these treatments can be performed in conjunction with a cardiopulmonary resuscitation (CPR) procedure or other approach for treating low blood pressure or low circulation. The duration of PPV, PEEP, and generation of a vacuum within the thorax may vary, depending upon the physiological needs of the patient. In the graphs provided in FIGS. 16A and 16B, pressure vs. time curves are illustrated for novel intrathoracic pressure regulation techniques. Pressure is illustrated in terms of intrathoracic pressure (ITP), airway pressure, or endotracheal pressure, in units of cm $H_2O$. Timing may depend on what the inspiratory:expiratory (I:E) ratio is set to on a ventilator and the setting for the respiratory rate. In the examples depicted here, the I:E ratio is 1:3, or one in three, with a respiratory rate of 10 breaths per minute. In some cases, the I:E ratio can be anywhere within a range from about 1:1 to about 1:4. In some cases, the respiration rate can be within a range from about 6 to about 30 breathes per minute. The addition of PEEP may provide additional oxygenation for a diseased or compromised lung, more than just the positive pressure breath does. In some cases, PEEP is provided via mechanical ventilation and the degree and duration of PEEP may be variable or fixed, and may be regulated with a closed loop control system. In some cases PEEP can refer to pressure greater than atmospheric pressure that is present in the airway during or at the end of the expiratory cycle. The delivery of a positive pressure breath can be performed using a mechanical ventilator or anesthesia machine. The value of time t, which corresponds to the duration of the PEEP administration, can be within a range from about 0.1 second to about 1.5 seconds, for example. In some cases, the positive pressure breath can be delivered to the patient for a time period within a range from about 250 milliseconds to about 2 seconds. In some cases, the positive pressure breath can be delivered to the patient a rate within a range from about 0.1 liters per second to about 5 liters per second. The time that the positive pressure breath is supplied relative to the time in which PEEP and/or vacuum can be within a range from about 0.5 to about 0.1. When the person is not breathing, a positive pressure breath can be delivered to the person. This may be done with a mechanical ventilator, a ventilatory bag, mouth to mouth, and the like. Any of the inspiratory impedance threshold device (ITD) techniques encompassed by the instant application can be used in conjunction with this method. It is also understood that approaches encompassed by the instant application can be used in conjunction with diabetes treatment modalities, such as those described in U.S. patent application Ser. No. 10/401,493 filed Mar. 28, 2003 and Ser. No. 11/735,320 filed Apr. 13, 2007, the contents of which are incorporated herein by reference. Approaches encompassed by the instant application can be used in conjunction with treatment modalities for heart failure and other conditions, such as those described in U.S. Pat. Nos. 5,551,420, 5,692, 498, 6,062,219, 6,526,973, 6,604,523, 7,210,480, and 6,986, 349, the contents of which are incorporated herein by reference. The pressure curves shown in FIGS. 16A and 16B may in some cases be achieved by incorporating the use of a ventilator or anesthesia machine. Relatedly, in some cases such curves may be achieved without the use of a ventilator. Any of a variety of mechanisms or procedures may be used to decrease ITP or achieve negative ITP, including without limitation a vacuum source, a suction device, a push/pull ventilator, or an active compression-decompression device.

Figure 17:
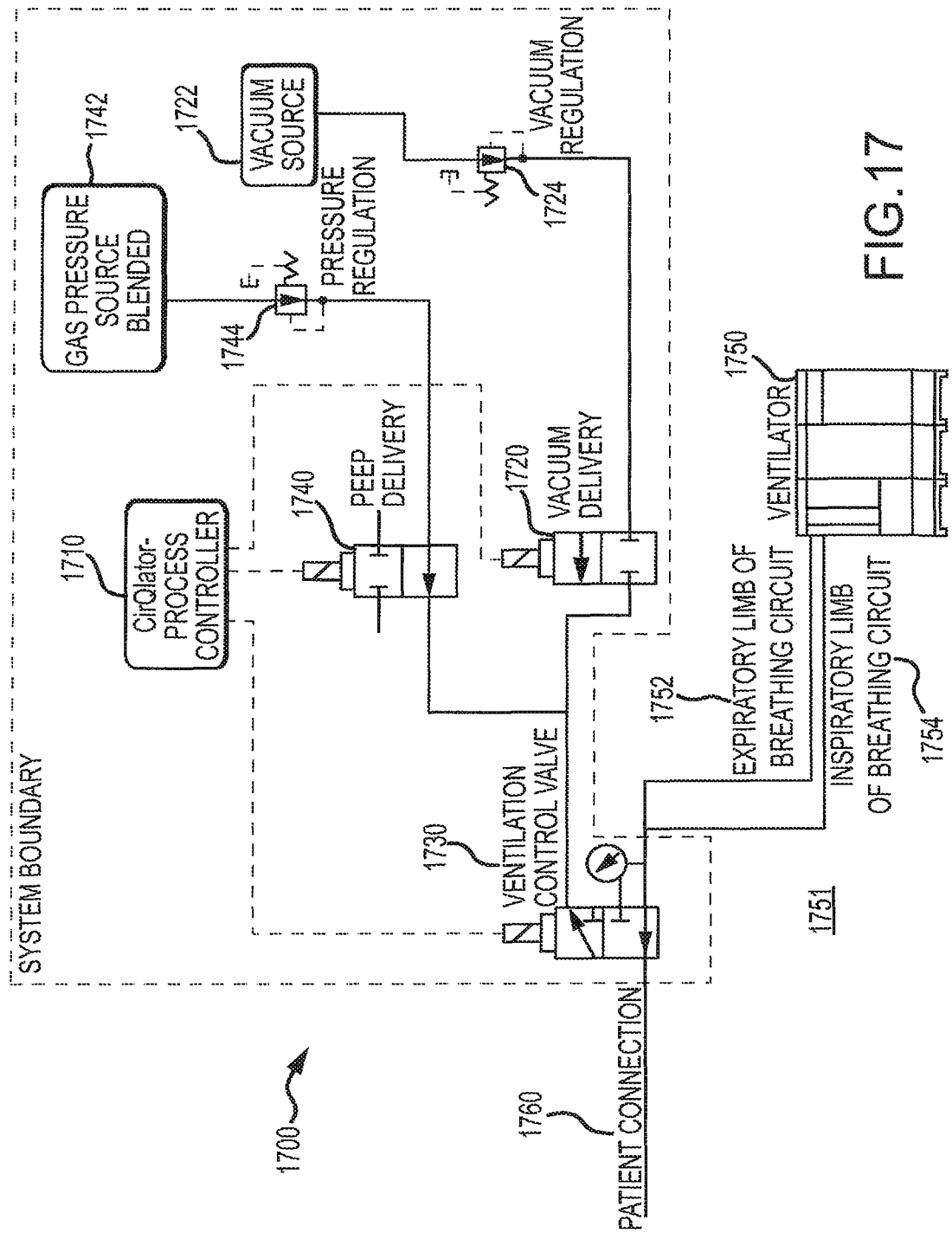
FIG. 17 schematically illustrates a system for administering a pressure regulation treatment to a patient, according to embodiments of the present invention.

FIG. 17 provides a schematic for an exemplary system for administering a treatment to a patient. As shown here, system 1700 includes a process controller 1710 in operative association with a vacuum delivery apparatus 1720, a ventilation control valve apparatus 1730, and a PEEP delivery apparatus 1740. Vacuum delivery apparatus 1720 is in operative association with a vacuum source apparatus 1722, optionally via a vacuum regulation apparatus 1724. PEEP delivery apparatus 1740 is in operative association with a gas pressure source blended apparatus 1742, optionally via a pressure regulation apparatus 1744. Ventilation control valve apparatus 1730 is in operative association with a ventilator apparatus 1750, optionally via a breathing circuit apparatus 1751 having an expiratory limb apparatus 1752 and an inspiratory limb apparatus 1754. PEEP delivery apparatus 1740 can be configured to deliver an adjustable amount of PEEP as desired. As shown here, system 1700 can also include a pressure transducer 1731. System 1760 also includes a patient connection apparatus 1760 which can be coupled to a patient, for example via an endotracheal tube or other patient airway device.

According to some embodiments, a treatment method may include a first step that involves releasing the ventilation control valve apparatus 1730 to deliver positive pressure ventilation. The treatment method may also include a second step that involves activating the ventilation control valve apparatus 1730 and the vacuum delivery apparatus or valve 1720, at the end of the positive pressure breath. The PEEP delivery apparatus or valve 1740 can be released, delivering positive end expiratory pressure to the patient from internal gas blender apparatus 1742 at a regulated pressure. The treatment method may further include a third step that involves energizing the PEEP valve 1740 and deenergizing the vacuum delivery valve 1720 at the end of the PEEP stage, to generate a regulated vacuum to the patient's airway. The treatment method may also include repeating the first, second and third steps described above. In some cases, ventilator 1750 can be used to deliver a positive pressure ventilation or breath, a vacuum, or both, to the patient. According to some embodiments, a manual resuscitator can be used to deliver a positive pressure breath to the patient. Additional operational aspects of a ventilator are discussed elsewhere herein, for example, with in conjunction with FIGS. 19A-19F.

Intrathoracic Pressure Regulation Effect on Sympathetic Tone

An intrathoracic pressure regulator (ITPR) can combine an inspiratory impedance threshold device (ITD) with a vacuum source for the generation of vacuum, for example in the trachea during cardiopulmonary resuscitation (CPR) while allowing positive pressure ventilation. Use of an ITPR can modulate the autonomic system. During inhalation a valve system can function to produce a vacuum within the thorax to transiently decrease intrathoracic pressure and thereby modulate the person's autonomic function. More specifically, by lowering the intrathoracic pressure, the person experiences enhanced venous return of blood to the heart, and this causes an increase in cardiac output, an increase in blood pressure, and increase in blood flow to the brain, a decrease in intracranial pressure, and an autonomic nervous system-modulated decrease in sympathetic tone resulting in a decrease in peripheral arterial resistance. The resultant increase in venous blood flow back to the right heart and then into the lungs increases cardiac preload and facilitates the refilling of the right and left chambers of the heart. The subsequent cardiac contract results in an increase in cardiac stroke volume and cardiac output. This causes the body's receptors, such as the carotid baroreceptors in the neck, to sense the increase in blood pressure and circulation and alter the autonomic nervous system balance. This can be demonstrated by the shift from lower frequency power spectra from electrocardiograms recorded from skin electrodes that are analyzed using standard heart rate variability analytic methods. Approaches encompassed by the instant application can be used in conjunction with treatment modalities such as those described in U.S. Pat. No. 7,195,013, the content of which is incorporated herein by reference.

Hence, the use of intrathoracic pressure regulation (IPR) can modulate the autonomic nervous system. In some cases, when IPR therapy is applied when the thorax has been opened, for example during open heart surgery, the lungs are filled with respiratory gases during the positive pressure phase (inspiration) and during the expiratory phase respiratory gases are actively extracted from the lungs. This results in the rapid displacement of blood within the lungs into the left atrium, thereby priming the left heart with blood. By alternately filling the lungs with respiratory gases and providing space concurrently for blood from the right heart, and then extracting respiratory gases and propelling the blood within the lung reservoir forward, the lung serves as a peristaltic sponge to both suck up blood from the right heart and deliver it to the left heart. By 'wringing out the sponge' the expansion and contraction of the lung parenchyma provides a novel means to propel blood forward in the setting of low or reduced blood circulation. The addition of PEEP either before or after this 'wringing out' process provides a means to help maintain oxygenation and preserve and protect lung function. During this process the delivered tidal volume during the inspiratory phase may vary and the rate of respiratory gases removal by the method or device may vary, either directly or indirectly with the tidal volume delivered, thereby providing a means to achieve the desired target airway pressures and/or intrathoracic pressures. Methods and devices such as these that provide IPR therapy can therefore be used to enhance circulation and increase blood pressure, even when the thorax is open to atmospheric pressure such as during or after open heart surgery. It can be applied to both lungs or just one lung, as long as the method and device is allowed to move respiratory gases in and out of the lung(s).

The changes in pressures in the lung achieved with IPR therapy are a direct result of changes in lung respiratory gas volume. With each positive pressure ventilation the gas volume is increased and when it is actively extracted it is reduced. In the process blood is squeezed out of the lungs and blood can only move forward due to the intact one-way valves within the heart (pulmonic and mitral in this case). Thus blood is pumped out of the lungs, which served as a giant reservoir, during the gas extraction phase and when the lungs are inflated respiratory gases fill the alveoli of the lungs and indirectly restore the arterial and venous bed architecture so that blood from the right heart rushes into the lung blood reservoir as soon as the lungs are inflated. The active infusion and removal of respiratory gases by the IPR therapy provides a novel means to pump blood into the left heart. When the chest is open to atmospheric pressure, then changes in lung volumes do not alter intracranial pressures as the pressures within the non-lung structures in the thorax no longer vary with changes in airway or lung pressures.

Embodiments of the invention can therefore be used to treat patients suffering from a number of disease states including but not limited to those suffering from elevated intracranial pressures, intra-ocular pressures, shock, hypotension, circulatory collapse, cardiac arrest, heart failure, intra-operative hypotension, and those in dialysis. It can also lower venous pressures within the abdomen during surgical procedures such as operations on the liver or intestines, and simultaneously provide greater blood flow to these and other vital organs such as the kidneys, brain, and heart. By lowering venous pressures it can help to reduce blood loss during surgical procedures. By the aforementioned described mechanisms the novel methods and devices can also treat hypotension and poor circulation associated with sepsis, poly-traumatic organ damage, and acute respiratory disease syndrome (ARDS). Embodiments of the intention may also be used to reduce venous pressure in 'compartment syndrome' and therefore help to circulate more blood and preserve tissue viability and function. Embodiments of the invention can be based upon the discovery that reductions in intrathoracic pressure result in a decrease in intracranial pressures and enhancement of blood flow to the heart. In patients with an open thorax, device embodiments can lower pressure in the airway and in the lungs, thereby removing respiratory gases from the lungs. This results in a 'wringing out' of the lungs much like a wet sponge with each application of the vacuum and this forces the blood in the lungs into the left heart as the pulmonic valve prevent reverse transpulmonary flow. With the next inspiration, respiratory gases fill the lungs and blood rushes into the lungs. It is squeezed out with the next application of the low level vacuum. As such, the changes in airway pressure provide a pulmonary pump to squeeze blood out of the lungs and with each positive pressure breath provide an empty vascular reservoir within the lungs that is rapidly refilled from blood within the right heart.

When the thorax is not intact device embodiments may also include a mechanism for varying the level of resistance of the valve system. For example, embodiments may include adding positive expiratory pressure. This device may be used in combination with at least one physiological sensor that is configured to monitor at least one physiological parameter of the person. In this way, the mechanism for varying the pressures and/or volume of respiratory gases within the lungs may be configured to receive signals from the sensor and to vary the level of impedance of the valve system based on the signals. This in turn regulates the amount of respiratory gas volume and/or pressure and the speed at which the gases are actively infused into and extracted from the lungs. Examples of sensors that may be used include those that measure, airway pressure, intratracheal pressure, blood pressure, right heart pressure, heart rate, end tidal $CO_2$, oxygen level, and left heart pressures.

As noted elsewhere herein, embodiments of the present invention are well suited for use in decreasing intracranial or intraocular pressures when the patient's thorax is intact. Such techniques can be employed with the open chest. Lung volume and pressure can change without a change in intrathoracic pressure, as the circuit is open. When the chest is open this approach typically does not lower intracranial pressures.

In some cases PEEP can be applied either before or after the extraction of the gases. With this approach, the method and device provide a 3-phase means to modulate airway pressures and when the thorax is intact intrathoracic pressure: the lungs are inflated, the gases are removed from the lungs, and the lungs are partially inflated by PEEP to reduce atelectasis and help preserve lung integrity.

Figure 18A:
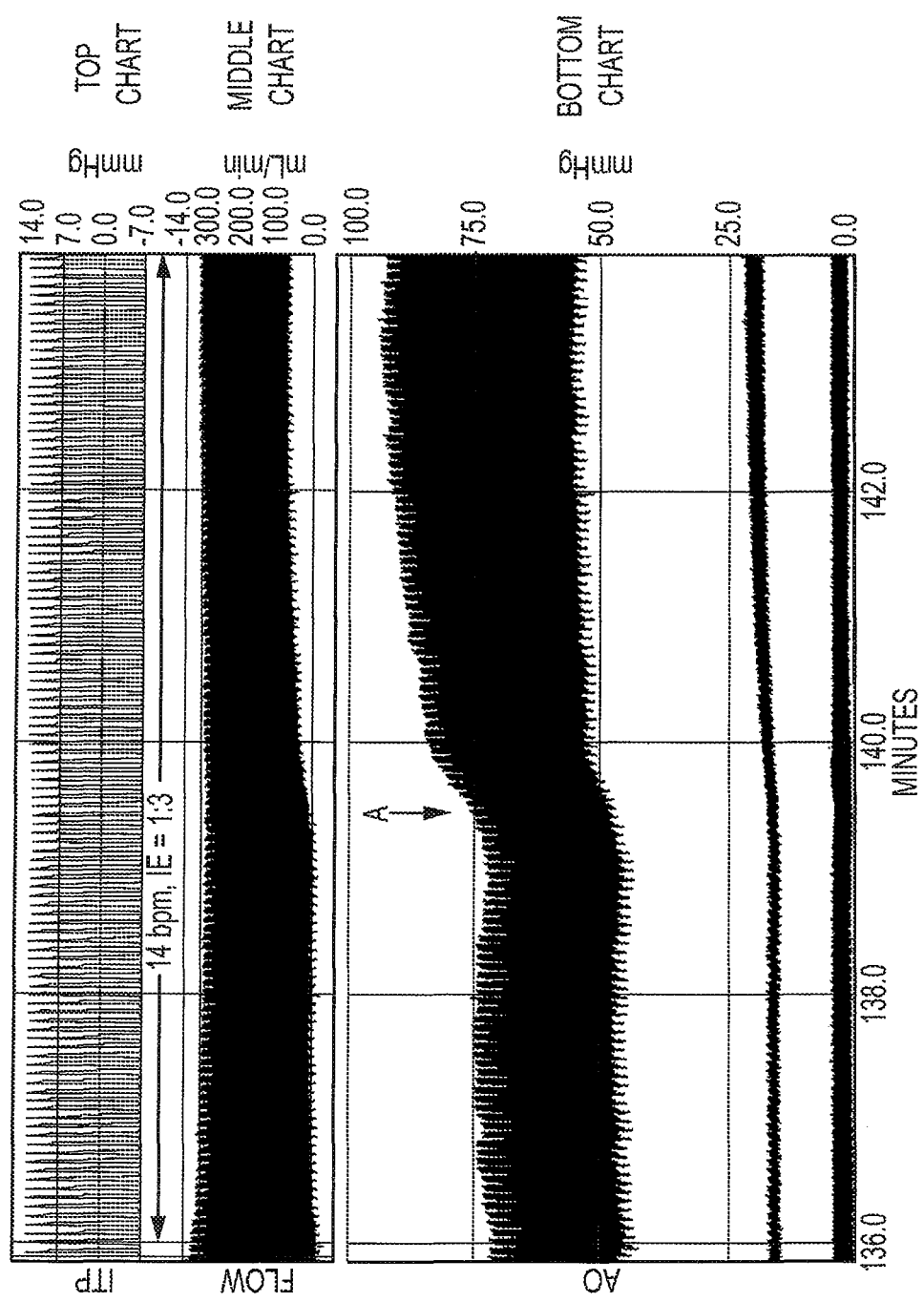
Figure 18C:
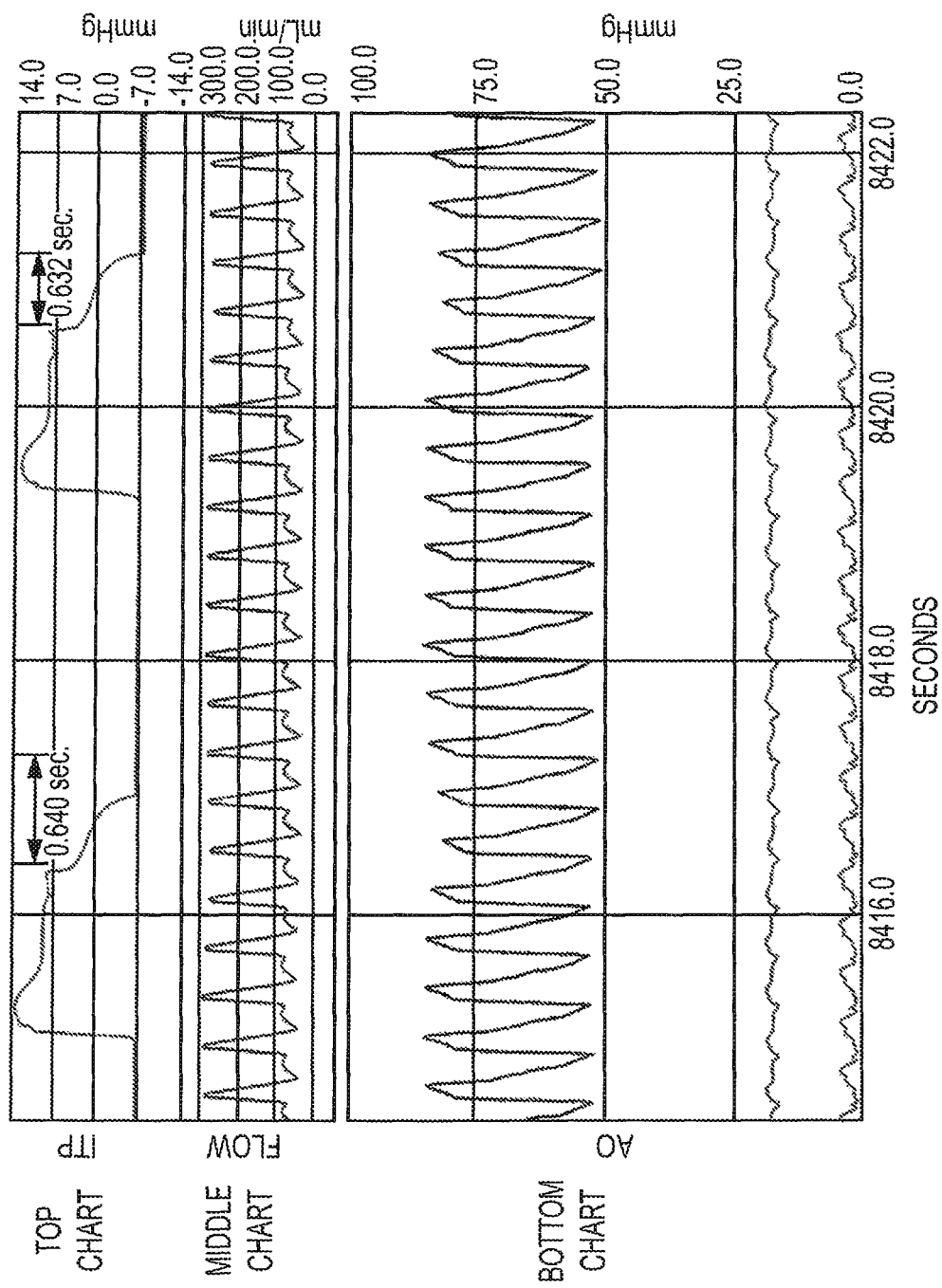

As discussed elsewhere herein, the delivery of the positive pressure breaths and the extraction of gases can be performed using a mechanical ventilator, and the respiratory gases may be extracted with a constant extraction or a pulsed extraction. The speed and volume and pressure of gas infusion and extraction may vary depending upon the patient's condition and needs. For example, when the tidal volume is increased, the speed which the large gas volume is extracted may be varied. This can be important in order to maximize the duration of negative intrathoracic pressure (when the thorax is intact) and airway pressure and lung pressure when the thorax is open. FIGS. 18A-18C show aspects of tidal volume and airway pressure changes.

The top charts of FIGS. 18A-18C show intrathoracic pressure (ITP) in mmHg, as a function of time. The IPR therapy is delivered to generate an intrathoracic vacuum of −7.0 mmHg and the positive pressure breath provides a maximum intrathoracic pressure of 14 mmHg. The middle charts of FIGS. 18A-18C show blood flow in the carotid artery in mL/min (e.g. common carotid blood flow), as a function of time. In FIG. 18A, the bottom chart provides three tracings (top tracing, middle tracing, and bottom tracing). The top tracing of the bottom chart corresponds to blood pressure as a function of time, the middle tracing of the bottom chart corresponds to intracranial pressure as a function of time, and the bottom tracing of the bottom chart corresponds to right atrial pressure as a function of time. FIG. 18B is from a segment around minute 138 in the study represented by FIG. 18A, when the tidal volume was 10 ml/kg, and FIG. 18C is from a segment around minute 140 in the same experiment represented by FIG. 18A. FIG. 18B depicts inspiratory tidal volume (TV) of about 276 ml, and a target of about 27.2 kg×10 ml/kg. FIG. 18C depicts inspiratory tidal volume (TV) of about 192 ml, and a target of about 27.2 kg×7.5 ml/kg. When the tidal volume was reduced but there is no change in the speed at which respiratory gases are removed (as shown in FIG. 18C), then the amount of time the airway pressures are at the target level of −7.0 mmHg is greater, thereby increasing the overall effectiveness of the delivered therapy when compared with the results shown in FIG. 18B.

In this IPR therapy experiment with a 27.6 kg anesthetized pig having an open thorax, initially the pig was ventilated with a positive pressure ventilation at 14 breaths per minute (bpm) and an inspiratory:expiratory ratio (I:E) of 1:3. The IPR therapy was delivered as indicated by the decrease in airway pressures, shown in FIGS. 18A and 18B (top charts). According to these chart tracings, the intrathoracic pressure (ITP) decreases from 14.0 mmHg to −7.0 mmHg at each ventilated breath. The time required to lower the airway pressure to the target value of −7.0 mmHg was 0.84 seconds.

By decreasing the tidal volume (TV) from 276 ml (10 ml/kg) in this 28 kg anesthetized pig (e.g. FIG. 18B) to 192 ml (−7 ml/kg) (e.g. FIG. 18C) as shown by arrow A in FIG. 18A (near minute 139.4 in the bottom chart), the time required to lower airway pressures to the target value of −7.0 mmHg was reduced to 0.64 seconds. This reduced time span is illustrated in FIG. 18C (top chart). With the longer duration of negative airway pressure the blood pressure increased from about 75/42 mmHg (e.g. FIG. 18B, bottom chart, top tracing) to about 95/55 mmHg (e.g. FIG. 18A, bottom chart, top tracing). Blood flow in the carotid artery similarly increased.

According to some embodiments, FIGS. 18A-18C graphically illustrate the removal of respiratory gases (e.g. application of vacuum) that depends upon the amount of tidal volume delivered (e.g. the greater the tidal volume the more slowly the gas can be removed).

Figure 19B:
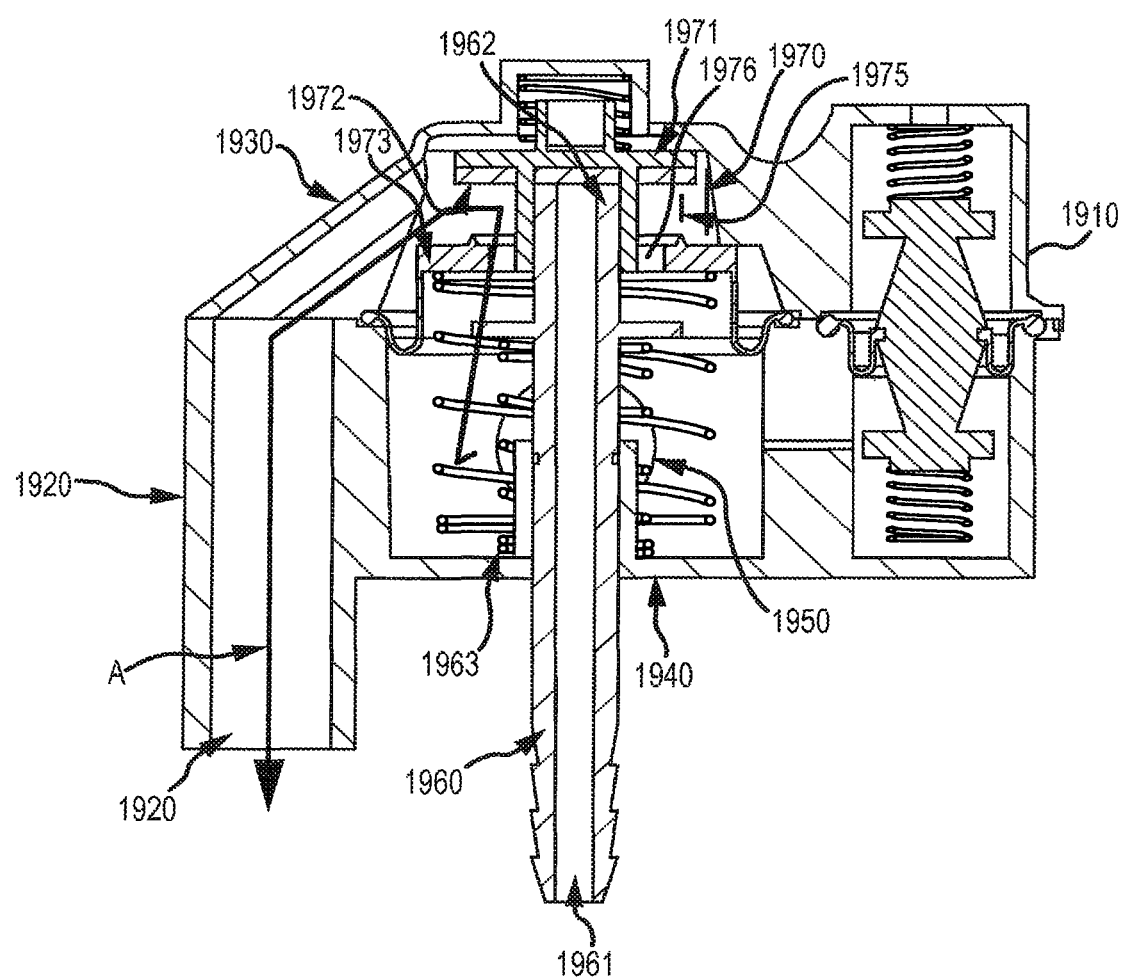

As noted above, an IPR device which is well suited for use with such methods is described in FIGS. 19A-19F. Exemplary IPR devices provide a threshold valve that can regulate vacuum. Shown from one perspective, FIG. 19A-1 depicts an IPR system 1900 having a manometer or pressure sensor 1910, a ventilator port 1920, an inlet cap 1930, a body 1940, a patient port 1950, a vacuum stem 1960, and a valve (not shown). Shown from another perspective, FIG. 19A-2 depicts IPR system 1900 having a manometer or pressure sensor 1910, a ventilator port 1920, an inlet cap 1930, a body 1940, a patient port 1950, a vacuum stem 1960, and a valve (not shown). FIG. 19B-19F depict system 1900 in various operational configurations, shown in cross-section. As represented in FIG. 19B, vacuum stem 1960 is fully inserted or pushed in. Vacuum stem 1960 can include a vacuum port or lumen 1961. Valve 1970 includes a piston 1971, a valve face 1972, and a rolling diaphragm 1973. A first portion 1962 of vacuum stem 1960 urges valve face 1972 away from rolling diaphragm 1973, thus providing an opening 1975 in valve 1970 through which air, gas, or fluid may flow, as indicated by arrow A. As shown here, inspiratory gases can flow from a ventilator (not shown) through ventilator port 1920, through opening 1975 of valve 1970, through diaphragm aperture or opening 1976 and into or toward the patient (not shown) via patient port 1950. Optionally, a vacuum stem spring 1963 can push vacuum stem 1960 against valve face 1972, thus sealing the vacuum stem 1960 so that no air flows through via vacuum port 1961, while simultaneously opening valve 1970 to vent. In some embodiments, first portion of valve stem 1962 and valve face 1972 form an on/off switch at a vacuum juncture, such that when first portion of valve stem 1962 and valve face 1972 are in contact with each other, the vacuum is closed off due to a vent seal formed between first portion 1962 and valve face 1972. In the operational configuration shown in FIG. 19B, vacuum stem 1960 can be locked or held in place, thus sealing off the vacuum and maintaining an open connection between a ventilator and a patient. A vacuum stem can be sealed off while holding a vent seal open, allowing inspiratory and expiratory gases to pass in both directions.

Figure 19C:
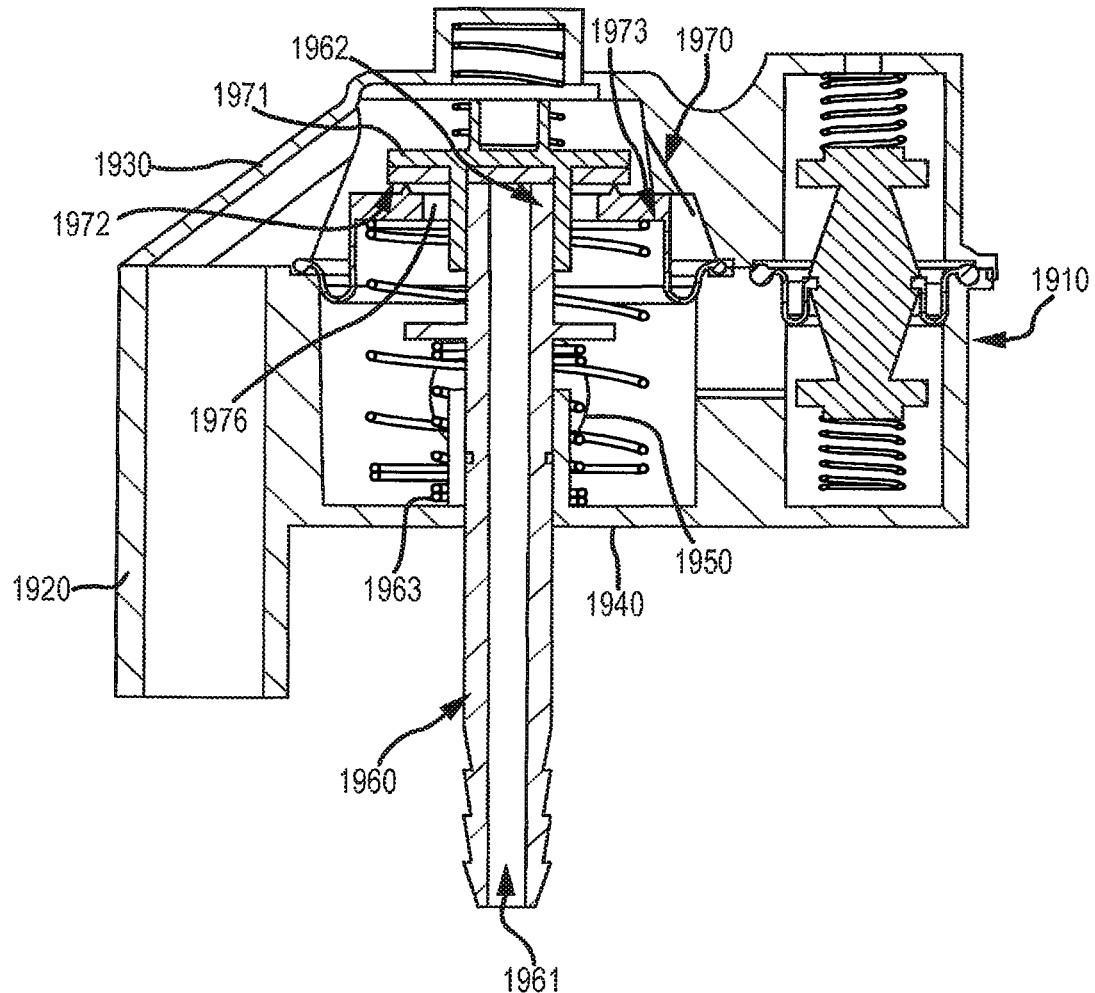
Figure 19D:
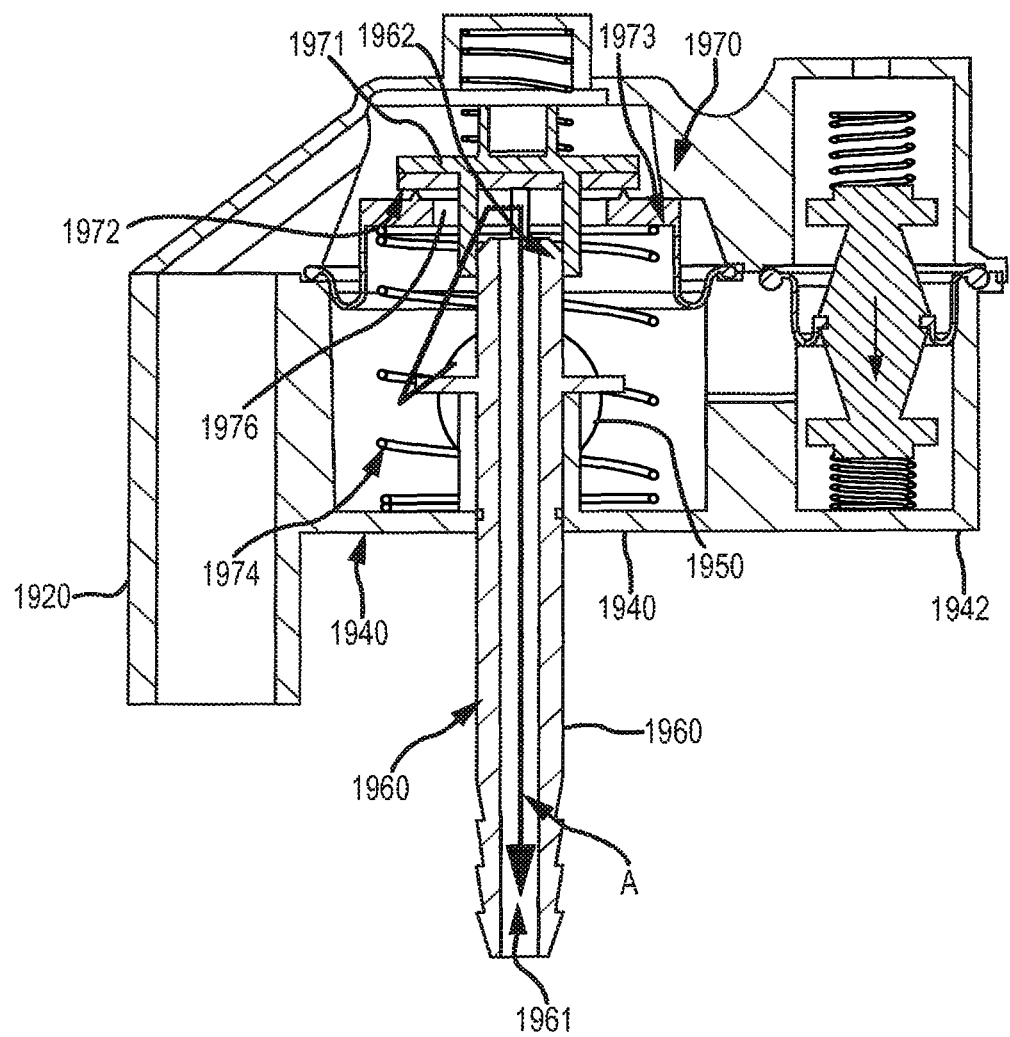

FIG. 19C depicts IPR system 1900 with vacuum stem 1960 in a partially withdrawn configuration. As vacuum stem 1960 is withdrawn, valve face 1972 is allowed to seat against the edge of rolling diaphragm 1973 and vacuum stem 1960 simultaneously, thus sealing both the diaphragm and the stem. When diaphragm 1973 is sealed, air is prevented from flowing through valve 1970. As show here, fluid cannot flow through diaphragm aperture or opening 1976 because valve face 1972 is sealed against diaphragm 1973. When first portion 1962 of stem 1960 is sealed, air or fluid is prevented from flowing through vacuum port 1961 of stem 1960. According to some embodiments, system 1700 presents a 3-way valve having 2 positions. Accordingly, valve 1970 can be open, therefore providing fluid communication between a patient and a ventilator (for example as shown in FIG. 19B) or between patient and vacuum (for example as shown in FIG. 19D). As illustrated in FIG. 19C, the connection or passage between the patient and the ventilator can be broken or interrupted before the connection or passage between the patient and the vacuum is made or established. According to some embodiments, this series of events occurs as the user selectively moves vacuum stem 1960 to the vacuum therapy position. An identical or similar sequence of events can occur as a positive pressure breath is administered through the ventilator port 1920 while vacuum therapy is being administered through the vacuum stem 1960. In the latter case, the positive pressure, rather than the vacuum stem, forces the valve face 1972 against the end or first portion 1962 of the vacuum stem 1960, closing off the vacuum prior to opening the pathway between patient and ventilator. Hence, this dual-sealing of the valve and stem can occur, for example, for an instant while vacuum stem 1960 is being moved to a position which allows vacuum therapy to be administered, for example by a CirQlator or similar device, as depicted in FIG. 19D.

As shown in FIG. 19D, a diaphragm can be in a fully closed position, sealing off a ventilator port, with a vacuum step open to the patient port. A vacuum can pull a manometer piston downward indicating to a physician or operator that vacuum is applied to the patient. An opening between the manometer and main body of the device allows pressure to actuate the manometer. A physician or operator can pull the vacuum stem, locking it in a therapeutic position, enabling the valve mechanism to administer therapy.

FIG. 19D shows vacuum stem 1960 fully or substantially withdrawn, and optionally locked in place. For example, a physician or operator can pull the vacuum stem, locking it into a vacuum therapy position, which enables system 1900 to facilitate vacuum therapy. Here, first portion 1962 of vacuum stem is no longer sealed against valve face 1972, thus allowing vacuum therapy to be administered as shown by arrow A. As depicted here, gas is withdrawn from the patient, through patient port 1950, between first portion 1962 and valve seat 1972, through valve stem lumen 1961, and toward a vacuum source or mechanism (not shown). Rolling diaphragm 1973 is in the closed position, sealing off the ventilator port 1920. Hence, no fluid flows through diaphragm aperture or opening 1976. Vacuum stem 1960 is open to the patient port 1950. When administered, a vacuum can pull a manometer piston 1911 of manometer 1910 downward, or into or toward manometer body 1942. When piston 1911 is in this position, it can provide an indicator to the physician or operator that vacuum is being applied to the patient. For example, the manometer can provide a mechanical signal to the physician. An opening 1912 between manometer 1910 and the main body 1940 allows pressure or vacuum to actuate manometer 1910.

Figure 19E:
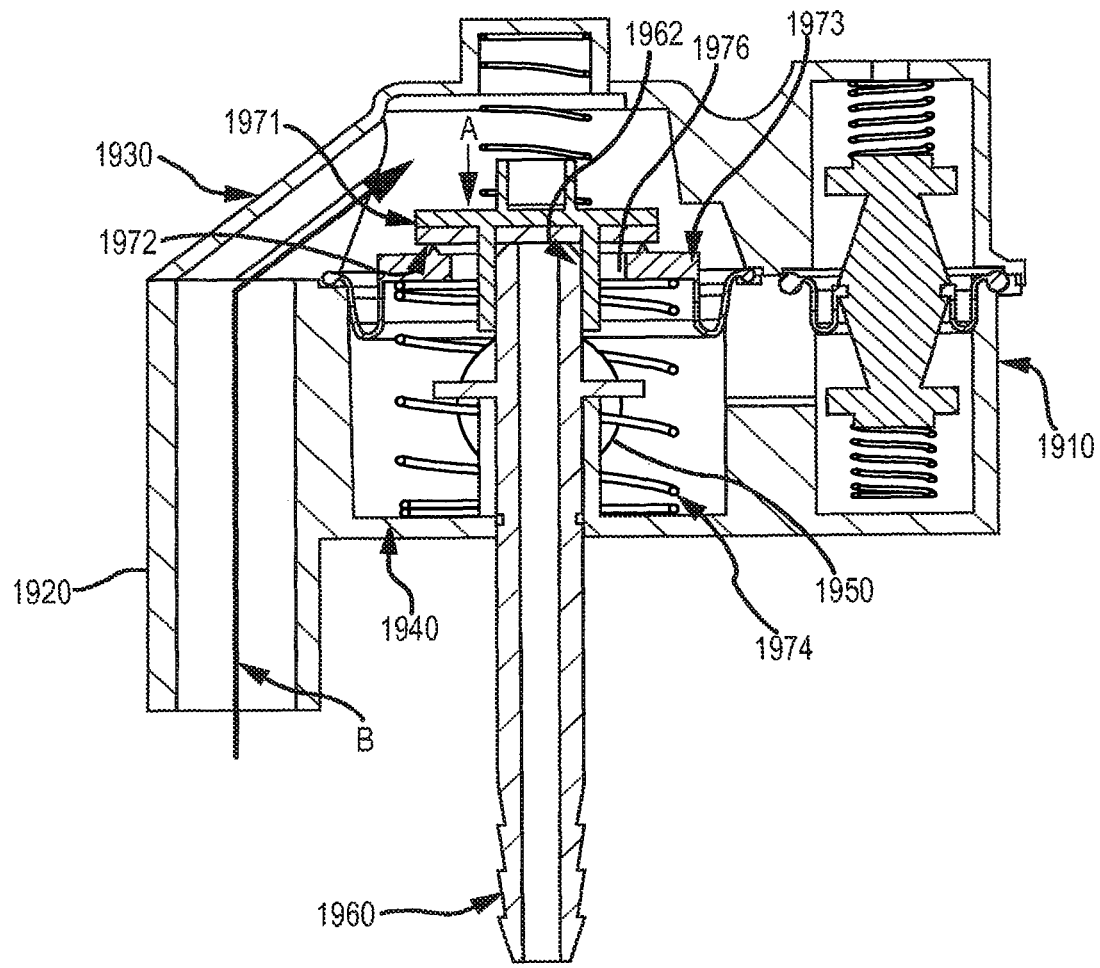

The rolling diaphragm 1973 depicted in FIGS. 19B-19E is shown in the extended position, extending from or away from the body 1940 of IPR system 1900. Rolling diaphragm 1973 is held in or urged toward this extended position by spring 1974 until positive pressure from ventilator provided via ventilation port 1920 overcomes spring 1974 as shown in FIG. 19E, causing diaphragm 1973 to move in the direction indicated by arrow A, downward into or toward body 1940. In some cases, this action can be aided by the upper spring. Hence, due to the initiation of the positive pressure breath, fluid from ventilator enters ventilator port 1920 as indicated by arrow B, and positive pressure pushes diaphragm 1973 and face valve 1972 toward body 1940. A half-stroke configuration is show in FIG. 19E, such that passages to both the vacuum and the ventilator are closed for an instant. As shown here, diaphragm aperture or opening 1976 is closed. The manometer can indicate the pressure condition to which the patient is exposed, regardless of the position of the diaphragm.

As shown in FIG. 19E, upon initiation of a positive pressure breath, positive pressure can push the diaphragm and vent seal down until the seal contacts the vacuum stem. The device is shown at half-stroke, and both the vacuum and the ventilator are closed for an instant.

Figure 19F:
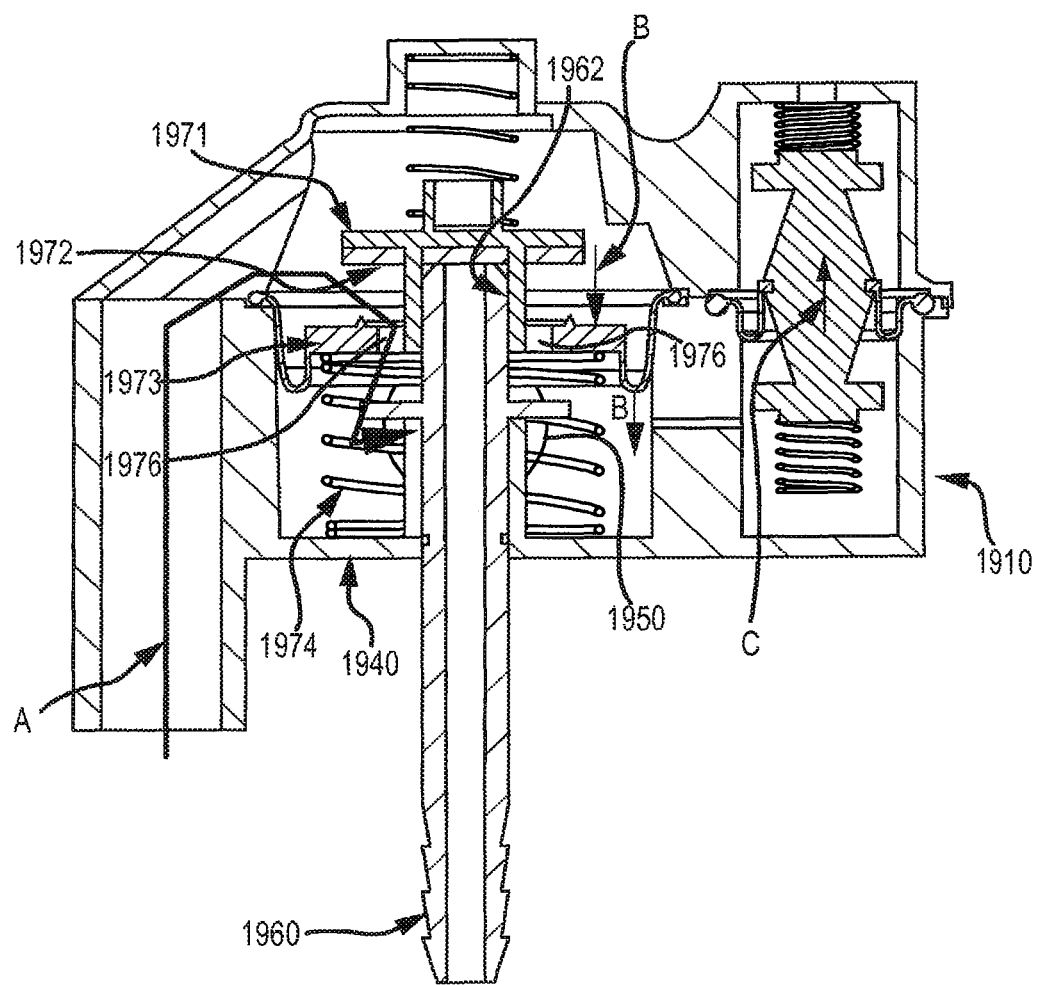

FIG. 19F illustrates the effect of a positive pressure breath. Specifically, a positive pressure breath forces piston 1971, valve face 1972, and diaphragm 1973 toward or into body 1940, until valve face 1972 seals first portion 1962 of vacuum stem 1960. The vacuum is sealed off due to seal between 1972 and 1962. FIG. 19F illustrates the effect of continued translation of the diaphragm 1973 toward or into body 1940, as indicated by arrow B, thus moving relative to vacuum stem 1960. However, as valve face 1972 contacts vacuum stem 1960, piston 1971 and valve face 1972 no longer translate along the length of vacuum stem 1960. Hence, positive pressure breath continues to force the diaphragm downward or toward body 1940, thus opening a gas flow path to allow a breath to be delivered to the patient, while the valve face 1972 remains seated on the first portion 1962 of the valve stem, sealing the vacuum from the patient. Positive pressure breath or gas passes through ventilation port 1920, between valve face 1972 and diaphragm 1973, through diaphragm aperture or opening 1976, and out patient port 1950 toward the patient as indicated by arrow A. Hence, a pathway is open that allows for the positive pressure breath to pass through, across, or past the diaphragm 1973 to the patient while the vacuum is sealed off as a result of the seal between valve face 1972 and first portion 1962 of valve stem 1960. As depicted here, positive pressure from the breath forces the manometer 1910 upward or away from manometer body 1942 as indicated by arrow C, which can provide an indication to a physician or operator that positive pressure is being applied to the patient. Upon release, cessation, or sufficient reduction of positive pressure, the diaphragm return spring 1974 forces the diaphragm 1973 back into its resting position, where it extends or is urged away from body 1940 as depicted in FIGS. 19B-19E, thereby sealing off the pathway from the ventilator prior to opening the pathway to the vacuum.

As shown in FIG. 19F, a ventilator seal can remain seated on a vacuum stem, sealing the vacuum from the patient. Positive pressure breath can continue to force the diaphragm downward, opening the gas flow path to allow a breath to be delivered to the patient. Positive pressure from the breath can force manometer upward indicating a positive pressure application to the patient.

Figure 19G:
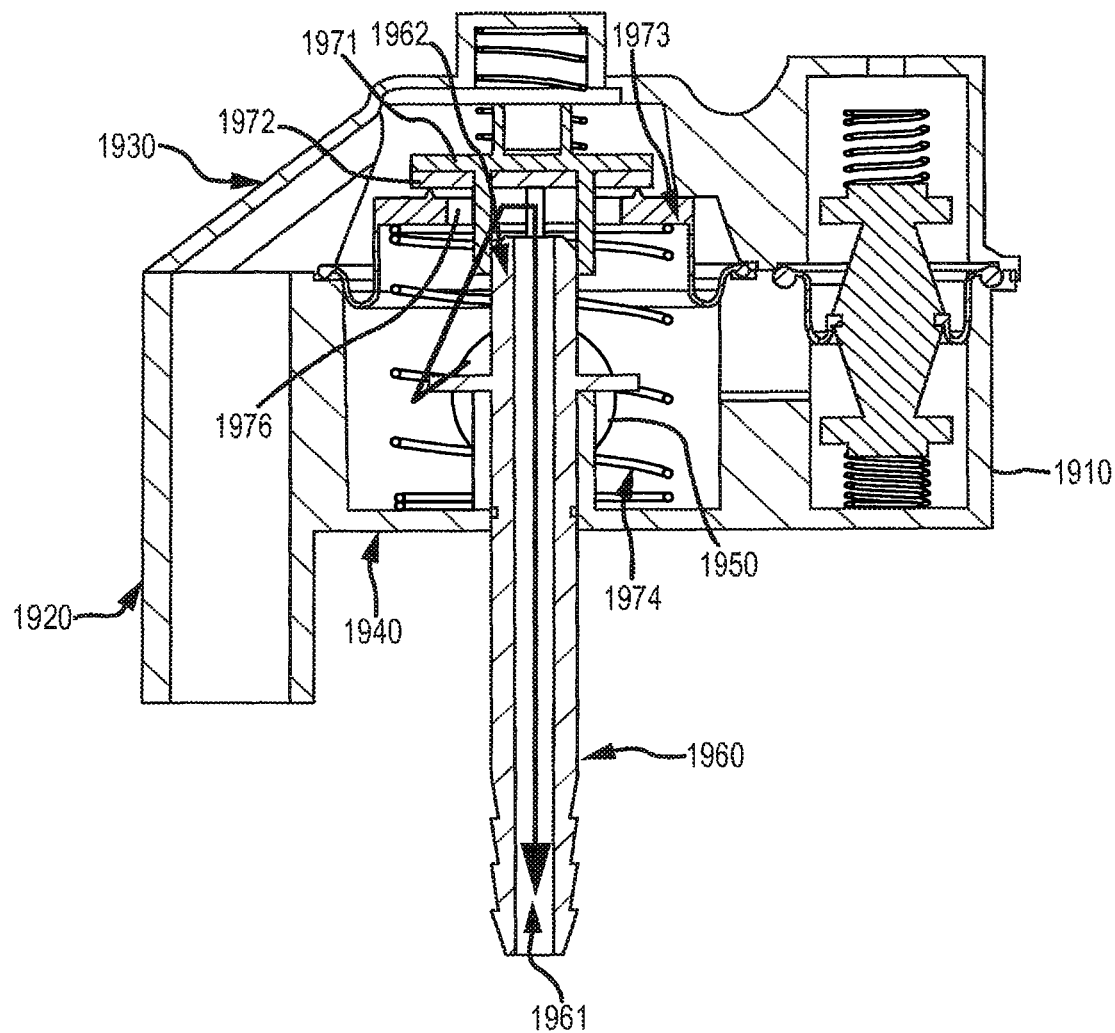

As the positive pressure is released at the end of the delivered breath, the valve moves in reverse motion as shown in FIG. 19G. Cessation of positive pressure can allow the valve to revert to the position shown in FIG. 19D. The connection between patient and ventilator becomes sealed and the vacuum becomes opened in the same manner as that shown in FIG. 19E, however in reverse order. According to some embodiments, the target opening pressure to administer a breath is 8 cm $H_2O$. Vacuum may be limited to 12 cm $H_2O$ and can be insufficient to open the valve. The pressure required to overcome the secondary valve, as if a patient were to spontaneously exhale, can be minimized. IPR device embodiments such as those depicted in FIGS. 19A-19G can be supplemented by or combined with PEEP mechanisms, thus providing treatment systems such as those shown in FIG. 17. In some cases, IPR device embodiments such as those depicted in FIGS. 19A-19G can be used without the addition of a PEEP procedure.

Intrathoracic Pressure Regulation and Intra-Aortic Balloon Pump

The combined use of intrathoracic pressure regulation (IPR) and an intra-aortic balloon pump (IABP), or another assisted device, can provide a greater effect on enhancing circulation to the heart and brain and other vital organs than either approach taken alone. In some cases, this combined technique can incorporate aspects of cuff treatments, such as those described in U.S. Pat. Nos. 6,234,985, 6,224,562, 6,312,399, 6,463,327, and 6,587,726, and in U.S. patent application Ser. No. 12/165,366 filed Jun. 30, 2008 and Ser. No. 12/119,374 filed May 12, 2008, the contents of which are incorporated herein by reference. In some embodiments, an IABP device can decrease myocardial oxygen and increase cardiac output. An IABP device may include a counterpulsating expandable balloon positioned in the aorta, actively deflating in systole and actively inflating in diastole. The expandable element or balloon can be controlled by a computer, optionally coupled with an ECG or pressure transducer.

Recycling Anesthesia

Figure 20:
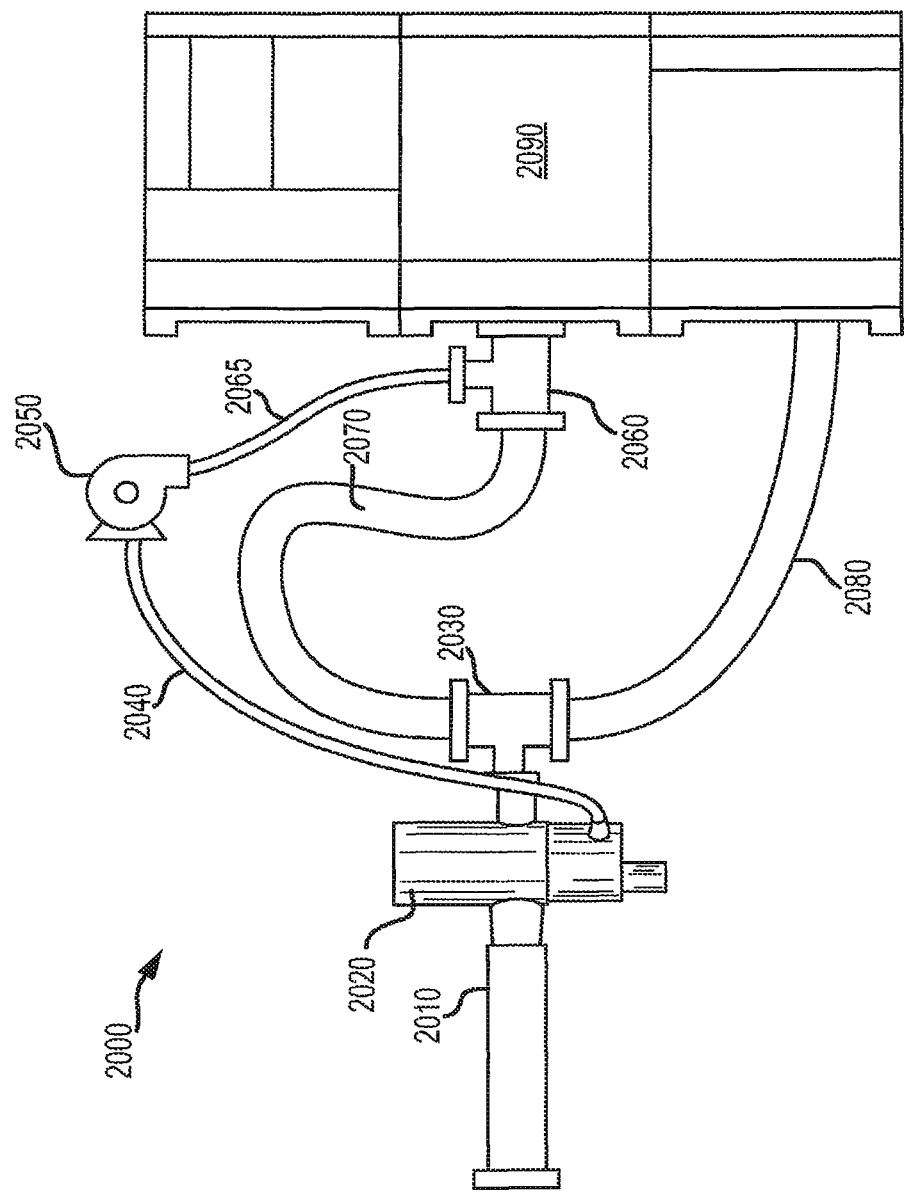
FIG. 20 illustrates a system for administering a pressure regulation treatment to a patient, according to embodiments of the present invention.

Embodiments of the present invention encompass techniques for recycling anesthetic gases when an intrathoracic pressure regulator apparatus (ITPR) is used with an anesthesia machine. For example, as depicted in FIG. 20, it is possible to recycle within an anesthesia machine the anesthesia gases. Hence, IPR can be used without excessive consumption of anesthesia. It is also possible to capture the expiratory gases in a separate chamber/scrubber system. Advantageously, such approaches can help to reduce the overall consumption of anesthesia gases. FIG. 20 illustrates aspects of systems and methods for generating negative airway pressure with an anesthesia machine, according to embodiments of the present invention. Treatment system 2000 includes an endotracheal (ET) tube or mask 2010, which can be coupled with an intrathoracic pressure regulator apparatus (ITPR) 2020. According to some embodiments, ITPR 2020 can incorporate one or more elements of an IPR device such as that depicted in FIGS. 19A-19G. As shown in FIG. 20, a patient wye 2030 is coupled with ITPR apparatus 2020. An ITPR vacuum line 2040 couples ITPR apparatus 2020 with a negative pressure generator 2050. A vacuum return to circuit apparatus 2060 is coupled with negative pressure generator apparatus 2050 via a conduit or passageway 2065. Vacuum return apparatus 2060 is also coupled with an anesthesia machine 2090 and an expiratory limb 2070 of the circuit. In some cases, anesthesia machine 2090 can incorporate or be replaced with a ventilator. Anesthesia machine 2090 is also coupled with an inspiratory limb 2080. Patient wye 2030 is coupled with expiratory limb 2070 and inspiratory limb 2080. As shown here, bulk flow mechanics can be employed to generate negative pressure in the expiratory limb 2070 of the anesthesia machine. Relatedly, the amount of fresh make up gas when using ITPR therapy is reduced. The negative pressure generator 2050 pulls a vacuum on the ITPR vacuum line 2040 to provide ITPR therapy and pushes all or most of the expiratory gas back into the anesthesia machine 2090 through a circuit tee on the expiratory limb 2070 of the circuit. By routing the expiratory gases through a negative pressure generator 2050 and then back into the anesthesia circuit the semi-closed circuit is maintained along with corresponding low flow makeup gas and anesthetic agent. Anesthesia circuits can be considered semi-closed, for various reasons. For example, the gas exhaled by the patient often needs to have the expired carbon dioxide removed from the gas stream. Further, the oxygen and anesthetic agent that is metabolized by the patient is not exhaled and needs to be replaced. The replacing of metabolized oxygen is performed by adding a low flow of gas, or makeup Gas, into the circuit. In some cases a low flow may be preferred so that anesthetic agent is saved.

Ventilator and Anesthesia with ITPR

Figure 21:
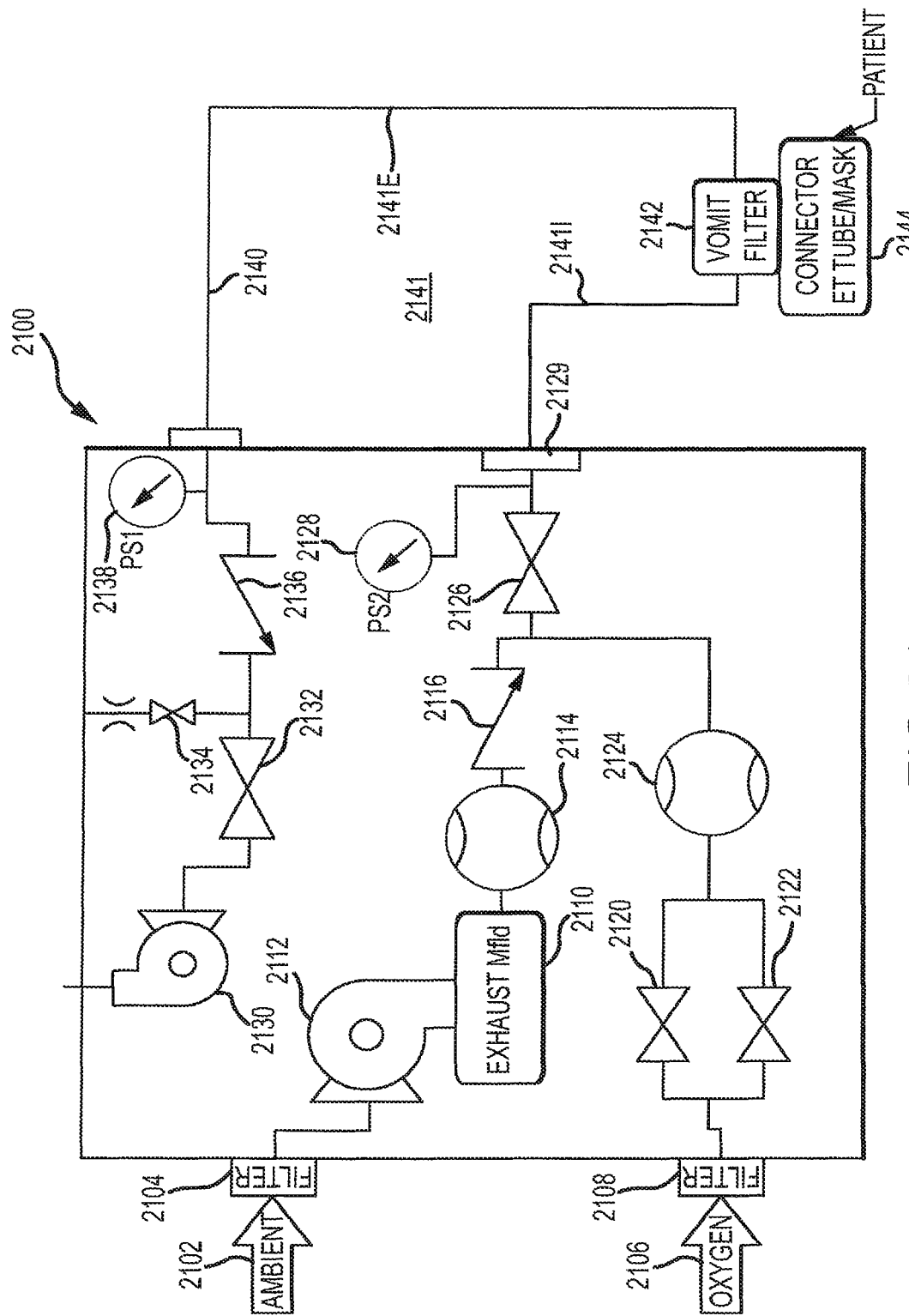
FIG. 21 schematically illustrates a system for administering a pressure regulation treatment to a patient, according to embodiments of the present invention.

FIG. 21 illustrates aspects of an IPR system 2100 according to embodiments of the present invention. In some cases, system 2100 may embody aspects of a push/pull ventilator. When a patient is being ventilated with a mechanical ventilator, the IPR method can be practiced to periodically lower airway pressures to enhance circulation, and when the thorax is intact, to lower intracranial pressure. In some cases the IPR method and device can be incorporated into a mechanism that provides positive pressure ventilation (e.g. a resuscitator bag, a mechanical ventilator, an anesthesia machine, or other means to provide positive pressure ventilation). In some embodiments, IPR therapy can be applied when the patient is being treated with different inspiratory: expiratory (I:E) ratios with the mechanical ventilator. For example, a patient may be treated with a higher I:E ratio (1:2-1:5) and after each inspiration the IPR will reduced airway pressures and/or intrathoracic pressures to between −1 to −20 mmHg for a duration of time varying between 100 milliseconds and 2 seconds prior to the resumption of the positive pressure. By this means respiratory gases can be rapidly extracted from the patient's lungs and circulation can be increased.

As shown in the pneumatic diagram of FIG. 21, IPR system 2100 includes an input for ambient air 2102 having a filter 2104, and an input for oxygen 2106 having a filter 2108. Ambient air input 2102 can be in fluid communication with an exhaust manifold 2110 having a positive inspiratory pressure (PIP) mechanism or blower 2112. Exhaust manifold 2110 is coupled with flow meter 2114, which in turn is coupled with a first inhalation check valve 2116. Oxygen input 2106 can be in fluid communication with a first voltage sensitive orifice (VSO) oxygen valve 2120 and a second VSO oxygen valve 2122. VSO valves 2120, 2122, in turn can be coupled with a flow meter 2124. Check valve 2116 and flow meter 2124 are coupled with a first control valve 2126, which in turn is coupled with a PS2, or second pressure sensor 2128 and a positive pressure delivery mechanism 2129. As shown here, PS2 is in operative association with both control valve 2126 and positive pressure delivery mechanism 2129.

System 2100 also includes an N-Exp pressure mechanism, vacuum source, or blower 2130 coupled with a second control valve 2132, and a continuous positive airway pressure (CPAP) control mechanism 2134 in operative association with second control valve 2132 and an exhalation check valve 2136. Control valve 2132 is coupled with check valve 2136, which in turn is coupled with a PS1, or first pressure sensor 2138. In some cases, operation of blower 2130 can be based on pressure conditions sensed by first pressure sensor 2138. Exhalation check valve 2136 and PS1 2138 are in operative association with vacuum line 2140, which in turn is coupled with vomit filter 2142. Positive pressure delivery mechanism 2129 is also coupled with vomit filter 2142. As shown here, vomit filter 2142 is coupled with a connector mechanism 2144, such as an endotracheal tube or mask. Connector mechanism 2144 in turn can be in operative association with a patient or individual.

In an inhalation configuration, second control valve 2132 is turned off or open, and first control valve 2126 is turned on or closed. PIP blower 2112 is turned on, and may start ahead. For example, the blower may have some inertia, and it is possible to start running the blower prior to starting a breath via the control valve so that when the control valve is opened flow can initiate immediately. N-Exp blower mechanism 2130 is turned off. According to some embodiments, it can be helpful to close off either one or the other control valve, which can facilitate the capability of the device to a) deliver a breath orb) deliver ITPR therapy. The sequence for turning off blowers may vary in some instances. Further, in some cases the inhalation configuration events may occur quite closely together, for example, within a period of less than 20 mSec.

In an exhalation configuration according to some embodiments, second control valve 2132 is turned on or closed, and first control valve 2126 is turned off or opened. PIP blower 2112 is turned off. N-Exp blower mechanism 2130 is turned on, and may start ahead. In some cases the exhalation configuration events may occur quite closely together, for example, within a period of less than 20 mSec. FIG. 21 may include or involve features related to a ventilator or ventilator operation. For example, in some cases all items except N-Exp blower mechanism 2130 may be ventilator related. Aspects of FIG. 21 may be related to the ventilator shown in FIG. 17. From a pneumatic perspective according to some embodiments, ventilator apparatus 1750 on FIG. 17 may be similar to FIG. 21 internally, with the exception of N-Exp blower mechanism 2130. Hence, it may be possible to substitute ventilator apparatus 1750 with the features of FIG. 21, less N-Exp blower mechanism 2130.

Medical Conditions and Replacement Therapy

Embodiments of the present invention are well suited for use in treating patients that are suffering from or at risk of developing conditions such as sepsis, shock, heart failure, acute respiratory distress syndrome, polytrauma, head disease, elevated hepatic or portal vein pressures, bleeding during abdominal, head and neck surgery, or insufficient circulation during open heart surgery. What is more, exemplary techniques can be used to reduce fluid requirement in a patient during a treatment for low blood circulation or low blood pressure. In some cases, systems and methods can be employed to increase microcirculation in a patient or to treat a patient having low microcirculation. Optionally, systems and method can be used to enhance drug circulation in a patient. Exemplary techniques can be used in conjunction with pharmacological therapy. According to some approaches, a CPR protocol is administered to the patient in combination with or in addition to administration of an IPR protocol.

Embodiments of the present invention further encompass methods to evaluate fluid status in a patient that involve applying an IPR protocol to the patient and evaluating the effect on blood pressure. If the blood pressure goes up rapidly, then the patient may benefit from intravenous volume replacement therapy. In some cases, such replacement therapy includes deliver of a crystalloid. In some cases, replacement therapy includes deliver of a colloid.

According to some embodiments, IPR can enhance circulation and thus provide a means to more effectively and safely circulate more blood and drugs administered during low flow states. Because of the increased circulation provided in low blood states with IPR therapy, drugs circulate faster and lower doses can be given in many cases. Thus, the combination of IPR and drug therapy may be particularly helpful clinically. By example, during CPR use of IPR therapy to enhance circulation provides a means to deliver drugs that might normally lower blood pressure to dangerous levels, such as sodium nitroprusside. In patients experiencing states of shock, drugs such as vasopressin or epinephrine can be administered in lower doses to further enhance circulation. Higher doses of vasopressin and epinephrine can have significant untoward effects. In another example, the efficacy of estrogen and progesterone administration during treatment of hypotension is augmented by IPR therapy. Greater circulation, especially to the brain, results in greater efficacy.

Pressure Sensor Location and Blower

Embodiments of the present invention provide unique pressure sensor locations for breath control and unique blower configurations for a vacuum mode that allows control of expiratory resistance by turning a blower on for priming, optionally with the use of feedback control loops.

With continued reference to FIG. 21, intrathoracic pressure regulation (IPR) system 2100 can include pressure sensors at various locations for use in breath control. Optionally, pressure sensors may provide a level of redundancy to the system. IPR system 2100 can be configured to provide pressure monitoring of both inspiratory and expiratory limb pressures, and active control of end exhale pressures to sub-atmospheric levels when in a circulatory assist mode. IPR system 2100 can incorporate the use of pressure sensor redundancy to protect against patient injury which may be caused by a faulty sensor. It is possible to accomplish the goals of safety redundancy and monitoring of an expiratory limb 2141E and an inspiratory limb 12411 of a patient circuit 2141 by careful placement of pressure transducers in the device. As shown in FIG. 21, a first pressure sensor 2138 can operate to monitor pressure in the expiratory line 2141E, and a second pressure sensor 2128 can operate to monitor pressure in the inspiratory line 21411. In some cases, pressure sensor 2138 placed on or in communication with the expiratory limb 2141E can be used to monitor and control the active exhalation function in a circulatory assist mode or procedure. To maintain redundant safety monitoring of the patient airway at all times the pressure sensors are placed in such a way that when the breathing circuit 2141 is connected to the manifold or device, each pressure sensor or transducer is monitoring a particular side of the breathing circuit (e.g. exhalation side 2141E or inhalation side 21411) so that one transducer can be used for a feedback control loop and the other transducer can be used as a redundant safety monitoring feature. This placement of the transducers allows for the use of two transducers for control and safety redundancy rather than, for example, a system that includes four transducers wherein two transducers are on the inspiratory side of the circuit and two transducers are on the expiratory side of the circuit. The two transducer system described herein allows direct communication of the pressure transducer location and the connection point of the breathing circuit. In comparison, if the transducers are placed in such a manner as to not allow direct communication of the pressure transducer location and the connection point of the breathing circuit, four transducers may be required. The pressure sensor location is detailed in the pneumatic schematic shown in FIG. 21. The sensors are labeled PS1 and PS2, with PS1 monitoring the expiratory line 2141E and PS2 monitoring the inspiratory line 2141I.

The expiratory phase of the ventilatory cycle is only a minor focus of mechanical ventilation. The primary focus for mechanical ventilation is the delivery of air to the patient's lungs with a lesser focus on how air is allowed out of the lungs. The expiratory limb of a mechanical ventilator can be designed with a goal of reducing airflow resistance to the extent possible to allow passive expiratory flow to eliminate the inhaled tidal volume. One other feature commonly found in mechanical ventilators that effects expiratory flow is the addition of positive end expiratory pressure (PEEP). Outside of PEEP and design of low resistance pathways, expiratory flow has been largely ignored in mechanical ventilation. Currently some ventilators have a limited capability for generating a negative expiratory pressure to augment the natural release of the delivered tidal volume. Treatment systems according to embodiments of the present invention provide for richer control of expiratory flow by use of a blower to generate a negative pressure to enhance expiratory flow, which may in some cases be related to a priming procedure. The use of a servo controlled expiratory pressure source allows a wide range of control of expiratory flow. With servo controlled expiratory pressure, the device can generate a thoracic vacuum at a variety of levels of end expiratory pressure and varying pressure profiles from end inhalation pressure to end expiratory pressure.

Embodiments of the present invention provide a treatment system having a unique two-limb circuit. As depicted in FIG. 21, Inspiratory and expiratory flow paths travel from the treatment system or manifold to the patient through a dual limb patient circuit 2141. The two limbs 2141I, 2141E can be concentric. For example, tube assembly can include an inner lumen providing the inspiratory path and an outer lumen providing the expiratory path. The connection at the patient end can include a standard 22 mm female conical ISO fitting. The connection at the treatment device can affix directly to a manifold system housed within the device. The connection at the treatment device can include a pair of conical fittings, concentrically oriented. This connection configuration can allow a caregiver to make both Inspiratory and expiratory circuit limb connections simultaneously, with a single motion. Additionally, this arrangement can prevent the caregiver from inadvertently mixing up the inspiratory and expiratory limbs. As further described elsewhere herein, inspiratory and expiratory flow paths can be controlled via two solenoid valves (one for each direction of flow) mounted on a 2-plane manifold system. Through the valve, the flow path can enter by an outer ring of openings and exit the valve by a centrally located lumen. Inspiratory and expiratory pressures can be monitored through pneumatic ports located on each plane of the manifold. As further described elsewhere herein, the inspiratory plane can collect and combine fresh air from a positive pressure blower and oxygen from a separate valved manifold which controls the flow rate of oxygen. Check valves can be located at both fresh air and oxygen inlet locations to prevent flow in the reverse direction. When the valve opens, the flow path allows the combined oxygen and air to pass through to the center lumen connected to the patient circuit. Because the patient circuit is often in a concentric orientation and that the inspiratory and expiratory gasses typically do not mix, the inspiratory path travels through the expiratory plane of the manifold before connecting to the patent circuit. This is accomplished by a sliding seal where one component telescopes into the other, compressing an O-ring radially between them. Expiratory gasses enter the manifold through the outer lumen of the patient circuit. A check valve is located at the entrance of the expiratory path to prevent expiratory gasses from being re-breathed by the patient. In a fashion similar to that of the inspiratory flow, a valve opens and closes to control the flow of expiratory gases. Gases enter the valve through an outer ring of openings and exit through a central lumen. When the valve is open, this allows the flow to pass from the expiratory plane of the manifold to a negative pressure blower which exhausts to the atmosphere. The connection between the expiratory plane of the manifold and negative pressure blower utilizes a similar O-ring seal mechanism as was described for inspiratory gases.

In some embodiments, a treatment system can include a communication module that communicates with an external medical device. The communication module can include a blue tooth assembly, a radiofrequency assembly, or a communication assembly that communicates at a selected or desired bandwidth. The external medical device may be a defibrillator or automated chest compressor, or the like. Such communications can be used to time the delivery of changes in positive and negative intrathoracic pressure with either a defibrillation shock and/or chest compression and release.

Manifold Systems and Methods

Figure 22A:
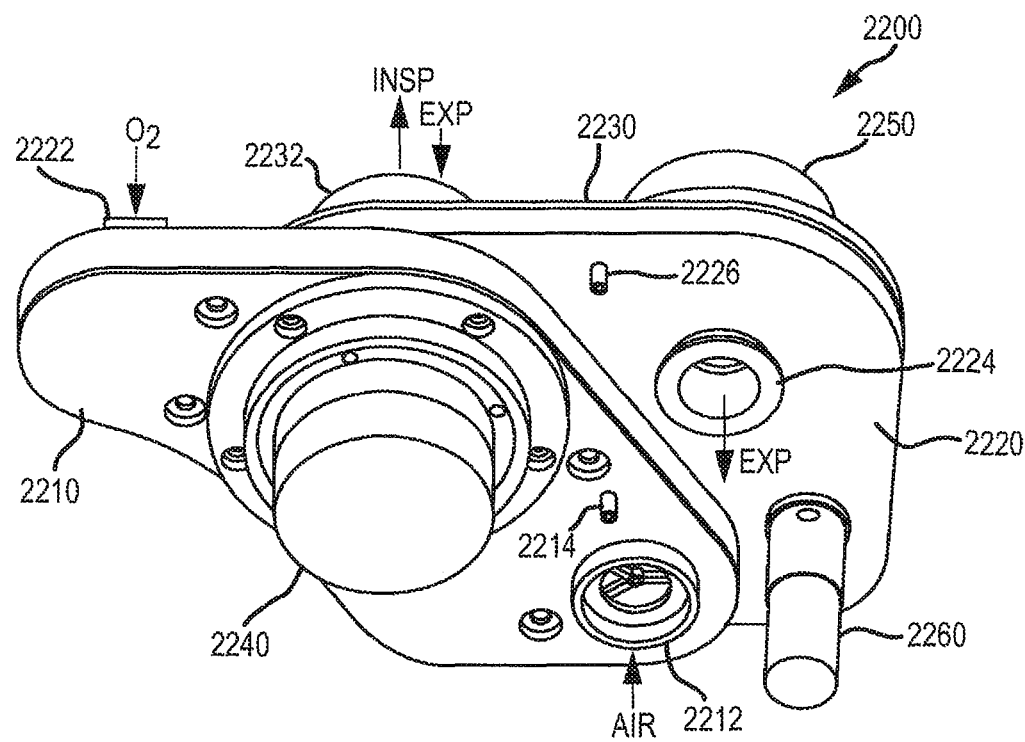

FIGS. 22A to 22G show aspects of manifold systems and methods according to embodiments of the present invention. Exemplary manifold systems can provide a 2-plane manifold that segregates inspiratory and expiratory gases. As depicted in FIG. 22A, manifold system 2200 includes a distal interface 2210, a proximal interface 2230, and a central interface 2220 disposed between the distal interface 2210 and the proximal interface 2230. Manifold system 2200 also includes an inspiratory control valve assembly 2240 coupled with distal interface 2210, and an expiratory control valve assembly 2250 coupled with proximal interface 2230. Actuation of inspiratory control valve assembly 2240 operates to control the flow of inspiratory gases into manifold system 2200. For example, the opening of inspiratory control valve assembly 2240 facilitates the entry of inspiratory gases into manifold system 2200, and the closing of inspiratory control valve assembly 2240 inhibits the entry of inspiratory gases into manifold system 2200. In some cases, inspiratory control valve assembly 2240 includes a solenoid valve. Actuation of expiratory control valve assembly 2250 operates to control the flow of expiratory gases into manifold system 2200. For example, the opening of expiratory control valve assembly 2250 facilitates the entry of expiratory gases into manifold system 2200, and the closing of expiratory control valve assembly 2250 inhibits the entry of expiratory gases into manifold system 2200. In some cases, expiratory control valve assembly 2250 includes a solenoid valve. Expiratory control valve assembly 2250 can operate in many ways, for example to facilitate delivery of a negative pressure treatment in conjunction with a vacuum mechanism or negative pressure blower, or to facilitate the delivery of a PEEP treatment. In some instances, if the expiratory control valve assembly 2250 is in an open configuration, the vacuum mechanism can pull a negative pressure so as to reduce the airway pressure. Alternatively, the expiratory control valve assembly 2250 can be closed with an amount of positive pressure remaining in the airway, thus providing a PEEP protocol. Hence, the same control valve assembly 2250 can operate to provide two different functions.

Inspiratory gases for delivery to the patient can enter manifold system 2200 in a variety of ways. As shown in FIG. 22A, central interface 2220 may include an oxygen inlet 2222 that receives oxygen from an oxygen source, and distal interface 2210 may include an air inlet port 2212 that receives air from an air source, such as a positive pressure blower. Hence, air inlet port 2212 can be in fluid communication with an air source for example via a fluid passage means such as a tube, and oxygen inlet 2222 can be in fluid communication with an oxygen source for example via a fluid passage means such as a tube. Inspiratory gases for delivery to the patient can be emitted from manifold system 2200 toward the patient, for example via a patient circuit interface 2232 of proximal interface 2230. Expiratory gases from the patient can enter manifold system 2200 at, for example, patient circuit interface 2232 of proximal interface 2230. Expiratory gases can pass through manifold system 2200 out of an expiratory gas outlet port 2224 of central interface 2220, for example, and toward a negative pressure blower. Expiratory gas outlet port 2224 can be in fluid communication with a negative pressure blower for example via a fluid passage means such as a tube.

Manifold system 2200 may also include one or more sampling ports for evaluating pressure at various locations throughout the manifold system. As shown in FIG. 22A, central interface 2220 includes an expiratory sampling port 2226 for use in sampling expiratory pressures. Similarly, distal interface 2210 includes an inspiratory sampling port 2214 for use in sampling inspiratory pressures.

In some cases, a manifold system 2200 may also include a continuous positive airway pressure (CPAP) assembly 2260. As shown in FIG. 22A, central interface 2220 includes a CPAP port 2228 coupled with the CPAP assembly 2260. Operation of CPAP assembly 2260 can facilitate the administration of adjustable levels of continuous positive airway pressure to a patient.

Figure 22B:
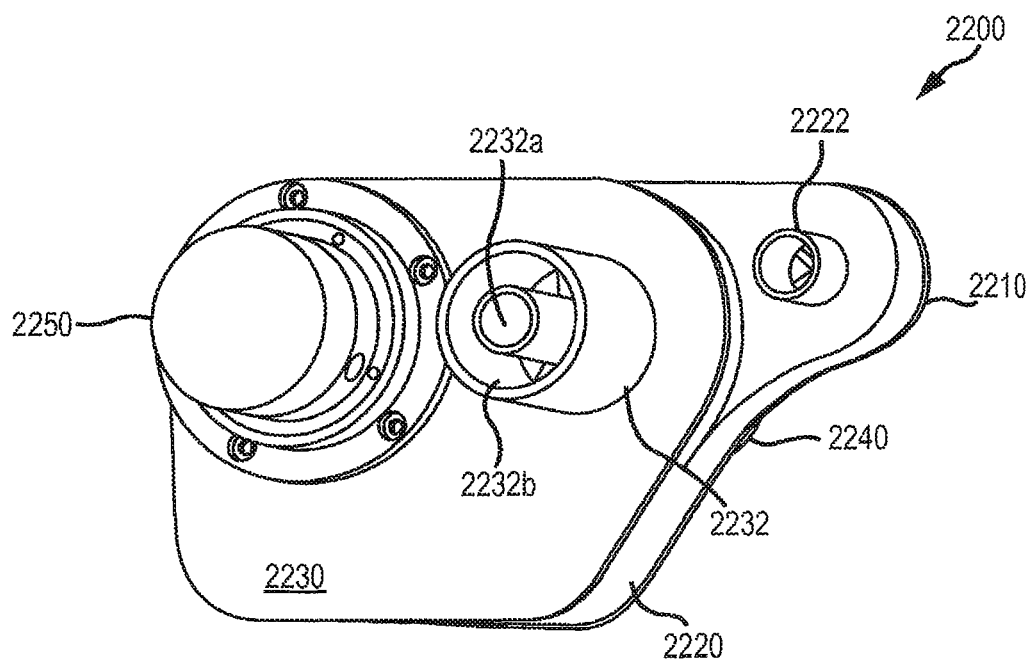

FIG. 22B shows another view of manifold system 2200. As depicted here, manifold system 2200 includes a distal interface 2210, a proximal interface 2230, and a central interface 2220 disposed between the distal interface 2210 and the proximal interface 2230. Manifold system 2200 also includes an inspiratory control valve assembly 2240 coupled with distal interface 2210, and an expiratory control valve assembly 2250 coupled with proximal interface 2230. Central interface 2220 may include an oxygen inlet 2222 that receives oxygen from an oxygen source. Inspiratory gases for delivery to the patient can be emitted from manifold system 2200 toward the patient, for example via a patient circuit interface 2232 of proximal interface 2230. Expiratory gases from the patient can enter manifold system 2200 at, for example, patient circuit interface 2232 of proximal interface 2230. As shown in FIG. 22B, patient circuit interface 2232 presents a concentric configuration having an inner or inspiratory lumen 2232 *a* and an outer or expiratory lumen 2232 *b*. Inner lumen 2232 *a* operates to carry inspiratory gases out of the manifold and toward the patient, and outer lumen 2232 *b* operates to carry expiratory gases away from the patient and into the manifold. Typically, these inspiratory and expiratory gases are transmitted between the patient and patient circuit interface 2232 via a tube assembly having a first passage for inspiratory gases and a second passage for expiratory gases. For example, inspiratory and expiratory gases can be transmitted between the patient and patient circuit interface 2232 via a concentric tube assembly. The concentric tube assembly can include inner passage that fluidly communicates with inner lumen 2232 *a* and an outer passage that fluidly communications with outer lumen 2232 *b*.

Figure 22C:
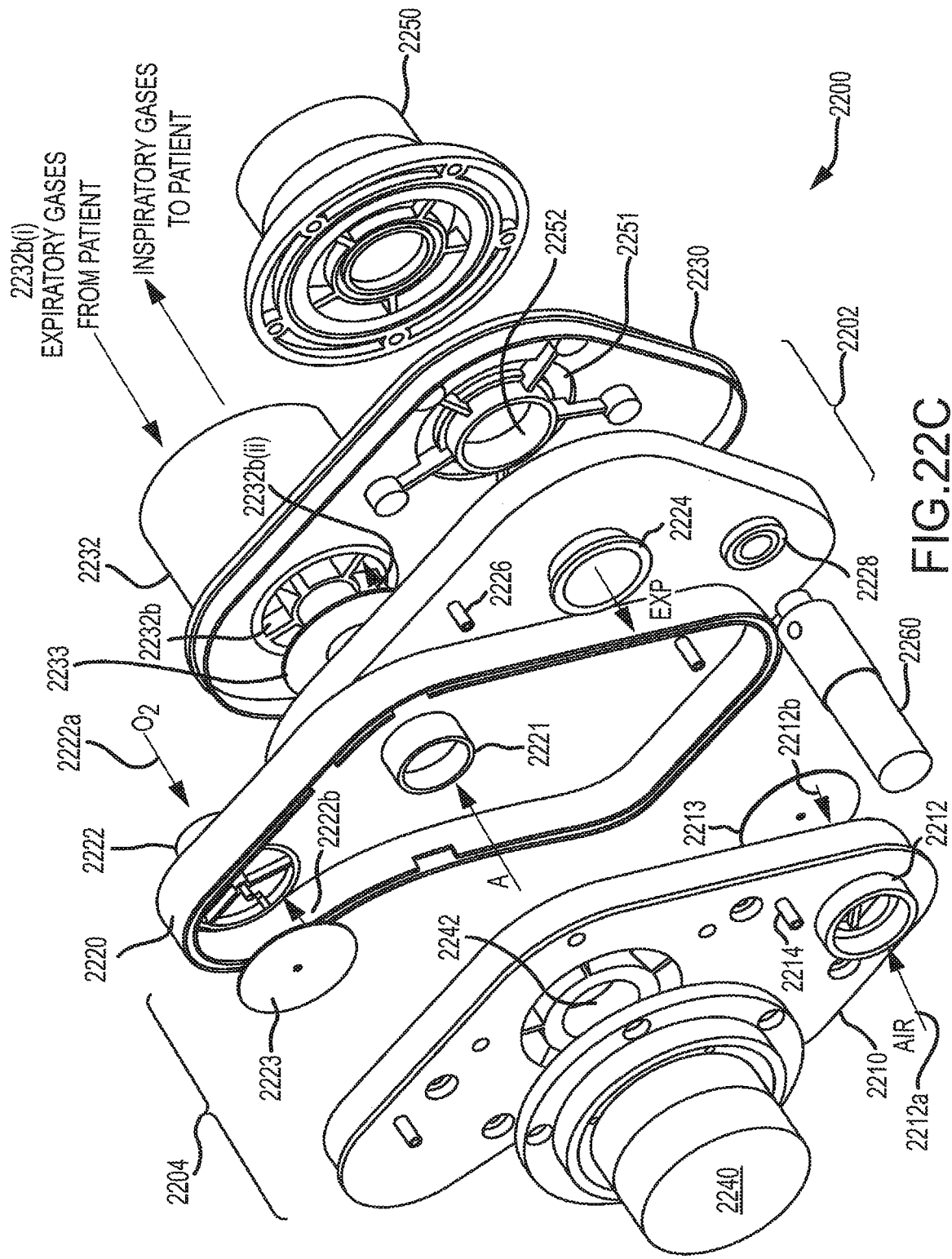

FIG. 22C shows an exploded perspective view of manifold system 2200 according to embodiments of the present invention. Manifold system 2200 includes a distal interface 2210, a proximal interface 2230, and a central interface 2220 disposed between the distal interface 2210 and the proximal interface 2230. Manifold system 2200 also includes an inspiratory control valve assembly 2240 coupled with distal interface 2210, and an expiratory control valve assembly 2250 coupled with proximal interface 2230. Actuation of inspiratory control valve assembly 2240 operates to control the flow of inspiratory gases into manifold system 2200. For example, the opening of inspiratory control valve assembly 2240 facilitates the entry of inspiratory gases into manifold system 2200, and the closing of inspiratory control valve assembly 2240 inhibits the entry of inspiratory gases into manifold system 2200. In some cases, inspiratory control valve assembly 2240 includes a solenoid valve. Actuation of expiratory control valve assembly 2250 operates to control the flow of expiratory gases into manifold system 2200. For example, the opening of expiratory control valve assembly 2250 facilitates the entry of expiratory gases into manifold system 2200, and the closing of expiratory control valve assembly 2250 inhibits the entry of expiratory gases into manifold system 2200. In some cases, expiratory control valve assembly 2250 includes a solenoid valve.

Inspiratory gases for delivery to the patient can enter manifold system 2200 in a variety of ways. As shown in FIG. 22C, central interface 2220 may include an oxygen inlet 2222 that receives oxygen from an oxygen source, and distal interface 2210 may include an air inlet 2212 that receives air from an air source, such as a positive pressure blower. Inspiratory gases for delivery to the patient can be emitted from manifold system 2200 toward the patient, for example via a patient circuit interface 2232 of proximal interface 2230. Expiratory gases from the patient can enter manifold system 2200 at, for example, patient circuit interface 2232 of proximal interface 2230. Expiratory gases can pass through manifold system 2200 out of an expiratory gas outlet port 2224 of central interface 2220, for example, and toward a negative pressure blower. Expiratory gas outlet port 2224 can be coupled with a negative pressure blower via a fluid passage means such as a tube.

Manifold system 2200 may also include one or more sampling ports for evaluating pressure at various locations throughout the manifold system. As shown in FIG. 22C, central interface 2220 includes an expiratory sampling port 2226 for use in sampling expiratory pressures. For example, expiratory sampling port 2226 can be used to sample expiratory pressures present within an expiratory plane or chamber 2202 defined between proximal interface 2230 and central interface 2220. Similarly, distal interface 2210 includes an inspiratory sampling port 2212 for use in sampling inspiratory pressures. For example, inspiratory sampling port 2212 can be used to sample inspiratory pressures present within an inspiratory plane or chamber 2204 defined between distal interface 2210 and central interface 2220.

According to some embodiments, pressures or flow rates sensed at inspiratory sampling port 2214 or expiratory sampling port 2226 can be used to determine fluid flow rates throughout the manifold.

Manifold system 2200 may also include one or more check valves for modulating or controlling fluid flow at various locations throughout the manifold system. As shown in FIG. 22C, manifold system 2200 includes an oxygen check valve 2223 that operates to prevent or inhibit reverse flow through oxygen inlet 2222, such that oxygen can flow into manifold system 2200 via inlet 2222 in the direction indicated by arrow 2222A, but fluid is prevented or inhibited from flowing out of manifold system 2200 via inlet 2222 in the reverse direction indicated by arrow 2222B. Similarly, manifold system 2200 includes an air check valve 2213 that operates to prevent or inhibit reverse flow through air inlet 2212, such that air can flow into manifold system 2200 via inlet 2212 in the direction indicated by arrow 2212A, but fluid is prevented or inhibited from flowing out of manifold system 2200 via inlet 2212 in the reverse direction indicated by arrow 2212B. Further, manifold system 2200 includes a patient circuit or expiratory check valve 2233 that operates to prevent or inhibit reverse flow through patient circuit interface 2232, such that fluid can flow into manifold system 2200 via outer or expiratory lumen 2232 b in the direction indicated by arrow 2232 b(i), but fluid is prevented or inhibited from flowing out of manifold system 2200 via outer or expiratory lumen 2232 b in the reverse direction indicated by arrow 2232 b(ii).

In some cases, a manifold system 2200 may also include a continuous positive airway pressure (CPAP) assembly 2260. As shown in FIG. 22C, central interface 2220 includes a CPAP port 2228 coupled with the CPAP valve assembly 2260. The inspiratory plane or chamber 2204 can operate to collects and combine fresh air from a positive pressure blower and oxygen from a separate valved manifold which controls the flow rate of oxygen. Check valves 2213 and 2223 are located at both fresh air and oxygen inlet locations, respectively, to prevent or inhibit flow in the reverse direction. When control valve 2242 opens, the flow path allows the combined oxygen and air to pass through to the center lumen 2221 connected to the patient circuit as indicated by arrow A. According to some embodiments, the patient circuit is in a concentric orientation, the inspiratory and expiratory gasses are not allowed to mix, and the inspiratory path travels through the expiratory plane of the manifold before connecting to the patent circuit. Such objectives can be achieved by use of a sliding seal where one component telescopes into the other, compressing an O-ring radially between them. As depicted in FIG. 22C, an O-ring can be located between center lumen 2221 of central interface 2220 and centrally located lumen 2242 of distal interface 2210. As further explained elsewhere herein, expiratory gasses enter the manifold through the outer lumen 2232 b of the patient circuit. A check valve 2233 is located at the entrance of the expiratory path to prevent expiratory gasses from being re-breathed by the patient. In a fashion similar to that of the inspiratory flow, a valve 2250 opens and closes to control the flow of expiratory gasses. Gases enter the valve 2250 through an outer ring of openings 2251 and exit through a central lumen 2252. When the valve 2250 is open, this allows the flow to pass from the expiratory plane 2202 of the manifold to a negative pressure blower which exhausts to the atmosphere. The connection between the expiratory plane 2202 of the manifold and a negative pressure blower can use an O-ring seal mechanism similar to the one described for inspiratory gases. For example, an O-ring cal be located between orifice 2252 and the orifice inner diameter of flange 2224.

FIG. 22D shows an exploded perspective view of a portion of manifold system 2200 according to embodiments of the present invention, in addition to aspects of an inspiratory flow path 2201 provided by the manifold system. Manifold system 2200 includes a distal interface 2210, a proximal interface (not shown), and a central interface 2220 disposed between the distal interface 2210 and the proximal interface. Manifold system 2200 also includes an inspiratory control valve assembly 2240 coupled with distal interface 2210. Actuation of inspiratory control valve assembly 2240 operates to control the flow of inspiratory gases into manifold system 2200 from various fluid sources. For example, the opening of inspiratory control valve assembly 2240 facilitates the exit of inspiratory gases from the inspiratory plane or chamber 2204 as indicated by arrows 2212 ii and 2222 ii, the return of inspiratory gases toward distal interface 2210 as indicated by arrows 2212 iii and 2222 iii, and the entry of expiratory gases into an inspiratory delivery port 2221 of central interface 2220 as indicated by arrows 2212 iv and 2222 iv. Conversely, the closing of inspiratory control valve assembly 2240 inhibits the entry of inspiratory gases into manifold system 2200 from, for example, oxygen and air sources. In some cases, inspiratory control valve assembly 2240 includes a solenoid valve.

Inspiratory gases for delivery to the patient can enter manifold system 2200 in a variety of ways. As shown in FIG. 22D, central interface 2220 may include an oxygen inlet 2222 that receives oxygen from an oxygen source, and distal interface 2210 may include an air inlet 2212 that receives air from an air source, such as a positive pressure blower. Manifold system 2200 may also include one or more check valves for modulating or controlling fluid flow at various locations throughout the manifold system. For example, manifold system 2200 includes an oxygen check valve 2223 that operates to prevent or inhibit reverse flow through oxygen inlet 2222, such that oxygen can flow into manifold system 2200 via inlet 2222 in the direction indicated by arrows 2222 i and 2222 ii, but fluid is prevented or inhibited from flowing out of manifold system 2200 via inlet 2222 in the reverse direction. Relatedly, control valve 2240 operates to control flow out from inspiratory plane or chamber 2204, as indicated by arrows 2222 ii and 2212 ii, through valve 2240 as indicated by arrows 2222 iii and 2212 iii, and through an inspiratory delivery port 2221 of central interface 2220 toward the patient as indicated by arrows 2222 iv and 2212 iv, via an inspiratory or internal lumen of a patient circuit interface of a proximal interface. In this way, selective opening and closing of inspiratory control valve 2240 modulates the flow of air and oxygen to the patient. As illustrated in FIG. 22D, through the valve 2240, the flow path can enter by an outer ring of openings 2241 and exit the valve by a centrally located lumen 2242. Manifold system 2200 also includes an air check valve 2213 that operates to prevent or inhibit reverse flow through air inlet 2212, such that air can flow into manifold system 2200 via inlet 2212 in the direction indicated by arrows 2212 i and 2212 ii, but fluid is prevented or inhibited from flowing out of manifold system 2200 via inlet 2212 in the reverse direction. During operation, air and oxygen can mix within the inspiratory chamber 2204, optionally at desired air:oxygen ratios, pass through inspiratory control valve 2240 and inspiratory delivery port 2221, and to the patient via the inner or inspiratory lumen of the patient circuit interface. In some cases, introduction of air and oxygen into the manifold can be independently controlled. Systems may include sensors which measure the flow rate or pressure, or both, of air or oxygen prior to mixing. Control of inspiratory gas administration to the patient can be based upon any combination of such flow rates or pressures.

Figure 22E:
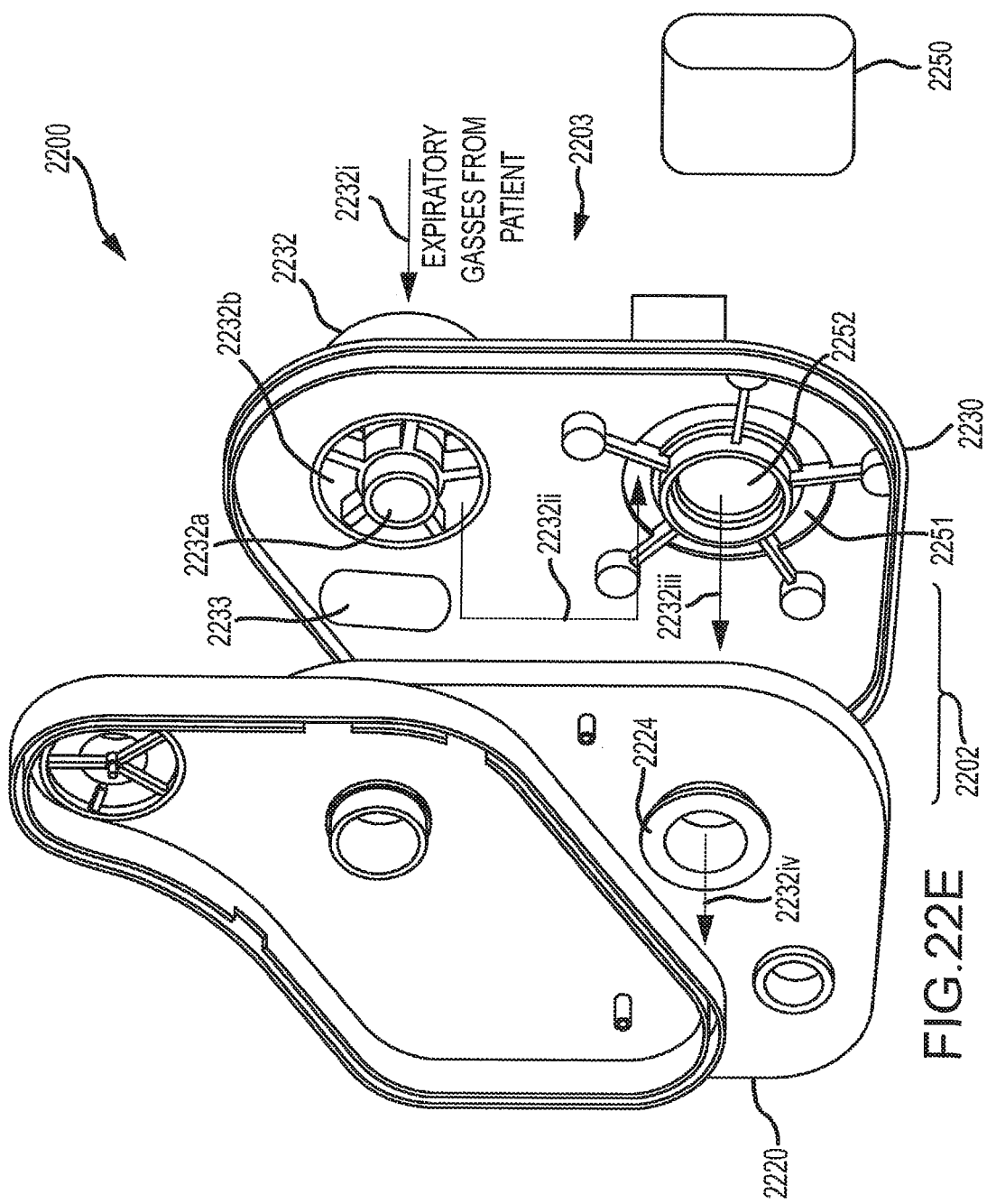

FIG. 22E shows an exploded perspective view of a portion of manifold system 2200 according to embodiments of the present invention, in addition to aspects of an expiratory flow path 2203 provided by the manifold system. Manifold system 2200 includes a distal interface (not shown), a proximal interface 2230, and a central interface 2220 disposed between the distal interface and the proximal interface 2230. Manifold system 2200 also includes an expiratory control valve assembly 2250 coupled with proximal interface 2230. Actuation of expiratory control valve assembly 2250 operates to control the flow of expiratory gases into manifold system 2200 from the patient. For example, the opening of expiratory control valve assembly 2250 facilitates the entry of expiratory gases into manifold system 2200 as indicated by arrows 2232 i and 2232 ii, and the closing of expiratory control valve assembly 2250 inhibits the entry of expiratory gases into manifold system 2200. In some cases, expiratory control valve assembly 2250 includes a solenoid valve.

Expiratory gases from the patient can be routed through manifold system 2200 by first passing through an expiratory or external lumen 2232 b of patient circuit interface 2232 of proximal interface 2230, as indicated by arrow 2232 i. Manifold system 2200 may also include a check valve for modulating or controlling fluid flow at proximal interface. For example, manifold system 2200 includes an expiratory check valve 2233 that operates to prevent or inhibit reverse flow through circuit interface 2232, such that expiratory gases can flow from the patient and into manifold system 2200 via expiratory lumen 2232 b of circuit interface 2232 in the direction indicated by arrows 2232 i and 2232 ii, but fluid is prevented or inhibited from flowing out of manifold system 2200 via expiratory lumen 2232 b of circuit interface 2232 in the reverse direction. Relatedly, control valve 2250 operates to control flow out from expiratory plane or chamber 2202, as indicated by arrow 2232 ii, through valve 2250 as indicated by arrow 2232 iii, and through expiratory gas outlet port 2224 of central interface 2220 as indicated by arrow 2232 iv. In this way, selective opening and closing of expiratory control valve 2250 modulates the flow of expiratory gases from the patient. As illustrated in FIG. 22E, through the valve 2250, the flow path can enter by an outer ring of openings 2251 and exit the valve by a centrally located lumen 2252.

Figure 22F:
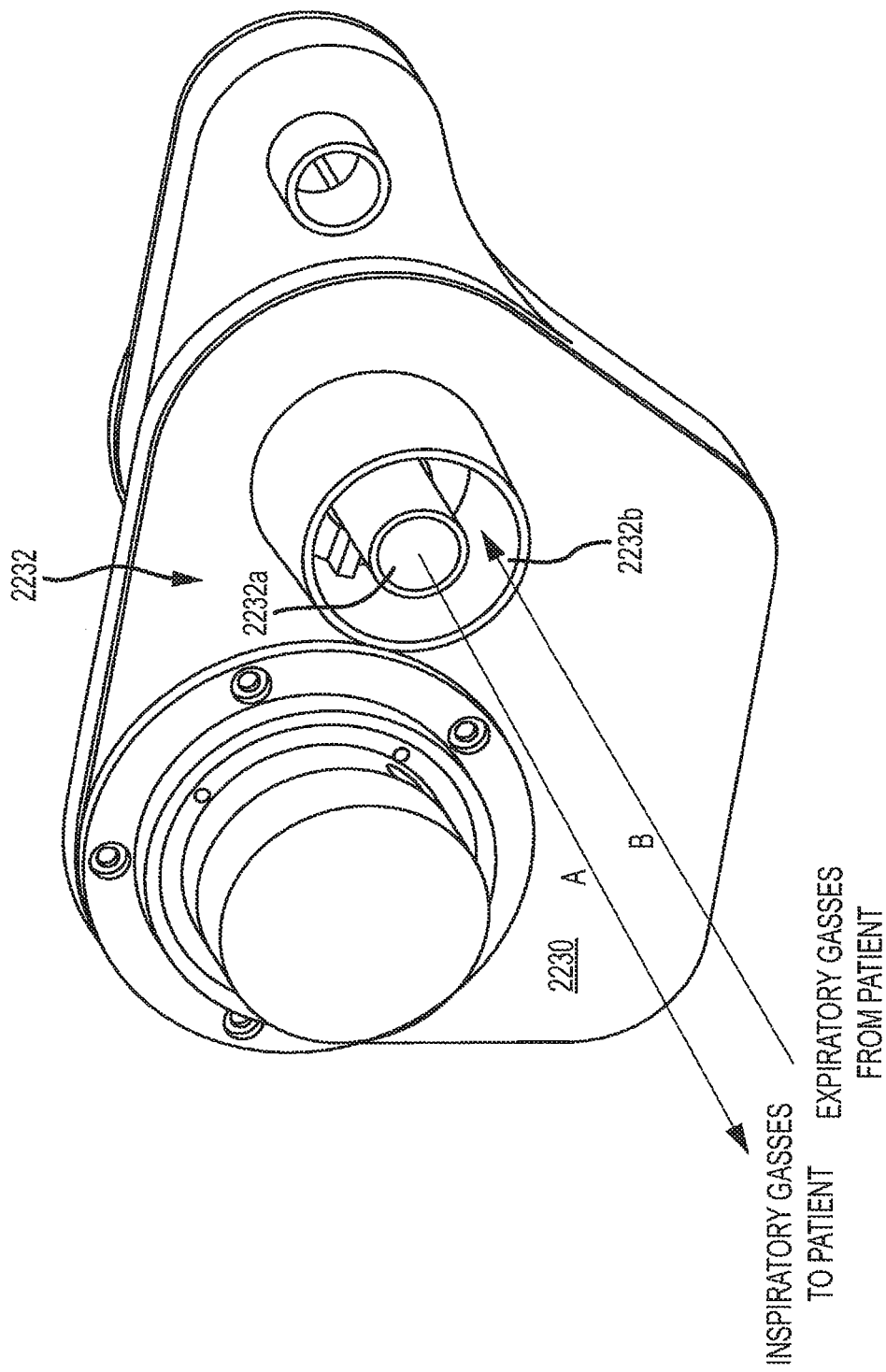

FIG. 22F shows aspects of a patient circuit interface according to embodiments of the present invention. Patient circuit interface 2232 presents a concentric configuration having an inner or inspiratory lumen 2232 a and an outer or expiratory lumen 2232 b. Inner or inspiratory lumen 2232 a operates to carry inspiratory gases toward the patient as indicated by arrow A, and outer or expiratory lumen 2232 b operates to carry expiratory gases away from the patient as indicated by arrow B. Typically, these inspiratory and expiratory gases are transmitted between the patient and patient circuit interface 2232 via a tube assembly, having an inner or inspiratory passage that fluidly communicates with inner or inspiratory lumen 2232 a and an outer or expiratory passage that fluidly communications with outer or expiratory lumen 2232 b. According to exemplary embodiments, treatment systems may include tube connections having concentric, conical fittings that engage with mating conical fittings on a patient circuit, thus providing quick and intuitive attachment of both Inspiratory and Expiratory limbs of patient circuit simultaneously. Concentric arrangement allows a caregiver to engage a patient circuit with a patient in a single motion and can be performed one-handed.

Figure 22G:
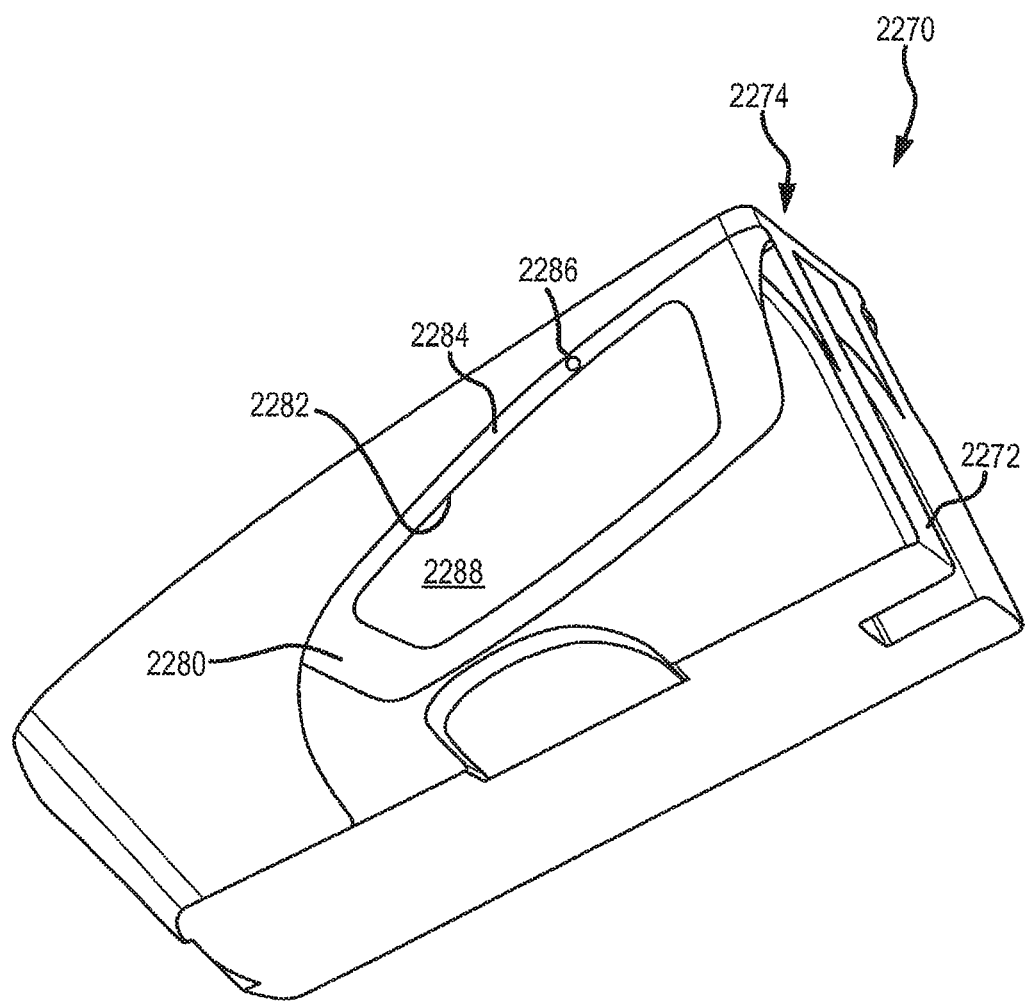

FIG. 22G shows aspects of a case or bonnet 2270 having a handle 2280 according to embodiments of the present invention. Case 2270 can be configured to hold or receive a manifold system as described elsewhere herein. As shown here, handle 2280 can wrap around a back side 2272 of case 2270. This arrangement can strengthen the attachment point and provide impact protection on an upper-back corner 2274 of case 2270. According to some embodiments, handle 2280 wraps around the back side of the case by a distance of about one inch. Handle 2280 may include an attachment point 2282 having an underside 2284. Case 2270 may include an intake port 2286 that is configured to receive fluid into the case. For example, intake port 2286 can be configured to receive cooling air into the case. In some cases, handle 2280 may provide a retainment or recess 2288 for holding or receiving one or more cooling air filters (not shown). Optionally, handle 2280 may be configured as an elastomeric flap disposed on case 2270. In some cases, handle 2280 can include a semi-elastomeric material and can be attached to the underside of an arced cutout detail in a side of the case. According to some embodiments, the handle material can be flexible enough to bend outward when grasped for carrying. Where a handle includes soft material, the soft material can provide impact protection to the case or other structural elements associated with or contained within the case, such as elements of a manifold system. In some embodiments, the protective case is removable. The case can also provide protection against impact and against water intrusion, thus shielding the manifold from unwanted forces, shock, and water damage.

In some instances, a case may have multiples handles. For example, a case may a first handle on the left side of the case, and a second handle on the right side of the case. The handles may be made of moderately soft plastic, and lie flat against the sides of the device when not in use. When used as a handle or for an attachment point for a tie-down, the handle material flexes sufficiently to grasp easily. The handles can also conceal and retain filters at inlets for cooling air to be circulated inside the enclosure of the device. Due to the locations of the inlets, they can be protected from moisture ingress (e.g. rain) when the device is in an upright position, but in some cases may not protect if immersed or allowed to lay face-down.

Figure 23:
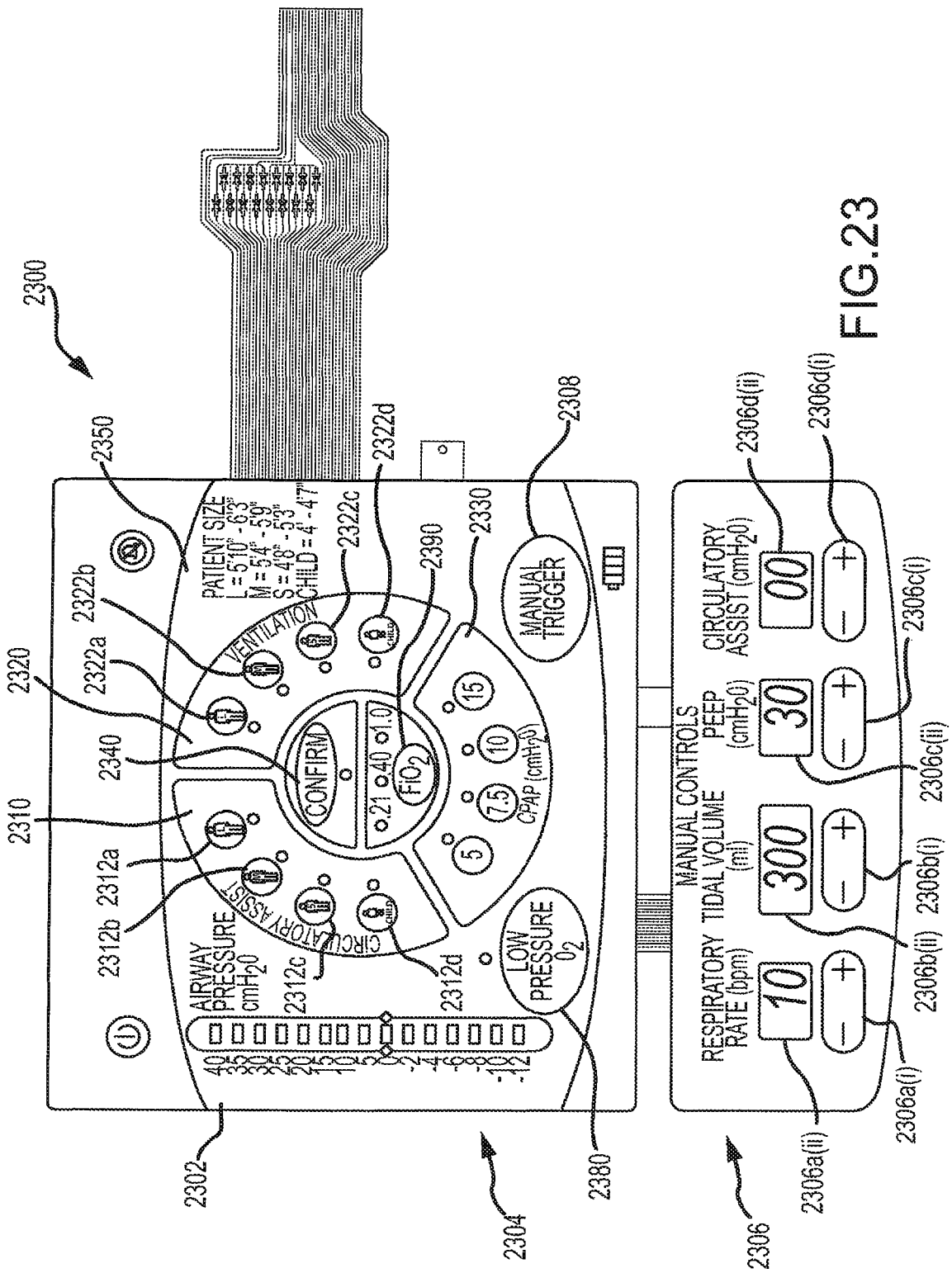
FIG. 23 shows aspects of an intrathoracic pressure regulation system according to embodiments of the present invention.

FIG. 23 illustrates aspects of a user interface 2300 for use with a treatment system according to embodiments of the present invention. What is more, additional details regarding the use and operation of a treatment system can be understood with reference to FIG. 23. As shown here, user interface 2300 includes several sub-interfaces that correspond to various modes of operation or use of the treatment system. For example, interface 2300 includes a circulatory assist mode sub-interface 2310, a ventilation mode sub-interface 2320, and a continuous positive airway pressure (CPAP) mode sub-interface 2330. When in the circulatory assist mode, the treatment system is configured to provide adjustable levels of negative pressure. When in the CPAP mode, the treatment system is configured to provide adjustable levels of continuous positive airway pressure, and when in the ventilation mode, the treatment system is configured to provide positive pressure ventilation with or without positive end expiratory pressure (PEEP). In some cases, a treatment system can be configured to provide a Bilevel Positive Airway Pressure (BIPAP) treatment to administer two levels of pressure, including an Inspiratory Positive Airway Pressure (IPAP) and a lower Expiratory Positive Airway Pressure (EPAP) for easier exhalation. Hence, user interface 2300 may also include a BIPAP mode sub-interface (not shown).

User interface 2300 presents a unique design with several innovative features. As depicted here, the mode sub-interfaces 2310, 2320, and 2330 are presented in a circular layout. User interface 2300 facilitates a two step start process, as follows. For the circulatory assist mode, the user can first press one of the size icons 2312 a, 2312 b, 2312 c, 2312 d depending on the size of the person being treated (i.e. large size adult, medium size adult, small size adult, or child, respectively), and then press the confirm icon 2340 to start operation of the system mode. When determining which size icon to select, the user can refer to a patient size legend 2350 provided on the interface. As shown here, patient size legend 2350 indicates that when treating a person having a height of 5'10" to 6'3" it is appropriate to select the Large size icon, when treating a person having a height of 5'4" to 5'9" it is appropriate to select the Medium size icon, when treating a person having a height of 4'8" to 5'3" it is appropriate to select the Small size icon, and when treating a person having a height of 4' to 4'7" it is appropriate to select the Child size icon. For the ventilation mode, the user can first press one of the size icons 2322 a, 2322 b, 2322 c, 2322 d depending on the size of the person being treated (i.e. large size adult, medium size adult, small size adult, or child, respectively), and then press the confirm icon 2340 to start operation of the system mode. For the CPAP mode, the user can first press one of the pressure amount icons 2332 a, 2332 b, 2332 c, 2332 d depending on the amount of pressure desired (e.g. 5 cmH$_2$O, 7.5 cmH$_2$O, 10 cmH$_2$O, or 15 cmH$_2$O), and then press the confirm icon 2340 to start operation of the system mode. Hence, the interface is intuitive and simple to understand, thus providing a favorable usability and allowing the user to obtain the desired objective. User interface 2300 can also include a pressure indicator 2302 that can display real-time positive and negative airway pressures as determined within the patient's airway with one or more pressure sensors.

User interface 2302 can also be configured to provide a basic mode sub-interface 2304 and an advanced mode sub-interface 2306. As shown here, the basic mode is represented by the upper portion of the display (e.g. where the circle shape is shown) and the advanced mode is represented by the lower portion of the display. According to some embodiments involving the basic mode, the operator makes a decision regarding which of the treatment modes (e.g. circulatory assist, ventilation, or CPAP) to use, and a decision regarding the size of the patient (e.g. Large, Medium, Small, or Child). In the basic mode, other treatment system parameters such as respiratory rate, tidal volume, level of PEEP, and level of negative pressure can be pre-programmed as default values. According to some embodiments involving the advanced mode, the operator can make decisions and adjustments regarding the implementation of certain treatment parameters, respiratory rate, tidal volume, level of PEEP, and level of negative pressure (circulatory assist level), optionally via manual controls. For example, the user can adjust the respiratory rate (bpm) by adjusting the respiratory rate control 2306 $a(i)$, and the respiratory rate can be displayed on the respirator rate display 2306 $a(ii)$. Similarly, the user can adjust the tidal volume (ml) by adjusting the tidal volume control 2306 $b(i)$, and the tidal volume can be displayed on the tidal volume display 2306 $b(ii)$ Likewise, the user can adjust the positive end expiratory pressure (PEEP) (cmH$_2$O) by adjusting the positive end expiratory pressure (PEEP) control 2306 $c(i)$, and the positive end expiratory pressure (PEEP) can be displayed on the positive end expiratory pressure (PEEP) display 2306 $c(ii)$. Further, the user can adjust the circulatory assist (cmH$_2$O) by adjusting the circulatory assist control 2306 $d(i)$, and the circulatory assist can be displayed on the circulatory assist display 2306 $d(ii)$. In some cases, interface 2300 includes a lock-out mechanism 2308, whereby the operator or another individual can activate the mechanism 2308 and thereby lock-out use of the advanced mode.

In some embodiments, a treatment system can be configured to use a measured patient parameter (e.g. end tidal carbon dioxide or ETCO$_2$, cardiac output, transthoracic impedance, muscle oxygenation, muscle pH, or the like) as an indicator of increased circulation and allow the device to regulate the level of negative pressure automatically with a feedback loop control. In some cases, a treatment system can be configured to have a weight less than 12 pounds. The treatment system can incorporate or be controlled by custom software.

In some cases, the exterior user interface surfaces may be covered with a clear, plastic membranous material that can serve multiple purposes. This membrane can protect the user interface from moisture, and can present a surface that is easier to clean than an unprotected control panel. This cover may also be constructed of a material which may provide cushioning around the perimeter of the device.

A low pressure O$_2$ sub-interface 2380 can include an input for operator selection of a low oxygen procedure, for example when the treatment system is coupled with a low pressure oxygen source. Relatedly, a fraction inspired O$_2$ sub-interface 2390 can include an input for operator selection of a fraction inspired oxygen procedure, for example when the treatment system is coupled with a high pressure (e.g. 15 psi) oxygen source. During a fraction inspired oxygen protocol, the system can operate to control a percentage of oxygen administered to the patient. For example, the system can be selected to deliver 100% oxygen, a blend of 40% oxygen and 60% air, a blend of 21% oxygen and 79% air, or the like. Optionally, the percentage can be selected based on the patient's needs.

Figure 24:
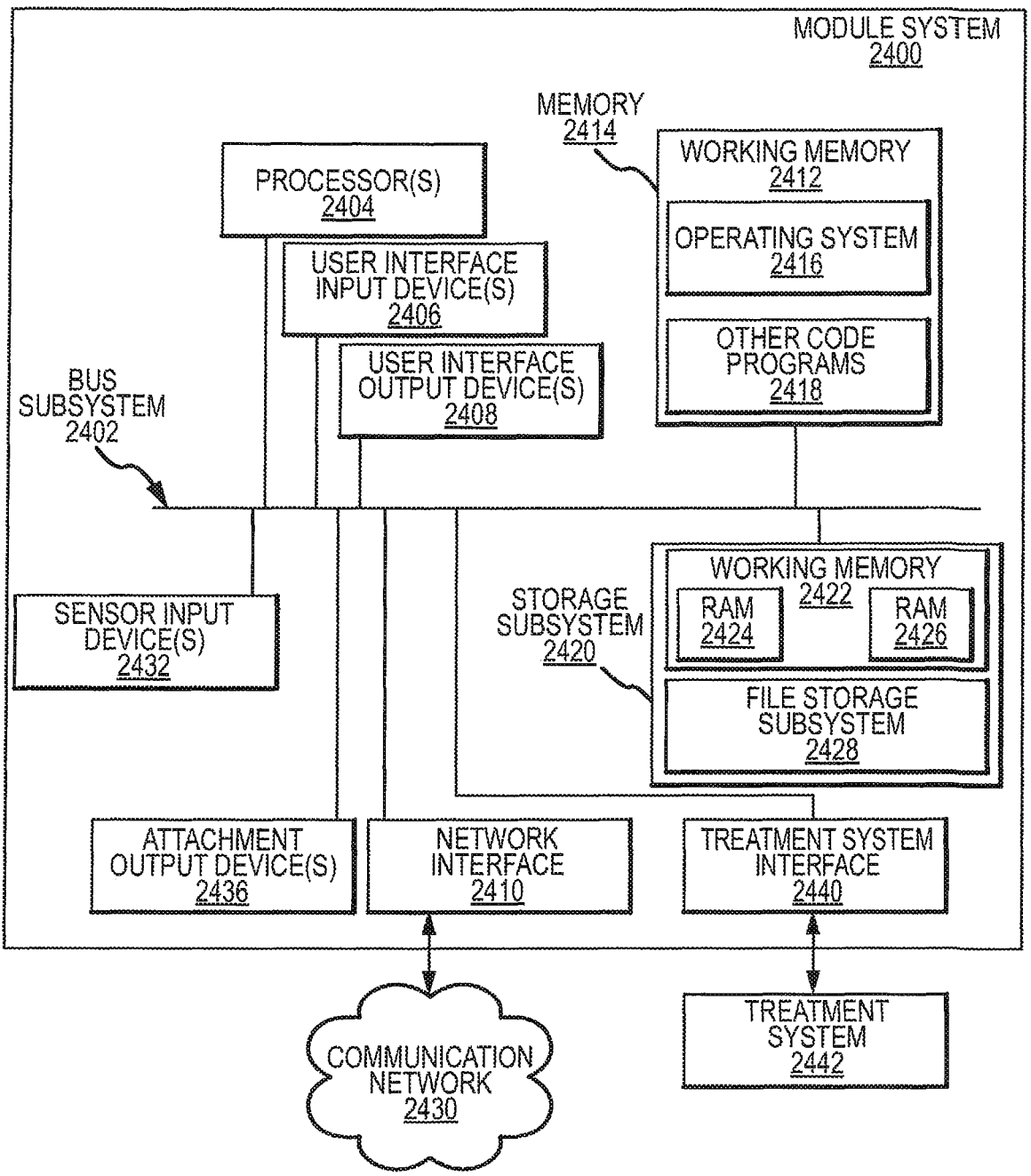
FIG. 24 shows aspects of an intrathoracic pressure regulation system according to embodiments of the present invention.

FIG. 24 is a simplified block diagram of an exemplary module system that broadly illustrates how individual system elements for a module system 2400 may be implemented in a separated or more integrated manner. Module system 2400 may be part of or in connectivity with a treatment system according to embodiments of the present invention. Module system 2400 is well suited for receiving input or information from an operator, a patient, or both, and for displaying output or information as part of an intrathoracic pressure treatment. Module system 2400 as shown here includes hardware elements that are electrically coupled via a bus subsystem 2402, including one or more processors 2404, one or more input devices 2406 such as user interface input devices, one or more output devices 2408 such as user interface output devices, a network interface 2410, and a load system interface 2440 that can receive signals from and transmit signals to load system 2442.

In some embodiments module system 2400 also comprises software elements, shown as being currently located within working memory 2412 of memory 2414, including an operating system 2416 and other code 2418, such as a program designed to implement methods of the invention.

Likewise, in some embodiments module system 2400 may also include a storage subsystem 2420 that can store the basic programming and data constructs that provide the functionality of the various embodiments of the present invention. For example, software modules implementing the functionality of the methods of the present invention, as described herein, may be stored in storage subsystem 2420. These software modules are generally executed by the one or more processors 2404. In a distributed environment, the software modules may be stored on a plurality of computer systems and executed by processors of the plurality of computer systems. Storage subsystem 2420 can include memory subsystem 2422 and file storage subsystem 2428. Memory subsystem 2422 may include a number of memories including a main random access memory (RAM) 2426 for storage of instructions and data during program execution and a read only memory (ROM) 2424 in which fixed instructions are stored. File storage subsystem 2428 can provide persistent (non-volatile) storage for program and data files, and may include tangible storage media which may optionally embody patient, treatment, assessment, or other data. File storage subsystem 2428 may include a hard disk drive, a floppy disk drive along with associated removable media, a Compact Digital Read Only Memory (CD-ROM) drive, an optical drive, DVD, CD-R, CD RW, solid-state removable memory, other removable media cartridges or disks, and the like. One or more of the drives may be located at remote locations on other connected computers at other sites coupled to module system 2400. The modules implementing the functionality of the present invention may be stored by file storage subsystem 2428. In some embodiments, the software or code will provide protocol to allow the module system 2400 to communicate with communication network 2430. Optionally, such communications may include dial-up or internet connection communications.

It is appreciated that system 2400 can be configured to carry out various aspects of methods of the present invention. For example, processor component or module 2404 can be a microprocessor control module configured to receive physiological, device, or treatment parameter signals from sensor input device or module 2432 or user interface input device or module 2406, and to transmit treatment signals to output device or module 2436, user interface output device or module 2408, network interface device or module 2410, or any combination thereof. Each of the devices or modules according to embodiments of the present invention can include one or more software modules on a computer readable medium that is processed by a processor, or hardware modules, or any combination thereof. Any of a variety of commonly used platforms, such as Windows, Macintosh, and Unix, along with any of a variety of commonly used programming languages, may be used to implement embodiments of the present invention.

User interface input devices 2406 may include, for example, a touchpad, a keyboard, pointing devices such as a mouse, a trackball, a graphics tablet, a scanner, a joystick, a touchscreen incorporated into a display, audio input devices such as voice recognition systems, microphones, and other types of input devices. User input devices 2406 may also download a computer executable code from a tangible storage media or from communication network 2430, the code embodying any of the methods of the present invention. It will be appreciated that terminal software may be updated from time to time and downloaded to the terminal as appropriate. In general, use of the term "input device" is intended to include a variety of conventional and proprietary devices and ways to input information into module system 2400.

User interface output devices 2406 may include, for example, a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from module system 2400 to a user.

Bus subsystem 2402 provides a mechanism for letting the various components and subsystems of module system 2400 communicate with each other as intended. The various subsystems and components of module system 2400 need not be at the same physical location but may be distributed at various locations within a distributed network. Although bus subsystem 2402 is shown schematically as a single bus, alternate embodiments of the bus subsystem may utilize multiple busses.

Network interface 2410 can provide an interface to an outside network 2430 or other devices. Outside communication network 2430 can be configured to effect communications as needed or desired with other parties. It can thus receive an electronic packet from module system 2400 and transmit any information as needed or desired back to module system 2400. In addition to providing such infrastructure communications links internal to the system, the communications network system 2430 may also provide a connection to other networks such as the internet and may comprise a wired, wireless, modem, and/or other type of interfacing connection.

It will be apparent to the skilled artisan that substantial variations may be used in accordance with specific requirements. For example, customized hardware might also be used and/or particular elements might be implemented in hardware, software (including portable software, such as applets), or both. Further, connection to other computing devices such as network input/output devices may be employed. Module terminal system 2400 itself can be of varying types including a computer terminal, a personal computer, a portable computer, a workstation, a network computer, or any other data processing system. Due to the ever-changing nature of computers and networks, the description of module system 2400 depicted in FIG. 24 is intended only as a specific example for purposes of illustrating one or more embodiments of the present invention. Many other configurations of module system 2400 are possible having more or less components than the module system depicted in FIG. 24. Any of the modules or components of module system 2400, or any combinations of such modules or components, can be coupled with, or integrated into, or otherwise configured to be in connectivity with, any of the treatment system embodiments disclosed herein. Relatedly, any of the hardware and software components discussed above can be integrated with or configured to interface with other medical assessment or treatment systems used at other locations.

In some embodiments, the module system 2400 can be configured to receive a physiological parameter of the patient at an input module. Physiological parameter data can be transmitted to an assessment module where a physiological profile is determined. The profile can be output to a system user via an output module. In some cases, the module system 2400 can determine a treatment protocol for the patient, based on a physiological parameter or profile, for example by using a treatment module. The treatment can be output to a system user via an output module. Optionally, certain aspects of the treatment can be determined by an output device, and transmitted to a treatment system or a subdevice of a treatment system. Any of a variety of data related to the patient can be input into the module system, including age, weight, sex, treatment history, medical history, and the like. Parameters of treatment regimens or diagnostic evaluations can be determined based on such data.

Figure 25A:
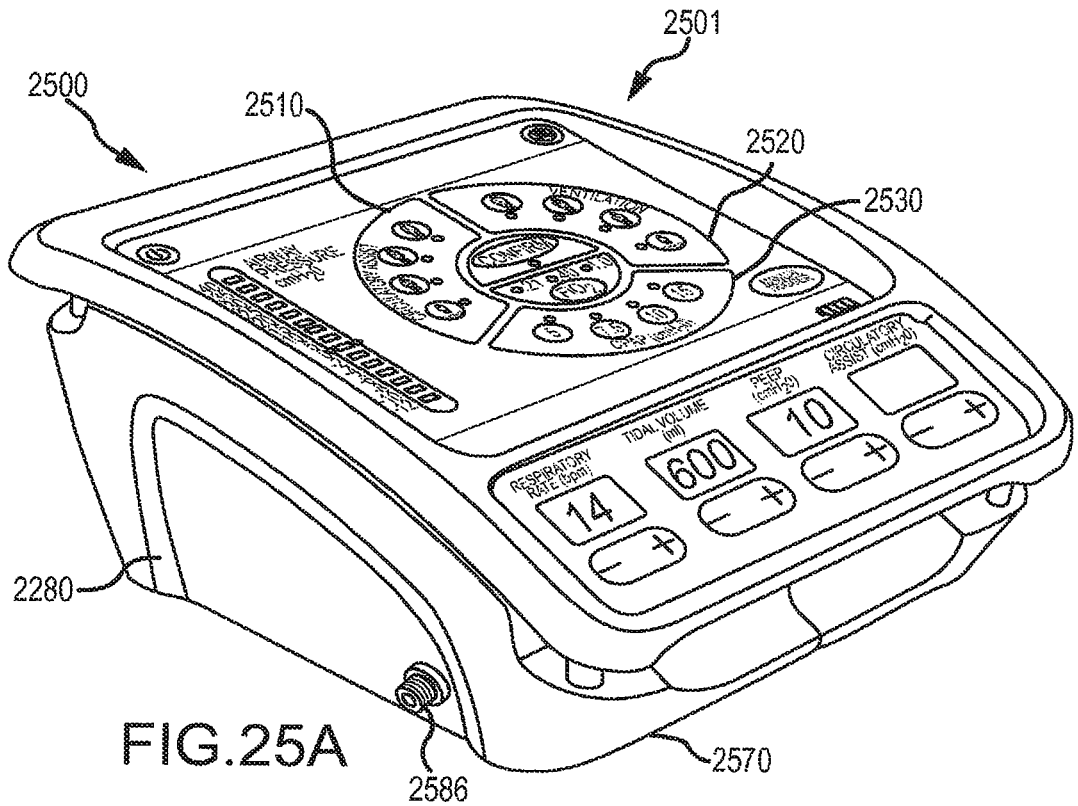
FIGS. 25A and 25B show aspects of an intrathoracic pressure regulation systems according to embodiments of the present invention.
Figure 25B:
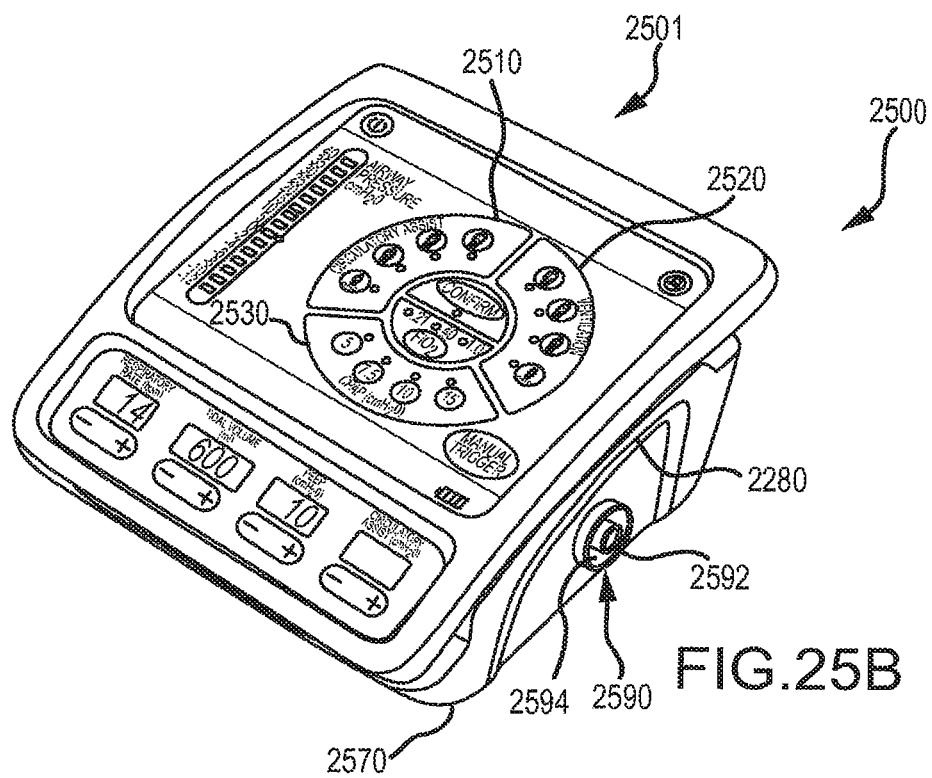

FIGS. 25A and 25B show aspects of an intrathoracic pressure regulator system 2500 according to embodiments of the present invention. According to some embodiment, system 2500 presents a fully automatic device that incorporates both an internal vacuum source and a positive pressure ventilator. Intrathoracic pressure regulator system 2500 can include a processor that accepts an operator selection input designating a circulatory assist mode, a ventilation mode, or a continuous positive airway pressure mode, for example via a circulatory assist mode sub-interface 2510, a ventilation mode sub-interface 2520, and a continuous positive airway pressure (CPAP) mode sub-interface 2530. When in the circulatory assist mode, the treatment system is configured to provide adjustable levels of negative pressure. When in the CPAP mode, the treatment system is configured to provide adjustable levels of continuous positive airway pressure, and when in the ventilation mode, the treatment system is configured to provide positive pressure ventilation with or without positive end expiratory pressure (PEEP). In some cases, a treatment system can be configured to provide a Bilevel Positive Airway Pressure (BIPAP) treatment to administer two levels of pressure, including an Inspiratory Positive Airway Pressure (IPAP) and a lower Expiratory Positive Airway Pressure (EPAP) for easier exhalation. Hence, user interface 2500 may also include a BIPAP mode sub-interface (not shown). Intrathoracic pressure regulator system 2500 can include other interface or system features such as those described elsewhere herein with regard to FIGS. 21 to 24, for example.

In some cases, intrathoracic pressure regulator system 2500 encompasses a blower based transport ventilator with multiple modes, which may include a positive pressure ventilation mode (optionally with adjustable PEEP), a CPAP mode, and a circulatory assist mode. System 2500 may be battery powered. In some cases, system 2500 can be used with or without oxygen treatment. System 2500 may be pre-programmed with desired tidal volume and respiratory rate information based on a body icon selected per a height chart, optionally based on a predicted body weight calculation. In some cases, system 2500 can be used to administer multiple $FiO_2$ levels. System 2500 presents multiple deployment modes which can be activated or deployed with a one button press. A manual mode (on/off) can be disabled at a medical director level. System 2500 may embody integrated CPAP with blending, descending breath waveforms (biomimetic), oxygen or battery power, and auto switching in low oxygen situations.

System 2500 may include a case 2570 having a handle 2580. System 2500 may also include an intake port 2586 that is configured to receive fluid into the case. For example, intake port 2586 can be configured to receive cooling air into the case. System 2500 may also include a patient circuit interface 2590 having an inspiratory lumen 2592 that transmits air, oxygen, or both toward the patient and an expiratory lumen 2594 that transmits expired gas away from the patient. System 2500 may include a manifold assembly which is at least partially contained within case 2570. System 2500 may further include a fixed or adjustable negative pressure mechanism that delivers a negative pressure treatment to the patient via the expiratory lumen, for example when the system is in a circulatory assist mode. System 2500 may also include a positive pressure ventilation mechanism that delivers a positive pressure ventilation treatment to the patient via the inspiratory lumen, for example when the system is in a ventilation mode. System 2500 may also include an adjustable continuous positive airway pressure mechanism that delivers an adjustable continuous positive airway pressure treatment to the patient via the expiratory lumen, for example when the system is in a continuous positive airway pressure mode. System 2500 may include a user display or interface 2501 that displays information to a system user based on patient feedback information received from one or more sensor mechanisms in operative association with the system. Display information may relate to CPR quality during administration of a CPR treatment. Relatedly, display information may relate to circulation parameters or conditions occurring within the patient during administration of a non-CPR treatment (e.g. a treatment for patient shock).

The invention has now been described in detail for purposes of clarity and understanding. However, it will be appreciated that certain changes and modifications may be practiced within the scope of the appended claims.

What is claimed is:

1. A multiple mode ventilation system for providing ventilation treatment to a patient, the system comprising:
   a patient port comprising an inspiratory lumen and an expiratory lumen and adapted to be in fluid communication with the patient's airway;
   a ventilator mechanism in fluid communication with the patient port;
   at least one valve configured to control direction of flow between the ventilator mechanism and the patient port during administration of the ventilation treatment; and
   a user interface configured to receive a user input for assisting a user in operating the ventilator mechanism, the user input comprising at least an indication of patient size, and the user interface further configured to provide for a basic mode or an advanced mode based on the received user input, wherein the advanced mode enables manual control of one or more ventilation parameters provided by the ventilator mechanism,
   wherein the one or more ventilation parameters are provided according to a pre-programmed default when the basic mode is activated, and
   wherein the pre-programmed default is based on an input of the patient size.

2. The ventilation system of claim 1, wherein the one or more ventilation parameters comprises at least one of: respiratory rate, tidal volume, positive end expiratory pressure, and circulatory assist.

3. The ventilation system of claim 1, wherein the received user input from the user interface comprises a lock-out mechanism that locks out use of the advanced mode when activated.

4. The ventilation system of claim 1, wherein the one or more ventilation parameters are provided according to a pre-programmed default when the basic mode is activated.

5. The ventilation system of claim 4, wherein the one or more ventilation parameters provided according to the pre-programmed default comprises at least one of: respiratory rate, tidal volume, positive end expiratory pressure, and level of negative pressure.

6. The ventilation system of claim 1, wherein the received user input from the user interface comprises an indication for operation in at least one of a positive pressure ventilation mode and a continuous positive airway pressure mode.

7. The ventilation system of claim 6, wherein the system, when placed into the positive pressure ventilation mode, is configured to allow a user to adjust a positive end expiratory pressure delivered to the patient.

8. The ventilation system of claim 6, wherein a manually-actuable patient size icon corresponds to the positive pressure ventilation mode.

9. The ventilation system of claim 8, wherein the positive pressure ventilation mode is initiated following a user input that confirms selection of the positive pressure ventilation mode.

10. The ventilation system of claim 6, wherein in the positive pressure ventilation mode the at least one valve is configured to provide fluid communication between the inspiratory lumen of the patient port and the ventilation mechanism.

11. The ventilation system of claim 6, wherein a manually-actuable patient size icon associated with a specific pressure corresponds to the continuous positive airway pressure mode.

12. The ventilation system of claim 11, wherein the continuous positive airway pressure mode is initiated following a user input that confirms selection of the continuous positive airway pressure mode.

13. The ventilation system of claim 6, wherein in the continuous positive airway pressure mode the at least one valve is configured to provide fluid communication between the expiratory lumen of the patient port and the ventilation mechanism.

14. The ventilation system of claim 1, wherein the indication of patient size corresponds to a customized treatment protocol.

15. The ventilation system of claim 14, wherein the customized treatment protocol based on patient size comprises one or more preset ventilation parameters comprising at least one of respiratory rate, tidal volume, and positive end expiratory pressure.

16. The ventilation system of claim 1, wherein the user interface comprises a plurality of selectable icons, each icon corresponding to a predetermined patient size, such that selection of an icon by a user provides the indication of patient size.

17. The ventilation system of claim 16, wherein the plurality of selectable icons corresponding to a predetermined patient size corresponds to patient height.

18. The ventilation system of claim 17, wherein the plurality of selectable icons corresponding to a predetermined patient size corresponds to a predicted patient weight.

19. The ventilation system of claim 16, wherein the plurality of selectable icons are associated with a patient size legend.

20. The ventilation system of claim 1, wherein an exterior surface of the user interface is covered with a clear membrane.

* * * * *

UNITED STATES PATENT AND TRADEMARK OFFICE
CERTIFICATE OF CORRECTION

PATENT NO. : 11,583,645 B2
APPLICATION NO. : 16/685226
DATED : February 21, 2023
INVENTOR(S) : Keith G. Lurie et al.

It is certified that error appears in the above-identified patent and that said Letters Patent is hereby corrected as shown below:

In the Specification

Column 1, Line 26, after 7,195,013 delete ")"

Signed and Sealed this
Twenty-fifth Day of April, 2023

Katherine Kelly Vidal
*Director of the United States Patent and Trademark Office*